United States Patent
Sayler et al.

(12) 
(10) Patent No.: US 6,673,596 B1
(45) Date of Patent: *Jan. 6, 2004

(54) IN VIVO BIOSENSOR APPARATUS AND METHOD OF USE

(75) Inventors: Gary S. Sayler, Blain, TN (US); Michael L. Simpson, Knoxville, TN (US); Bruce M. Applegate, Knoxville, TN (US); Steven A. Ripp, Knoxville, TN (US)

(73) Assignees: UT-Battelle, LLC, Oak Ridge, TN (US); University of Tennessee Research Corporation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/454,071

(22) Filed: Dec. 2, 1999

Related U.S. Application Data

(63) Continuation-in-part of application No. 08/978,439, filed on Nov. 25, 1997, now Pat. No. 6,117,643.

(51) Int. Cl.[7] .................. C12M 3/00; G01N 21/00; C12Q 1/66
(52) U.S. Cl. .................. 435/288.7; 435/288.2; 435/288.5; 435/7.1; 435/8; 422/55; 422/58; 422/61; 422/82.05
(58) Field of Search .................. 436/518, 524, 436/525, 531, 805; 424/9.1, 93.21, 172.1, 152.1, 1.45; 435/8, 189, 336, 6, 7.1, 7.32, 287.1, 287.2, 288.7, 808; 514/3; 422/55, 57, 58, 82.01, 82.05, 82.06, 82.07, 82.08

(56) References Cited

U.S. PATENT DOCUMENTS 4,356,270 A   10/1982   Itakura (List continued on next page.)

FOREIGN PATENT DOCUMENTS

| WO | WO 90/05910 | 5/1990 | |
| WO | WO 93/22678 | 11/1993 | |
| WO | WO 97/06101 | 2/1997 | |
| WO | WO 97/12030 | 4/1997 | |
| WO | 97/12680 | * 4/1997 | ............ B01L/3/14 |
| WO | WO 98/22820 | 5/1998 | |
| WO | WO 98/26277 | 6/1998 | |

OTHER PUBLICATIONS

Nichols et al., Establishment of germ–line–competent embryotic stem (ES) cells using differentiation inhibiting activity, 1990, Development, vol. 110, p. 1341–1348.*

(List continued on next page.)

*Primary Examiner*—Padmashri Ponnaluri
*Assistant Examiner*—My Chau Tran
(74) *Attorney, Agent, or Firm*—Akerman Senterfitt

(57) ABSTRACT

Disclosed are bioluminescent bioreporter integrated circuit devices that detect selected analytes in fluids when implanted in the body of an animal. The device comprises a bioreporter that has been genetically engineered to contain a nucleic acid segment that comprises a cis-activating response element that is responsive to the selected substance operably linked to a gene encoding a bioluminescent reporter polypeptide. In preferred embodiments, the target analyte is glucose, glucagons, or insulin. Exposure of the bioreporter to the target substance causes the response element to up-regulate the nucleic acid sequence encoding the reporter polypeptide to produce a luminescent response that is detected and quantitated. In illustrative embodiments, the bioreporter device is encapsulated on an integrated circuit that is capable of detecting the emitted light, processing the resultant signal, and then remotely reporting the results. Also disclosed are controlled drug delivery systems capable of being directly or indirectly controlled by the detection device that provide drugs such as insulin to the animal in reponse to the amount of target analyte present in the body fluids.

27 Claims, 15 Drawing Sheets

U.S. PATENT DOCUMENTS

| | | | |
|---|---|---|---|
| 4,371,625 A | | 2/1983 | Tiollais |
| 4,444,879 A | * | 4/1984 | Foster et al. ............... 435/7.95 |
| 4,944,659 A | * | 7/1990 | Labbe et al. ............. 417/413.2 |
| 5,109,850 A | | 5/1992 | Blanco et al. |
| 5,294,541 A | | 3/1994 | Kaplan et al. |
| 5,370,684 A | | 12/1994 | Vallana et al. |
| 5,387,247 A | | 2/1995 | Vallana et al. |
| 5,421,816 A | * | 6/1995 | Lipkovker ................... 604/20 |
| 5,428,123 A | | 6/1995 | Ward et al. |
| 5,474,552 A | * | 12/1995 | Palti ............................ 604/67 |
| 5,569,186 A | | 10/1996 | Lord et al. .................... 604/67 |
| 5,605,152 A | * | 2/1997 | Slate et al. ................. 600/316 |
| 5,620,883 A | | 4/1997 | Shao et al. |
| 5,653,755 A | | 8/1997 | Ledergerber |
| 5,702,444 A | * | 12/1997 | Struthers et al. ......... 623/23.64 |
| 5,711,861 A | | 1/1998 | Ward et al. ................. 204/403 |
| 5,711,960 A | | 1/1998 | Shikinami |
| 5,728,281 A | * | 3/1998 | Holmstrom et al. ........ 204/403 |
| 5,756,351 A | | 5/1998 | Isacoff et al. |
| 5,770,389 A | | 6/1998 | Ching et al. ............... 435/7.92 |
| 5,779,734 A | | 7/1998 | Ledergerber |
| 5,795,726 A | * | 8/1998 | Glucksmann .............. 435/7.21 |
| 5,795,790 A | | 8/1998 | Schinstine et al. |
| 5,800,420 A | * | 9/1998 | Gross et al. ............. 604/890.1 |
| 5,814,091 A | | 9/1998 | Dahlberg et al. |
| 5,834,218 A | | 11/1998 | Gremillet ................... 435/7.31 |
| 5,836,935 A | * | 11/1998 | Ashton et al. ........... 604/891.1 |
| 5,843,069 A | * | 12/1998 | Butler et al. ............. 604/891.1 |
| 5,902,598 A | * | 5/1999 | Chen et al. ................. 424/423 |
| 5,935,927 A | * | 8/1999 | Vitek et al. ................... 514/12 |
| 6,001,647 A | * | 12/1999 | Peck et al. .................. 435/325 |
| 6,074,859 A | * | 6/2000 | Hirokawa et al. .......... 435/189 |
| 6,117,643 A | * | 9/2000 | Simpson et al. ............. 435/7.1 |
| 6,132,983 A | * | 10/2000 | Lowe et al. .................... 435/8 |
| 6,143,508 A | * | 11/2000 | Okarma ..................... 435/7.21 |
| 6,262,034 B1 | * | 7/2001 | Mathiowitz et al. .......... 514/44 |
| 6,281,330 B1 | * | 8/2001 | Evans et al. ................ 530/324 |

OTHER PUBLICATIONS

Carty et al. "Identification of cis– and trans–Active Factors Regulating Human Islet Amyloid Polypeptide Gene Expression in Pancreatic B–cells," J. Biol. Chem., 272 (18): 11986–11993, 1997.*

Zandstra et al., Cytokine Manipulation of Primitive Human Hematopoietic Cell Self–Renewal, 1997, Proc. Natl. Acad. Sci. USA, vol. 94, 4698–4703.*

Prockop, D. J., Marrow Stromal Cells as Stem Cells for Nonhematopoietic Tissues, 1997, vol. 276, 71–74.*

Flori, et al., "Application of AN69® Hydrogel to Islet Encapsulation", Evaluation in Streptozotocin–induced Diabetic Rat Model, Annals New York Academy of Sciences, pp. 344–349.

Poitout, et al., "A Glucose Monitoring System for On Line Estimation in Man of Blood Glucose Concentration Using a Miniaturized Glucose Sensor Implanted in the Subcutaneous Tissue and a Wearable Control Unit ", Diabetologia (1993) vol. 36, pp. 658–663.

Malik, et al., "Preservation of Immobilized Bacterial Cell–Matrix by Drying for Direct Use in Microbial Sensors", World Journal of Microbiology and Biotechnology, vol. 9, 1993, pp. 243–247.

Gastaldelli, et al., "Glucose Kinetics in Interstitial Fluid Can Be Predicted by Compartmental Modeling", American Physiological Society, 1997, pp. E494–E505.

Ohgawara, et al., "Membrane Immunoisolation of a Diffusion Chamber for a Bioartificial Pancreas" Artif Organs, vol. 22, No. 9, 1998, pp. 788–794.

Gough, et al., "Advances and Prospects in Glucose Assay Technology", Diabetologia (1997), vol. 40, pp. S102–S107.

Wolfson, et al., "Glucose Concentration at Possible Sensor Tissue Implant Sites", Diabetes Care, vol. 5, No. 3, May–Jun., 1982, pp. 162–165.

Patzer, et al., "A Microchip Glucose Sensor", ASAIO Journal, 1995; vol. 41, pp. M409–M413.

Edenberg, et al., "Polymorphism of the Human Alcohol Dehydrogenase 4 (ADH4) Promoter Affects Gene Expression", Pharmacogenetics, 1999, vol. 9, pp. 25–30.

Gu, et al., "Zenotransplantation of Bioartificial Pancreas Using a Mesh–Reinforced Polyvinyl Alcohol Bag", Cell Transplantation, 1994, vol. 3, Supl. 1, pp. S19–S21.

Almashanu, et al., "Fusion of LuxA and LuxB and its Expression in *E. coli, S. cerevisiae* and *D. melanogaster*", Journal of Bioluminiscence and Chemiluminescence, vol. 5, 1990, pp. 89–97; and.

Siegel, et al., "A Genetically Encoded Optical Probe of Membrane Voltage", Neuron, vol. 19, Oct., 1997, pp. 735–741.

Gagne, et al., "Stable Luciferase Transfected Cells for Studying Steroid Receptor Biological Activity", J. Biolumin. Chemilumin., 1994, vol. 9, pp. 201–209.

Balaguer, et al., "Reporter Cell Lines to Study the Estrogenic Effects of Xenoestrogens", The Science of the Total Environment, vol. 233 (1999), pp. 47–56.

Baker, et al., "Evaluation of an Immunoisolation Membrane Formed by Incorporating a Polyvinyl Alcohol Hydrogel Within a Microporous Filter Support", Cell Transplantation, vol. 6, No. 6, 1997, pp. 585–595.

Ilyas, et al., "β–Catenin Mutations in Cell Lines Established from Human Colorectal Cancers", Proc. Natl. Acad. Sci. USA, vol. 94, Sep., 1997, pp. 10330–10334.

Campbell, et al., "Regulation of the CYP1A1 Promoter in Transgenic Mice: An Exquisitely Sensitive On–Off System for Cell Specific Gene Regulation", Journal of Cell Science, vol. 109, (1996), pp. 2619–2625.

Suzuki, et al., "Number and Volume of Islets Transplanted in Immunobarrier Devices", Cell Transplantation, vol. 7, No. 1, 1998, pp. 47–52.

Boundy, et al., "Regulation of Tyrosine Hydroxylase Promoter Activity by Chronic Morphine in TH9.O–LacZ Transgenic Mice", The Journal of Neuroscience, Dec. 1, 1998, vol. 18(23), pp. 9989–9995.

Taniguchi, et al., "Constant Delivery of Proinsulin by Encapsulation of Transfected Cells", Journal of Surgical Research, vol. 70, (1997), pp. 41–45; and.

Boonyaratanakornkit, et al., "Progesterone Stimulation of Human Insulin–Like Growth Factor–Binding Protein–5 Gene Transcription in Human Osteoblasts is Mediated by a CACCC Sequence in the Proximal Promoter", The Journal of Biological Chemistry, vol. 274, No. 37, Sep., 1999, pp. 26431–26438.

Grygorczyk, et al., "Detection of Intracellular Calcium Elevations in *Xenopus laevis* oocytes: Aequorin Luminescence Versus Electrophysiology", Journal of Neuroscience Methods, vol. 67, (1996), pp. 19–25.

Burczak, et al., "Long–Term in vivo Performance and Biocompatibility of Poly(Vinyl Alcohol) Hydrogel Macrocapsules for Hybrid–Type Type Artificial Pancreas", Biomaterials, vol. 17, No. 24, (1996), pp. 2351–2356.

Kennedy, et al., "Upstream Stimulatory Factor–2 (USF2) Activity is Required for Glucose Stimulation of L–Pyruvate Kinase Promoter Activity in Single Living Isletβ–Cells", The Journal of Biological Chemistry, vol. 272, No. 33, Aug., 1997, pp. 20636–20640.

Doiron, et al., "Transcriptional Glucose Signaling Through the Glucose Response Element is Mediated by the Pentose Phosphate Pathway", The Journal of Biological Chemistry, vol. 272, No. 10, Mar., 1996, pp. 5321–5324.

Zolotukhin, et al., "A "Humanized" Green Fluorescent Protein cDNA Adapted for High–Level Expression in Mammalian Cells", Journal of Virology, Jul., 1996, pp. 4646–4654.

Wilkins, et al., "Integrated Implantable Device for Long-Term Glucose Monitoring", Biosensors & Bioelectrics, vol. 10, (1995), pp. 485–494.

Moussy, et al., "In Vitro and In Vivo Performance and Lifetime of Perfluorinated Ionomer–Coated Glucose Sensors After High–Temperature Curing", Anal. Chem. 1994, vol. 66, pp. 3882–3888.

Ksander, G.A., "Collagen Coatings Reduce the Incidence of Capsule Contracture Around Soft Silicone Rubber Implants in Animals", Anals of Plastic Surgery, vol. 20, No. 3, Mar., 1988; pp. 215–224; and.

Srikantha, et al., "The Sea Pansy *Renilla reniformis* Luciferase Serves as a Sensitive Bioluminescent Reporter for Differential Gene Expression in *Candida albicans*", Journal of Bacteriology, Jan., 1996, pp. 121–129.

Feng, et al., "Transforming Growth Factor–β (TGF–β)–Induced Down–Regulation of Cyclin A Expression Requires a Functional TFG–β Receptor Complex", The Journal of Biological Chemistry, vol. 270, No. 41, Oct., 1995, pp. 24237–24245.

Monaco, A.P., "Transplantation of Pancreatic Islets with Immunoexclusion Membranes", Transplantation Proceedings, vol. 25, No. 3, Jun., 1993, pp. 2234–2236.

Bantle, et al., "Glucose Measurement in Patients with Diabetes Mellitus with Dermal Interstitial Fluid", J. Lab Clin. Med. vol. 130, No. 4, Oct., 1997, pp. 436–441.

Sternberg, et al., "Subcutaneous Glucose Concentration in Humans", Diabetes Care, vol. 18, No. 9, Sep., 1995, pp. 1266–1269.

Tziampazis, et al., Tissue Engineering of A Bioartificial Pancreas: Modeling the Cell Environment and Device Function, Biotechnol. Prog., 1995, vol. 11, pp. 115–126.

Meighen, E.A., "Molecular Biology of Bacterial Bioluminescence", Microbiological Reviews, Mar., 1991, vol. 55, No. 1, pp. 123–142.

Dupriez, et al., "Glucose Response Elements in a Gene That Codes for 6–Phosphofructo–2–Kinase/Fructose–2,6–Bisphosphatase", DNA and Cell Biology, vol. 16, No. 9, 1997, pp. 1075–1085.

Shih, et al., "Two CACCGTG Motifs with Proper Spacing Dictate the Carbohydrate Regulation of Hepatic Gene Transcription", The Journal of Biological Chemistry, vol. 270, No. 37, Sep., 1995, pp. 21991–21997; and.

Aplin, et al. "Signal Transduction and Signal Modulation by Cell Adhesion Receptors: The Role of Integrins, Cadherins, Immunoglobulin–Cell Adhesion Molecules, and Selectins", Pharmacological Reviews, vol. 50, No. 2, 1998, pp. 197–263.

International Search Report dated Apr. 20, 2000 (PCT/US99/28733; 4310.004310).

Ahluwalia et al., "A comparative study of protein immobilization techniques for optical immunosensors," Biosensors and Bioelectronics, 7:207–214, 1991.

Alvarez–Icaza and Bilitewski, "Mass production of biosensors," Anal. Chem., 65:525A–533A, 1993.

Anis et al., "A fiber–optic immunosensor for detecting parathion," Anal. Lett., 25:627–635, 1992.

Arnold, "Fiber–optic biosensors," J. Biotechnol., 15:219–228, 1990.

Bluestein and Chen, "Rapid response fiber optic evanescent wave immunosensors," Immunol. Ser., 53:145–170, 1990.

Blum et al., "Design of luminescence photobiosensors," J. Biolumin. Chemilumin., 4:543–550, 1989.

Chee et al., "Accessing genetic information with high density DNA arrays," Science, 274:610–614, 1996.

Fodor et al., "Multiplexed biochemical assays with biological chips," Nature, 364:555–556, 1993.

Grate et al., "Acoustic wave microsensors," Anal. Chem., 65:987A–996A, 1993.

Griffiths and Hall, "Biosensors—What real progress is being made?," Trends Biotechnol., 11:122–130, 1993.

Hacia et al., "Detection of heterozygous mutations in BRCA1 using high density oligonucleotide arrays and two–colour fluorescence analysis," Nature Genetics, 14:441–447, 1996.

Hacia et al., "Evolutionary sequence comparisons using high–density oligonucleotide arrays," Nature Genetics, 18:155–158, 1998.

Herrero et al., "Transposon vectors containing non–antibiotic resistance selection markers for cloning and stable chromosomal insertion of foreign genes in gram–negative bacteria," J. Bacteriol., 172:6557–6567, 1990.

Hill et al., "A comparison of non–radioactive labeling and detection systems with synthetic oligonucleotide probes for the species identification of mosquitoes in the *Anopheles gambiae* complex," Am. J. Trop. Med. Hyg., 44(6):609–622, 1991.

Janata, In: Principles of Chemical Sensors, Plenum Press, New York, 1989.

Kauffman and Guilbault, "Enzyme electrode biosensors: Theory and applications," Bioanal. Appl. Enzymes, 36:36–133, 1992.

Lee and Thompson, "Fiber optic biosensor assay of Newcastle Disease Virus," J. Immunol. Methods, 166(1):123–131, 1993.

Lipshutz et al., "Using oligonucleotide probe arrays to access genetic diversity," Biotechniques, 19(3):442–447, 1995.

Mrksich and Whitesides, "Patterning self–assembled monolayers using microcontact printing: A new technology for biosensors," Trends Biotechnol., 13:228–235, 1995.

Pease et al., "Light–generated oligonucleotide arrays for rapid DNA sequence analysis," Proc. Natl. Acad. Sci. USA, 91:5022–5026, 1994.

Ogert et al., "Detection of *Clostridium botulinum* toxin A using a fiber optic based biosensor," Anal. Biochem., 205:306–312, 1992.

Swain, "Biosensors: A new realism," *Ann. Biol. Clin.*, 50:175–179, 1992.

Wingard, "Biosensor trends," *Ann. NY Acad. Sci.*, 613:44–53, 1990.

Wood and Gruber, "Transduction in microbial biosensors using multiplexed bioluminescence," *Biosensors & Bioelectronics*, 11(3):207–214, 1996.

International Search Report dated Apr. 13, 1999 (PCT/US98/25295; 4310.002510).

Simpson et al., "Bioluminescent–bioreporter integrated circuits form novel whole–cell biosensors," *TIBTECH*, 16:332–338, 1998.

Webb et al., "Kinetics and repsonse of *Pseudomonas fluorescens* HK44 biosensor," *Biotechnology & Bioengineering*, 54(5):491–502, 1997.

Applegate, Kehrmeyer and Sayler, "A chromosomally based tod–luxCDABE whole–cell reporter for benzene, toluene, ethybenzene, and xylene (BTEX) sensing," *Appl. Environ. Microbiol.*, 64(7):2730–2735, 1998.

Atanasov et al., "Implantation of a refillable glucose monitoring–telemetry device," *Biosensors & Bioelectronics*, 12(7):669–680, 1997.

Atanasov et al., "Short–term canine implantation of a glucose monitoring–telemetry device," *Med. Eng. Phys.*, 18(8):632–640, 1996.

Hay et al., "Construction of a whole–cell bioluminescent reporter for the detection of 2,4–dichlorophenoxy acetate," *Abstracts of the General Meeting of the American Society for Microbiology*, 99:541, 1999.

Heitzer et al., "Continuous on–line pollutant monitoring using a whole cell biosensor based on a bioluminescent catabolic reporter bacterium," *Abstracts of the General Meeting of the American Society for Microbiology*, 93(0):364, 1993.

Heitzer et al., "Optical biosensor for environmental on–line monitoring of naphthalene and salicylate bioavailability with an immobilized bioluminescent catabolic reporter bacterium," *Appl. Environ. Microbiol.*, 60(5):1487–1494, 1994.

King et al., "Rapid, sensitive bioluminescent reporter technology for naphthalene exposure and biodegradation," *Science*, 249(4970):778–781, 1990.

Layton, Muccini, Ghosh, Sayler, "Construction of a bioluminescent reporter strain to detect polychlorinated biphenyls," *Appl. Environ. Microbiol.*, 64(12):5023–5026, 1998.

Matrubutham et al., "Microbial biosensors based on optical detection," *Methods in Biotechnology; Enzyme and Microbial Biosensors: Techniques and Protocols*, 6:249–256, 1998.

Matrubuthan and Sayler, "Performance of bioluminescent reporter bacterium *Pseudomonas fluorescens* HK44 under different culture conditions," *Abstracts of General Meeting of the American Society for Microbiology*, 94(0):450, 1994.

Matrubuthan et al., "Bioluminescense induction response and survival of the bioreporter bacterium *Pseudomonas fluorescens* HK44 in nutrient–deprived conditions," *Appl. Microbiol. Biotechnol.*, 47(5):604–609, 1997.

Simpson et al., "Bioluminescent bioreporter integrated circuits (BBICs): Whole–cell chemical biosensors," *Technical Digest of 1998, Solid–State Sensors and Actuators Conference*, Hilton Head Island, South Carolina, pp. 354–357, 1998.

Simpson et al., "Bioluminescent–bioreporter integrated circuits form novel whole–cell biosensors," *Trends in Biotechnology*, 16(8):332–338, 1998.

Simpson Jellison, Ericson, Dress, Wintenberg, and Bobrek, "Application specific spectral response with CMOS compatible photodiodes," *IEEE Transactions on Electron Devices*, 46(5):905–913, 1999.

Simpson, Dress, Ericson, Jellison, Sitter, Wintenberg and French, "A photospectrometer realized in a standard integrated circuit process," *Rev. Sci. Instr.*, 69(2):377–383, 1998.

Simpson, Sayler, Nivens, Ripp, Paulus and Jellison, "Bioluminescent bioreporter integrated circuits (BBICs)," *Smart Structures and Materials 1998: Smart Electronics and MEMS*, Varadan, McWhorter Singer and Vellekoop, Eds., *Proceedings of SPIE*, 3328:202–212, 1998.

* cited by examiner

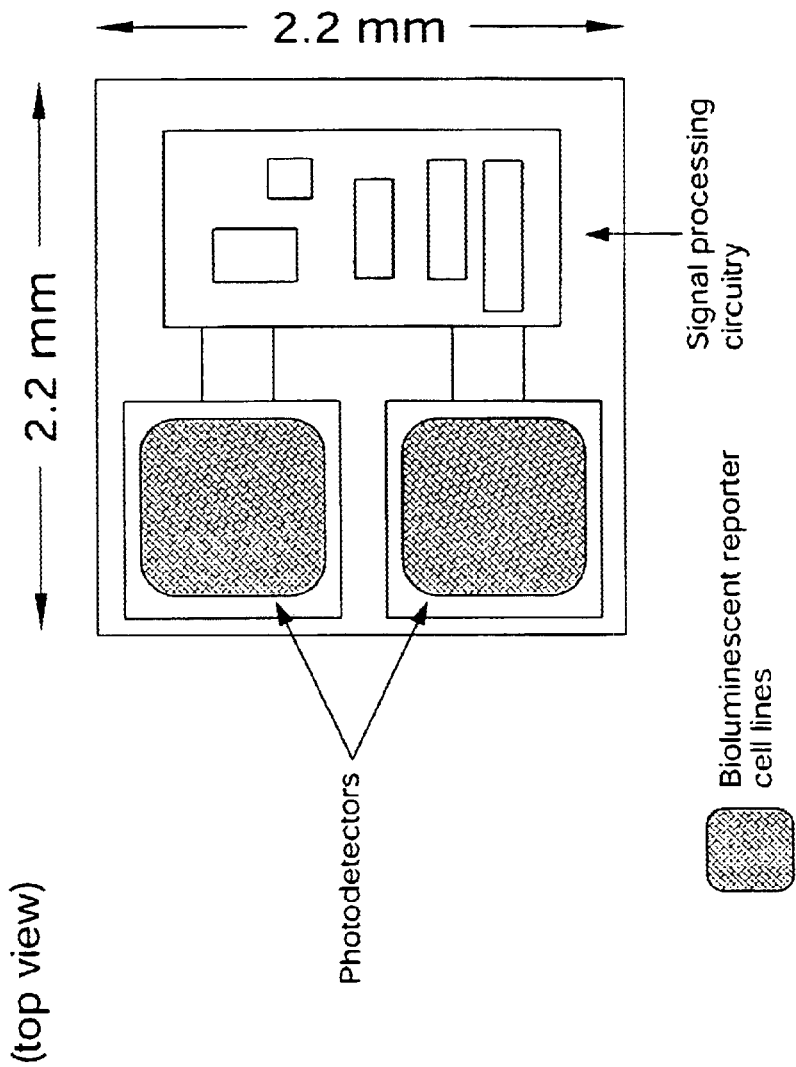

(side view)

(optional membrane)

SEQUENCE LISTING

```
<160> NUMBER OF SEQ ID NOS: 7

<210> SEQ ID NO 1
<211> LENGTH: 7669
<212> TYPE: DNA
<213> ORGANISM: Xenorhabdus luminescens
<220> FEATURE:
<221> NAME/KEY: CDS
<222> LOCATION: (1215)..(2657)
<223> OTHER INFORMATION: LUXC
<220> FEATURE:
<221> NAME/KEY: CDS
<222> LOCATION: (2671)..(3594)
<223> OTHER INFORMATION: LUXD
<220> FEATURE:
<221> NAME/KEY: CDS
<222> LOCATION: (3776)..(4858)
<223> OTHER INFORMATION: LUXA
<220> FEATURE:
<221> NAME/KEY: CDS
<222> LOCATION: (4873)..(5847)
<223> OTHER INFORMATION: LUXB
<220> FEATURE:
<221> NAME/KEY: CDS
```

<222> LOCATION: (6160)..(7272)
<223> OTHER INFORMATION: LUXE

<400> SEQUENCE: 1

```
gaattctcag actcaaatag aacaggattc taaagactta agagcagctg tagatcgtga    60
ttttagtacg atagagccaa cattgagaaa ttatggggca acggaagcac aacttgaaga   120
cgccagagcc aaaatacaca agcttaacca agaacagagg ttatacaaat gacagttaat   180
acagaggcac taataaacag cctaggcaag tcctaccaag aaatttttga tgaagggcta   240
attccttata ggaataagcc aagtggttct cctggggtgc ctaatatttg tattgacatg   300
gtgaaagagg ggatttttttt gtcgtttgaa cggaatagta aaatattaaa cgaaattact   360
ttaagattgc ttagagacga taaagctttg tttatatttc caaatgaatt gccatcaccg   420
ttgaagcatt ctatggatag gggatggtt agagaaaatt taggtgatct gattaaatca   480
ataccaccga gacaaatttt aaaaaggcag tttggttgga aagatctata tcgttttacg   540
gatgaaatca gtatgcagat tcttatgat ttacgtgaac aggttaattc agtgactttc   600
ttgcttacat cagacgtgag ttggtaattt aatatatata cccttcatcc ttcaagttgc   660
tgctttgttg gctgctttct ctcaccccag tcacatagtt atctatgctc tggggattc    720 gttcacttgc cgccgcgctg caacttgaaa tctattgggt atatgctatt ggtaattatg   780
gaaaattgcc tgatttatat ataacttaac ttgtaaacca gataataatt tacatgaata   840
ttatcacgta taaaaaaatt gcgattcttt taatttgaaa tagttcaatt taattgaaac   900
tttttattaa caaatcttgt tgatgtgaaa attttcgttt gctattttaa cagatattgt   960
taaacggaga aggcagcatg ttgatgattc actcagccag actgacagtt ttaagcggaa  1020
aattgcagag tatgatcgca ttctgataaa ggttacaggt cactcgcaac cagaatttca  1080
tctttgtata ttttgttttg ttatttacgt tgcagcaaga caaaaataga agaaacaaat  1140
atttatacaa cccgtttgca agagggttaa acagcaattt aagttgaaat tgccctatta  1200
aatggatggc aaat atg aac aaa aaa att tca ttc att att aac ggt cga   1250
             Met Asn Lys Lys Ile Ser Phe Ile Ile Asn Gly Arg
               1               5                  10 gtt gaa ata ttt cct gaa agt gat gat tta gtg caa tcc att aat ttt   1298
Val Glu Ile Phe Pro Glu Ser Asp Asp Leu Val Gln Ser Ile Asn Phe
        15                  20                  25 ggt gat aat agt gtt cat ttg cca gta ttg aat gat tct caa gta aaa   1346
Gly Asp Asn Ser Val His Leu Pro Val Leu Asn Asp Ser Gln Val Lys
    30                  35                  40 aac att att gat tat aat gaa aat aat gaa ttg caa ttg cat aac att   1394
Asn Ile Ile Asp Tyr Asn Glu Asn Asn Glu Leu Gln Leu His Asn Ile
45                  50                  55                  60 atc aac ttt ctc tat acg gta ggg caa cga tgg aaa aat gaa gaa tat   1442
Ile Asn Phe Leu Tyr Thr Val Gly Gln Arg Trp Lys Asn Glu Glu Tyr
                65                  70                  75 tca aga cgc agg aca tat att cgt gat cta aaa aga tat atg gga tat   1490
Ser Arg Arg Arg Thr Tyr Ile Arg Asp Leu Lys Arg Tyr Met Gly Tyr
            80                  85                  90 tca gaa gaa atg gct aag cta gag gcc aac tgg ata tct atg att ttg   1538
Ser Glu Glu Met Ala Lys Leu Glu Ala Asn Trp Ile Ser Met Ile Leu
        95                  100                 105 tgc tct aaa ggt ggc ctt tat gat ctt gta aaa aat gaa ctt ggt tct   1586
Cys Ser Lys Gly Gly Leu Tyr Asp Leu Val Lys Asn Glu Leu Gly Ser
    110                 115                 120 cgc cat att atg gat gaa tgg cta cct cag gat gaa agt tat att aga   1634
Arg His Ile Met Asp Glu Trp Leu Pro Gln Asp Glu Ser Tyr Ile Arg
```

```
              125                 130                 135                 140
gct ttt ccg aaa gga aaa tcc gta cat ctg ttg acg ggt aat gtg cca          1682
Ala Phe Pro Lys Gly Lys Ser Val His Leu Leu Thr Gly Asn Val Pro
            145                 150                 155 tta tct ggt gtg ctg tct ata ttg cgt gca att tta aca aag aat caa          1730
Leu Ser Gly Val Leu Ser Ile Leu Arg Ala Ile Leu Thr Lys Asn Gln
        160                 165                 170 tgc att ata aaa acc tca tca act gat cct ttt acc gct aat gca tta          1778
Cys Ile Ile Lys Thr Ser Ser Thr Asp Pro Phe Thr Ala Asn Ala Leu
        175                 180                 185 gcg cta agt ttt atc gat gtg gac cct cat cat ccg gta acg cgt tct          1826
Ala Leu Ser Phe Ile Asp Val Asp Pro His His Pro Val Thr Arg Ser
        190                 195                 200 ttg tca gtc gta tat tgg caa cat caa ggc gat ata tca ctc gca aaa          1874
Leu Ser Val Val Tyr Trp Gln His Gln Gly Asp Ile Ser Leu Ala Lys
205                 210                 215                 220 gag att atg caa cat gcg gat gtc gtt gtt gct tgg gga ggg gaa gat          1922
Glu Ile Met Gln His Ala Asp Val Val Val Ala Trp Gly Gly Glu Asp
                225                 230                 235 gcg att aat tgg gct gta aag cat gca cca ccc gat att gac gtg atg          1970
Ala Ile Asn Trp Ala Val Lys His Ala Pro Pro Asp Ile Asp Val Met
        240                 245                 250 aag ttt ggt cct aaa aag agt ttt tgt att att gat aac cct gtt gat          2018
Lys Phe Gly Pro Lys Lys Ser Phe Cys Ile Ile Asp Asn Pro Val Asp
        255                 260                 265 tta gta tcc gca gct aca ggg gcg gct cat gat gtt tgt ttt tac gat          2066
Leu Val Ser Ala Ala Thr Gly Ala Ala His Asp Val Cys Phe Tyr Asp
        270                 275                 280 cag caa gct tgt ttt tcc acc caa aat ata tac atg gga agt cat          2114
Gln Gln Ala Cys Phe Ser Thr Gln Asn Ile Tyr Tyr Met Gly Ser His
285                 290                 295                 300 tat gaa gag ttt aag cta gcg ttg ata gaa aaa ttg aac tta tat gcg          2162
Tyr Glu Glu Phe Lys Leu Ala Leu Ile Glu Lys Leu Asn Leu Tyr Ala
                305                 310                 315 cat ata tta cca aac acc aaa aaa gat ttt gat gaa aag gcg gcc tat          2210
His Ile Leu Pro Asn Thr Lys Lys Asp Phe Asp Glu Lys Ala Ala Tyr
        320                 325                 330 tcc tta gtt caa aaa gaa tgt tta ttt gct gga tta aaa gta gag gtt          2258
Ser Leu Val Gln Lys Glu Cys Leu Phe Ala Gly Leu Lys Val Glu Val
        335                 340                 345 gat gtt cat cag cgc tgg atg gtt att gag tca aat gcg ggt gta gaa          2306
Asp Val His Gln Arg Trp Met Val Ile Glu Ser Asn Ala Gly Val Glu
        350                 355                 360 cta aat caa cca ctt ggc aga tgt gtg tat ctt cat cac gtc gat aat          2354
Leu Asn Gln Pro Leu Gly Arg Cys Val Tyr Leu His His Val Asp Asn
365                 370                 375                 380 att gag caa ata ttg cct tat gtg cga aaa aat aaa acg caa acc ata          2402
Ile Glu Gln Ile Leu Pro Tyr Val Arg Lys Asn Lys Thr Gln Thr Ile
                385                 390                 395 tct gtt ttt cct tgg gag gcc gcg ctt aag tat cga gac tta tta gca          2450
Ser Val Phe Pro Trp Glu Ala Ala Leu Lys Tyr Arg Asp Leu Leu Ala
        400                 405                 410 tta aaa ggt gca gaa agg att gta gaa gca gga atg aat aat ata ttt          2498
Leu Lys Gly Ala Glu Arg Ile Val Glu Ala Gly Met Asn Asn Ile Phe
        415                 420                 425 cgg gtt ggt ggt gct cat gat gga atg aga cct tta caa cga ttg gtg          2546
Arg Val Gly Gly Ala His Asp Gly Met Arg Pro Leu Gln Arg Leu Val
        430                 435                 440 aca tat att tcc cat gaa aga cca tcc cac tat act gct aaa gat gtt          2594
```

```
Thr Tyr Ile Ser His Glu Arg Pro Ser His Tyr Thr Ala Lys Asp Val
445                 450                 455                 460 gcg gtc gaa ata gaa cag act cga ttc ctg gaa gaa gat aag ttc ctg       2642
Ala Val Glu Ile Glu Gln Thr Arg Phe Leu Glu Glu Asp Lys Phe Leu
                    465                 470                 475 gta ttt gtc cca taa taggtaaaag aat atg gaa aat aaa tcc aga tat       2691
Val Phe Val Pro               Met Glu Asn Lys Ser Arg Tyr
            480                                   485 aaa acc atc gac cat gtt att tgt gtt gaa gaa aat aga aaa att cat       2739
Lys Thr Ile Asp His Val Ile Cys Val Glu Glu Asn Arg Lys Ile His
            490                 495                 500 gtc tgg gag acg ctg cca aaa gaa aat agt cca aag aga aaa aat acc       2787
Val Trp Glu Thr Leu Pro Lys Glu Asn Ser Pro Lys Arg Lys Asn Thr
505                 510                 515                 520 ctt att att gcg tcg ggt ttt gcc cgc agg atg gat cat ttt gcc ggt       2835
Leu Ile Ile Ala Ser Gly Phe Ala Arg Arg Met Asp His Phe Ala Gly
                    525                 530                 535 ctg gca gag tat ttg tcg cag aat gga ttt cat gtg atc cgc tat gat       2883
Leu Ala Glu Tyr Leu Ser Gln Asn Gly Phe His Val Ile Arg Tyr Asp
                540                 545                 550 tct ctt cac cac gtt gga ttg agt tca ggg aca att gat gaa ttt aca       2931
Ser Leu His His Val Gly Leu Ser Ser Gly Thr Ile Asp Glu Phe Thr
            555                 560                 565 atg tcc ata gga aaa cag agt tta tta gca gtg gtt gat tgg tta aat       2979
Met Ser Ile Gly Lys Gln Ser Leu Leu Ala Val Val Asp Trp Leu Asn
570                 575                 580 aca cga aaa ata aat aac ctc ggt atg ctg gct tca agc tta tct gcg       3027
Thr Arg Lys Ile Asn Asn Leu Gly Met Leu Ala Ser Ser Leu Ser Ala
585                 590                 595                 600 cgg ata gct tat gca agt cta tct gaa att aat gtc tcg ttt tta att       3075
Arg Ile Ala Tyr Ala Ser Leu Ser Glu Ile Asn Val Ser Phe Leu Ile
                605                 610                 615 acc gca gtc ggt gtg gtt aac tta aga tat act ctc gaa aga gct tta       3123
Thr Ala Val Gly Val Val Asn Leu Arg Tyr Thr Leu Glu Arg Ala Leu
            620                 625                 630 gga ttt gat tat ctc agc tta cct att gat gaa ttg cca gat aat tta       3171
Gly Phe Asp Tyr Leu Ser Leu Pro Ile Asp Glu Leu Pro Asp Asn Leu
        635                 640                 645 gat ttt gaa ggt cat aaa ttg ggt gct gag gtt ttt gcg aga gat tgc       3219
Asp Phe Glu Gly His Lys Leu Gly Ala Glu Val Phe Ala Arg Asp Cys
650                 655                 660 ttt gat tct ggc tgg gaa gat tta act tct aca att aat agt atg atg       3267
Phe Asp Ser Gly Trp Glu Asp Leu Thr Ser Thr Ile Asn Ser Met Met
665                 670                 675                 680 cat ctt gat ata ccg ttt att gct ttt act gca aat aat gac gat tgg       3315
His Leu Asp Ile Pro Phe Ile Ala Phe Thr Ala Asn Asn Asp Asp Trp
                685                 690                 695 gta aag caa gat gaa gtt att aca tta cta tca agc atc cgt agt cat       3363
Val Lys Gln Asp Glu Val Ile Thr Leu Leu Ser Ser Ile Arg Ser His
            700                 705                 710 caa tgt aag ata tat tct tta cta gga agc tca cat gat ttg ggt gag       3411
Gln Cys Lys Ile Tyr Ser Leu Leu Gly Ser Ser His Asp Leu Gly Glu
        715                 720                 725 aac tta gtg gtc ctg cgc aat ttt tat caa tcg gtt acg aaa gcc gct       3459
Asn Leu Val Val Leu Arg Asn Phe Tyr Gln Ser Val Thr Lys Ala Ala
730                 735                 740 atc gcg atg gat aat ggt tgt ctg gat att gat gtc gat att att gag       3507
Ile Ala Met Asp Asn Gly Cys Leu Asp Ile Asp Val Asp Ile Ile Glu
745                 750                 755                 760
```

```
ccg tca ttc gaa cat tta acc att gcg gca gtc aat gaa cgc cga atg      3555
Pro Ser Phe Glu His Leu Thr Ile Ala Ala Val Asn Glu Arg Arg Met
                765                 770                 775 aaa att gag att gaa aat caa gtg att tcg ctg tct taa aacctatacc       3604
Lys Ile Glu Ile Glu Asn Gln Val Ile Ser Leu Ser
        780                 785 aatagatttc gagttgcagc gcggcggcaa gtgaacgcat tcccaggagc atagataact    3664
ctgtgactgg ggtgcgtgaa agcagccaac aaagcagcaa cttgaaggat aagggtata    3724 ttgggataga tagttaactc tatcactcaa atagaaatat aaggactctc t atg aaa    3781
                                                       Met Lys
                                                           790 ttt gga aac ttt ttg ctt aca tac caa ccc ccc caa ttt tct caa aca     3829
Phe Gly Asn Phe Leu Leu Thr Tyr Gln Pro Pro Gln Phe Ser Gln Thr
            795                 800                 805 gag gta atg aaa cgg ttg gtt aaa tta ggt cgc atc tct gag gaa tgc     3877
Glu Val Met Lys Arg Leu Val Lys Leu Gly Arg Ile Ser Glu Glu Cys
        810                 815                 820 ggt ttt gat acc gta tgg tta ctt gag cat cat ttc acg gag ttt ggt     3925
Gly Phe Asp Thr Val Trp Leu Leu Glu His His Phe Thr Glu Phe Gly
    825                 830                 835 ttg ctt ggt aac cct tat gtg gct gct gct tat tta ctt ggc gca acc     3973
Leu Leu Gly Asn Pro Tyr Val Ala Ala Ala Tyr Leu Leu Gly Ala Thr
840                 845                 850                 855 aag aaa ttg aat gta ggg act gcg gct att gtt ctc ccc acc gct cat     4021
Lys Lys Leu Asn Val Gly Thr Ala Ala Ile Val Leu Pro Thr Ala His
            860                 865                 870 cca gtt cgc cag ctt gaa gag gtg aat ttg ttg gat caa atg tca aaa     4069
Pro Val Arg Gln Leu Glu Glu Val Asn Leu Leu Asp Gln Met Ser Lys
        875                 880                 885 gga cga ttt cga ttt ggt att tgt cgg ggg ctt tac aat aaa gat ttt     4117
Gly Arg Phe Arg Phe Gly Ile Cys Arg Gly Leu Tyr Asn Lys Asp Phe
    890                 895                 900 cgc gta ttt ggc aca gat atg aat aac agt cgt gcc tta atg gag tgt     4165
Arg Val Phe Gly Thr Asp Met Asn Asn Ser Arg Ala Leu Met Glu Cys
905                 910                 915 tgg tat aag ttg ata cga aat gga atg act gag gga tat atg gaa gct     4213
Trp Tyr Lys Leu Ile Arg Asn Gly Met Thr Glu Gly Tyr Met Glu Ala
920                 925                 930                 935 gac aac gaa cat att aag ttc cat aag gta aaa gtg ctg ccg acg gca     4261
Asp Asn Glu His Ile Lys Phe His Lys Val Lys Val Leu Pro Thr Ala
            940                 945                 950 tat agt caa ggt ggt gca cct att tat gtc gtt gct gaa tcc gct tcc     4309
Tyr Ser Gln Gly Gly Ala Pro Ile Tyr Val Val Ala Glu Ser Ala Ser
        955                 960                 965 acg act gaa tgg gcc gct caa cat ggt tta ccg atg att tta agt tgg     4357
Thr Thr Glu Trp Ala Ala Gln His Gly Leu Pro Met Ile Leu Ser Trp
    970                 975                 980 att ata aat act aac gaa aag aaa gca caa att gag ctt tat aac gag     4405
Ile Ile Asn Thr Asn Glu Lys Lys Ala Gln Ile Glu Leu Tyr Asn Glu
985                 990                 995 gtc gct caa gaa tat gga cac gat att cat aat atc gac cat tgc tta     4453
Val Ala Gln Glu Tyr Gly His Asp Ile His Asn Ile Asp His Cys Leu
1000                1005                1010                1015 tca tat ata aca tcg gta gac cat gac tca atg aaa gcg aaa gaa att     4501
Ser Tyr Ile Thr Ser Val Asp His Asp Ser Met Lys Ala Lys Glu Ile
                1020                1025                1030 tgc cgg aat ttt ctg ggg cat tgg tat gat tcc tat gtt aat gcc aca     4549
Cys Arg Asn Phe Leu Gly His Trp Tyr Asp Ser Tyr Val Asn Ala Thr
            1035                1040                1045
```

```
acc att ttt gat gat tca gac aaa aca aag ggc tat gat ttc aat aaa    4597
Thr Ile Phe Asp Asp Ser Asp Lys Thr Lys Gly Tyr Asp Phe Asn Lys
        1050                1055                1060 gga caa tgg cgc gac ttt gtc tta aaa gga cat aaa aat act aat cgt    4645
Gly Gln Trp Arg Asp Phe Val Leu Lys Gly His Lys Asn Thr Asn Arg
    1065                1070                1075 cgc gtt gat tac agt tac gaa atc aat ccg gtg gga acc ccg cag gaa    4693
Arg Val Asp Tyr Ser Tyr Glu Ile Asn Pro Val Gly Thr Pro Gln Glu
1080                1085                1090                1095 tgt att gat ata att caa aca gac att gac gcc aca gga ata tca aat    4741
Cys Ile Asp Ile Ile Gln Thr Asp Ile Asp Ala Thr Gly Ile Ser Asn
                1100                1105                1110 att tgt tgt ggg ttt gaa gct aat gga aca gta gat gaa att atc tct    4789
Ile Cys Cys Gly Phe Glu Ala Asn Gly Thr Val Asp Glu Ile Ile Ser
            1115                1120                1125 tcc atg aag ctc ttc cag tct gat gta atg ccg ttt ctt aaa gaa aaa    4837
Ser Met Lys Leu Phe Gln Ser Asp Val Met Pro Phe Leu Lys Glu Lys
        1130                1135                1140 caa cgt tcg cta tta tat tag ctaaggaaaa tgaa atg aaa ttt ggc ttg    4887
Gln Arg Ser Leu Leu Tyr                 Met Lys Phe Gly Leu
    1145                1150                            1155 ttc ttc ctt aac ttt atc aat tca aca act att caa gag caa agt ata    4935
Phe Phe Leu Asn Phe Ile Asn Ser Thr Thr Ile Gln Glu Gln Ser Ile
                1160                1165                1170 gct cgc atg cag gaa ata aca gaa tat gtc gac aaa ttg aat ttt gag    4983
Ala Arg Met Gln Glu Ile Thr Glu Tyr Val Asp Lys Leu Asn Phe Glu
            1175                1180                1185 cag att ttg gtg tgt gaa aat cat ttt tca gat aat ggt gtt gtc ggc    5031
Gln Ile Leu Val Cys Glu Asn His Phe Ser Asp Asn Gly Val Val Gly
        1190                1195                1200 gct cct ttg act gtt tct ggt ttt tta ctt ggc cta aca gaa aaa att    5079
Ala Pro Leu Thr Val Ser Gly Phe Leu Leu Gly Leu Thr Glu Lys Ile
    1205                1210                1215 aaa att ggt tca ttg aat cat gtc att aca act cat cat cct gtc cgc    5127
Lys Ile Gly Ser Leu Asn His Val Ile Thr Thr His His Pro Val Arg
1220                1225                1230                1235 ata gcg gaa gaa gcg tgc tta ttg gat cag tta agc gaa gga aga ttt    5175
Ile Ala Glu Glu Ala Cys Leu Leu Asp Gln Leu Ser Glu Gly Arg Phe
                1240                1245                1250 att tta gga ttt agt gat tgc gag aga aag gat gaa atg cat ttt ttc    5223
Ile Leu Gly Phe Ser Asp Cys Glu Arg Lys Asp Glu Met His Phe Phe
            1255                1260                1265 aat cgc cct gaa caa tac cag cag caa tta ttt gaa gaa tgc tat gac    5271
Asn Arg Pro Glu Gln Tyr Gln Gln Gln Leu Phe Glu Glu Cys Tyr Asp
        1270                1275                1280 att att aac gat gct tta aca aca ggc tat tgt aat cca aat ggc gat    5319
Ile Ile Asn Asp Ala Leu Thr Thr Gly Tyr Cys Asn Pro Asn Gly Asp
    1285                1290                1295 ttt tat aat ttc ccc aaa ata tcc gtg aat ccc cat gct tat acg caa    5367
Phe Tyr Asn Phe Pro Lys Ile Ser Val Asn Pro His Ala Tyr Thr Gln
1300                1305                1310                1315 aac ggg cct cgg aaa tat gta aca gca aca agt tgt cat gtt gtt gag    5415
Asn Gly Pro Arg Lys Tyr Val Thr Ala Thr Ser Cys His Val Val Glu
                1320                1325                1330 tgg gct gct aaa aaa ggc att cct cta atc ttt aag tgg gat gat tcc    5463
Trp Ala Ala Lys Lys Gly Ile Pro Leu Ile Phe Lys Trp Asp Asp Ser
            1335                1340                1345 aat gaa gtt aaa cat gaa tat gcg aaa aga tat caa gcc ata gca ggt    5511
Asn Glu Val Lys His Glu Tyr Ala Lys Arg Tyr Gln Ala Ile Ala Gly
```

-continued

|  | 1350 | 1355 | 1360 |  |
|---|---|---|---|---|
| gaa tat ggt gtt gac ctg gca gag ata gat cat cag tta atg ata ttg | | | | 5559 |
| Glu Tyr Gly Val Asp Leu Ala Glu Ile Asp His Gln Leu Met Ile Leu | | | | |
| 1365 | | 1370 | 1375 | | gtt aac tat agt gaa gac agt gag aaa gct aaa gag gaa acg cgt gca 5607
Val Asn Tyr Ser Glu Asp Ser Glu Lys Ala Lys Glu Glu Thr Arg Ala
1380 1385 1390 1395 ttt ata agt gat tat att ctt gca atg cac cct aat gaa aat ttc gaa 5655
Phe Ile Ser Asp Tyr Ile Leu Ala Met His Pro Asn Glu Asn Phe Glu
1400 1405 1410 aag aaa ctt gaa gaa ata atc aca gaa aac tcc gtc gga gat tat atg 5703
Lys Lys Leu Glu Glu Ile Ile Thr Glu Asn Ser Val Gly Asp Tyr Met
1415 1420 1425 gaa tgt aca act gcg gct aaa ttg gca atg gag aaa tgt ggt gca aaa 5751
Glu Cys Thr Thr Ala Ala Lys Leu Ala Met Glu Lys Cys Gly Ala Lys
1430 1435 1440 ggt ata tta ttg tcc ttt gaa tca atg agt gat ttt aca cat caa ata 5799
Gly Ile Leu Leu Ser Phe Glu Ser Met Ser Asp Phe Thr His Gln Ile
1445 1450 1455 aac gca att gat att gtc aat gat aat att aaa aag tat cac atg taa 5847
Asn Ala Ile Asp Ile Val Asn Asp Asn Ile Lys Lys Tyr His Met
1460 1465 1470 1475 tatacccctat ggatttcaag gtgcatcgcg acggcaaggg agcgaatccc cgggagcata 5907 tacccaatag atttcaagtt gcagtgcggc ggcaagtgaa cgcatcccca ggagcataga 5967 taactatgtg actggggtaa gtgaacgcag ccaacaaagc agcagcttga agatgaagg 6027 gtatagataa cgatgtgacc ggggtgcgtg aacgcagcca acaaagaggc aacttgaaag 6087 ataacgggta taaagggta tagcagtcac tctgccatat cctttaatat tagctgccga 6147 ggtaaaacag gt atg act tca tat gtt gat aaa caa gaa atc aca gca agt 6198
Met Thr Ser Tyr Val Asp Lys Gln Glu Ile Thr Ala Ser
1480 1485 tca gaa att gat gat ttg att ttt tcg agt gat cca tta gtc tgg tct 6246
Ser Glu Ile Asp Asp Leu Ile Phe Ser Ser Asp Pro Leu Val Trp Ser
1490 1495 1500 tac gac gaa cag gaa aag att aga aaa aaa ctt gtg ctt gat gcg ttt 6294
Tyr Asp Glu Gln Glu Lys Ile Arg Lys Lys Leu Val Leu Asp Ala Phe
1505 1510 1515 1520 cgt cat cac tat aaa cat tgt caa gaa tac cgt cac tac tgt cag gca 6342
Arg His His Tyr Lys His Cys Gln Glu Tyr Arg His Tyr Cys Gln Ala
1525 1530 1535 cat aaa gta gat gac aat att acg gaa att gat gat ata cct gta ttc 6390
His Lys Val Asp Asp Asn Ile Thr Glu Ile Asp Asp Ile Pro Val Phe
1540 1545 1550 cca aca tca gtg ttt aag ttt act cgc tta tta act tct aat gag aac 6438
Pro Thr Ser Val Phe Lys Phe Thr Arg Leu Leu Thr Ser Asn Glu Asn
1555 1560 1565 gaa att gaa agt tgg ttt acc agt agt ggc aca aat ggc tta aaa agt 6486
Glu Ile Glu Ser Trp Phe Thr Ser Ser Gly Thr Asn Gly Leu Lys Ser
1570 1575 1580 cag gta cca cgt gac aga cta agt att gag agg ctc tta ggc tct gta 6534
Gln Val Pro Arg Asp Arg Leu Ser Ile Glu Arg Leu Leu Gly Ser Val
1585 1590 1595 1600 agt tat ggt atg aaa tat att ggt agt tgg ttc gat cat caa atg gaa 6582
Ser Tyr Gly Met Lys Tyr Ile Gly Ser Trp Phe Asp His Gln Met Glu
1605 1610 1615 ttg gtc aac ctg gga cca gat aga ttt aat gct cat aat att tgg ttt 6630
Leu Val Asn Leu Gly Pro Asp Arg Phe Asn Ala His Asn Ile Trp Phe
1620 1625 1630

-continued

```
aaa tat gtt atg agc ttg gta gag tta tta tat cct acg tca ttc acc      6678
Lys Tyr Val Met Ser Leu Val Glu Leu Leu Tyr Pro Thr Ser Phe Thr
        1635                1640                1645 gta aca gaa gaa cac ata gat ttc gtt cag aca tta aat agt ctt gag      6726
Val Thr Glu Glu His Ile Asp Phe Val Gln Thr Leu Asn Ser Leu Glu
    1650                1655                1660 cga ata aaa cat caa ggg aaa gat att tgt ctt att ggt tcg cca tac      6774
Arg Ile Lys His Gln Gly Lys Asp Ile Cys Leu Ile Gly Ser Pro Tyr
1665                1670                1675                1680 ttt att tat ttg ctc tgc cgt tat atg aaa gat aaa aat atc tca ttt      6822
Phe Ile Tyr Leu Leu Cys Arg Tyr Met Lys Asp Lys Asn Ile Ser Phe
                1685                1690                1695 tct gga gat aaa agt ctt tat att ata acg ggg gga ggc tgg aaa agt      6870
Ser Gly Asp Lys Ser Leu Tyr Ile Ile Thr Gly Gly Gly Trp Lys Ser
            1700                1705                1710 tac gaa aaa gaa tct ttg aag cgt aat gat ttc aat cat ctt tta ttc      6918
Tyr Glu Lys Glu Ser Leu Lys Arg Asn Asp Phe Asn His Leu Leu Phe
        1715                1720                1725 gac act ttc aac ctc agt aat att aac cag atc cgt gat ata ttt aat      6966
Asp Thr Phe Asn Leu Ser Asn Ile Asn Gln Ile Arg Asp Ile Phe Asn
    1730                1735                1740 caa gtt gaa ctc aac act tgt ttc ttt gag gat gaa atg caa cgt aaa      7014
Gln Val Glu Leu Asn Thr Cys Phe Phe Glu Asp Glu Met Gln Arg Lys
1745                1750                1755                1760 cat gtt ccg ccg tgg gta tat gcg cga gca ctt gat cct gaa aca ttg      7062
His Val Pro Pro Trp Val Tyr Ala Arg Ala Leu Asp Pro Glu Thr Leu
                1765                1770                1775 aaa ccg gta cct gat ggg atg cct ggt ttg atg agt tat atg gat gca      7110
Lys Pro Val Pro Asp Gly Met Pro Gly Leu Met Ser Tyr Met Asp Ala
            1780                1785                1790 tca tca acg agt tat ccg gca ttt att gtt acc gat gat atc gga ata      7158
Ser Ser Thr Ser Tyr Pro Ala Phe Ile Val Thr Asp Asp Ile Gly Ile
        1795                1800                1805 att agc aga gaa tat ggt caa tat cct ggt gta ttg gtt gaa att tta      7206
Ile Ser Arg Glu Tyr Gly Gln Tyr Pro Gly Val Leu Val Glu Ile Leu
    1810                1815                1820 cgt cgc gtt aat acg agg aaa caa aaa ggt tgt gct tta agc tta act      7254
Arg Arg Val Asn Thr Arg Lys Gln Lys Gly Cys Ala Leu Ser Leu Thr
1825                1830                1835                1840 gaa gca ttt ggt agt tga tagtttcttt ggaaagagga gcagtcaaag             7302
Glu Ala Phe Gly Ser
                1845 gctcatttgt tcaatgcttt tgcgaaacgt tttgtcgaac tctaggcgaa ggttctcgac    7362 tttccccgca tcagggtat  atacaagtaa aaaagctcag ggggtaaacc tgagcttggg    7422 atgttgattt ttaagtatga gatacatggg cggatttaaa taacggagtc agtttggaaa    7482 tatcaacggt cttttctgct ttatcgaggc tataagtttc ttgcagtttt aaccacaacc    7542 gcggagagct gccaagtact tgtgacagtt ttattgccat ctctggcgtg actgctgctt    7602 tacacgatac taaacgttga accgtagagg gagcaacatt caatgcccgc gctaagttca    7662 cgaattc                                                              7669
```

<210> SEQ ID NO 2
<211> LENGTH: 480
<212> TYPE: PRT
<213> ORGANISM: Xenorhabdus luminescens

<400> SEQUENCE: 2

-continued

```
Met Asn Lys Lys Ile Ser Phe Ile Ile Asn Gly Arg Val Glu Ile Phe
 1               5                  10                  15

Pro Glu Ser Asp Asp Leu Val Gln Ser Ile Asn Phe Gly Asp Asn Ser
             20                  25                  30

Val His Leu Pro Val Leu Asn Asp Ser Gln Val Lys Asn Ile Ile Asp
         35                  40                  45

Tyr Asn Glu Asn Glu Leu Gln Leu His Asn Ile Ile Asn Phe Leu
     50                  55                  60

Tyr Thr Val Gly Gln Arg Trp Lys Asn Glu Glu Tyr Ser Arg Arg Arg
 65                  70                  75                  80

Thr Tyr Ile Arg Asp Leu Lys Arg Tyr Met Gly Tyr Ser Glu Glu Met
                 85                  90                  95

Ala Lys Leu Glu Ala Asn Trp Ile Ser Met Ile Leu Cys Ser Lys Gly
             100                 105                 110

Gly Leu Tyr Asp Leu Val Lys Asn Glu Leu Gly Ser Arg His Ile Met
         115                 120                 125

Asp Glu Trp Leu Pro Gln Asp Glu Ser Tyr Ile Arg Ala Phe Pro Lys
     130                 135                 140

Gly Lys Ser Val His Leu Leu Thr Gly Asn Val Pro Leu Ser Gly Val
145                 150                 155                 160

Leu Ser Ile Leu Arg Ala Ile Leu Thr Lys Asn Gln Cys Ile Ile Lys
                 165                 170                 175

Thr Ser Ser Thr Asp Pro Phe Thr Ala Asn Ala Leu Ala Leu Ser Phe
             180                 185                 190

Ile Asp Val Asp Pro His His Pro Val Thr Arg Ser Leu Ser Val Val
         195                 200                 205

Tyr Trp Gln His Gln Gly Asp Ile Ser Leu Ala Lys Glu Ile Met Gln
     210                 215                 220

His Ala Asp Val Val Ala Trp Gly Gly Glu Asp Ala Ile Asn Trp
225                 230                 235                 240

Ala Val Lys His Ala Pro Pro Asp Ile Asp Val Met Lys Phe Gly Pro
                 245                 250                 255

Lys Lys Ser Phe Cys Ile Ile Asp Asn Pro Val Asp Leu Val Ser Ala
             260                 265                 270

Ala Thr Gly Ala Ala His Asp Val Cys Phe Tyr Asp Gln Gln Ala Cys
         275                 280                 285

Phe Ser Thr Gln Asn Ile Tyr Tyr Met Gly Ser His Tyr Glu Glu Phe
     290                 295                 300

Lys Leu Ala Leu Ile Glu Lys Leu Asn Leu Tyr Ala His Ile Leu Pro
305                 310                 315                 320

Asn Thr Lys Lys Asp Phe Asp Glu Lys Ala Ala Tyr Ser Leu Val Gln
                 325                 330                 335

Lys Glu Cys Leu Phe Ala Gly Leu Lys Val Glu Val Asp Val His Gln
             340                 345                 350

Arg Trp Met Val Ile Glu Ser Asn Ala Gly Val Glu Leu Asn Gln Pro
         355                 360                 365

Leu Gly Arg Cys Val Tyr Leu His His Val Asp Asn Ile Glu Gln Ile
     370                 375                 380

Leu Pro Tyr Val Arg Lys Asn Lys Thr Gln Thr Ile Ser Val Phe Pro
385                 390                 395                 400

Trp Glu Ala Ala Leu Lys Tyr Arg Asp Leu Leu Ala Leu Lys Gly Ala
                 405                 410                 415

Glu Arg Ile Val Glu Ala Gly Met Asn Asn Ile Phe Arg Val Gly Gly
```

```
                      420               425               430
Ala His Asp Gly Met Arg Pro Leu Gln Arg Leu Val Thr Tyr Ile Ser
        435               440               445

His Glu Arg Pro Ser His Tyr Thr Ala Lys Asp Val Ala Val Glu Ile
    450               455               460

Glu Gln Thr Arg Phe Leu Glu Asp Lys Phe Leu Val Phe Val Pro
465               470               475               480

<210> SEQ ID NO 3
<211> LENGTH: 307
<212> TYPE: PRT
<213> ORGANISM: Xenorhabdus luminescens

<400> SEQUENCE: 3

Met Glu Asn Lys Ser Arg Tyr Lys Thr Ile Asp His Val Ile Cys Val
  1               5                  10                  15

Glu Glu Asn Arg Lys Ile His Val Trp Glu Thr Leu Pro Lys Glu Asn
                 20                  25                  30

Ser Pro Lys Arg Lys Asn Thr Leu Ile Ile Ala Ser Gly Phe Ala Arg
             35                  40                  45

Arg Met Asp His Phe Ala Gly Leu Ala Glu Tyr Leu Ser Gln Asn Gly
         50                  55                  60

Phe His Val Ile Arg Tyr Asp Ser Leu His Val Gly Leu Ser Ser
 65                  70                  75                  80

Gly Thr Ile Asp Glu Phe Thr Met Ser Ile Gly Lys Gln Ser Leu Leu
                 85                  90                  95

Ala Val Val Asp Trp Leu Asn Thr Arg Lys Ile Asn Asn Leu Gly Met
            100                 105                 110

Leu Ala Ser Ser Leu Ser Ala Arg Ile Ala Tyr Ala Ser Leu Ser Glu
        115                 120                 125

Ile Asn Val Ser Phe Leu Ile Thr Ala Val Gly Val Val Asn Leu Arg
    130                 135                 140

Tyr Thr Leu Glu Arg Ala Leu Gly Phe Asp Tyr Leu Ser Leu Pro Ile
145                 150                 155                 160

Asp Glu Leu Pro Asp Asn Leu Asp Phe Glu Gly His Lys Leu Gly Ala
                165                 170                 175

Glu Val Phe Ala Arg Asp Cys Phe Asp Ser Gly Trp Glu Asp Leu Thr
            180                 185                 190

Ser Thr Ile Asn Ser Met Met His Leu Asp Ile Pro Phe Ile Ala Phe
        195                 200                 205

Thr Ala Asn Asn Asp Asp Trp Val Lys Gln Asp Glu Val Ile Thr Leu
    210                 215                 220

Leu Ser Ser Ile Arg Ser His Gln Cys Lys Ile Tyr Ser Leu Leu Gly
225                 230                 235                 240

Ser Ser His Asp Leu Gly Glu Asn Leu Val Val Leu Arg Asn Phe Tyr
                245                 250                 255

Gln Ser Val Thr Lys Ala Ala Ile Ala Met Asp Asn Gly Cys Leu Asp
            260                 265                 270

Ile Asp Val Asp Ile Ile Glu Pro Ser Phe Glu His Leu Thr Ile Ala
        275                 280                 285

Ala Val Asn Glu Arg Arg Met Lys Ile Glu Ile Glu Asn Gln Val Ile
    290                 295                 300

Ser Leu Ser
305
```

<210> SEQ ID NO 4
<211> LENGTH: 360
<212> TYPE: PRT
<213> ORGANISM: Xenorhabdus luminescens

<400> SEQUENCE: 4

Met Lys Phe Gly Asn Phe Leu Leu Thr Tyr Gln Pro Gln Phe Ser
1               5                   10                  15
Gln Thr Glu Val Met Lys Arg Leu Val Lys Leu Gly Arg Ile Ser Glu
            20                  25                  30
Glu Cys Gly Phe Asp Thr Val Trp Leu Leu Glu His His Phe Thr Glu
        35                  40                  45
Phe Gly Leu Leu Gly Asn Pro Tyr Val Ala Ala Tyr Leu Leu Gly
    50                  55                  60
Ala Thr Lys Lys Leu Asn Val Gly Thr Ala Ala Ile Val Leu Pro Thr
65                  70                  75                  80
Ala His Pro Val Arg Gln Leu Glu Glu Val Asn Leu Leu Asp Gln Met
                85                  90                  95
Ser Lys Gly Arg Phe Arg Phe Gly Ile Cys Arg Gly Leu Tyr Asn Lys
            100                 105                 110
Asp Phe Arg Val Phe Gly Thr Asp Met Asn Asn Ser Arg Ala Leu Met
        115                 120                 125
Glu Cys Trp Tyr Lys Leu Ile Arg Asn Gly Met Thr Glu Gly Tyr Met
    130                 135                 140
Glu Ala Asp Asn Glu His Ile Lys Phe His Lys Val Lys Val Leu Pro
145                 150                 155                 160
Thr Ala Tyr Ser Gln Gly Gly Ala Pro Ile Tyr Val Val Ala Glu Ser
                165                 170                 175
Ala Ser Thr Thr Glu Trp Ala Ala Gln His Gly Leu Pro Met Ile Leu
            180                 185                 190
Ser Trp Ile Ile Asn Thr Asn Glu Lys Lys Ala Gln Ile Glu Leu Tyr
        195                 200                 205
Asn Glu Val Ala Gln Glu Tyr Gly His Asp Ile His Asn Ile Asp His
    210                 215                 220
Cys Leu Ser Tyr Ile Thr Ser Val Asp His Asp Ser Met Lys Ala Lys
225                 230                 235                 240
Glu Ile Cys Arg Asn Phe Leu Gly His Trp Tyr Asp Ser Tyr Val Asn
                245                 250                 255
Ala Thr Thr Ile Phe Asp Asp Ser Asp Lys Thr Lys Gly Tyr Asp Phe
            260                 265                 270
Asn Lys Gly Gln Trp Arg Asp Phe Val Leu Lys Gly His Lys Asn Thr
        275                 280                 285
Asn Arg Arg Val Asp Tyr Ser Tyr Glu Ile Asn Pro Val Gly Thr Pro
    290                 295                 300
Gln Glu Cys Ile Asp Ile Ile Gln Thr Asp Ile Asp Ala Thr Gly Ile
305                 310                 315                 320
Ser Asn Ile Cys Cys Gly Phe Glu Ala Asn Gly Thr Val Asp Glu Ile
                325                 330                 335
Ile Ser Ser Met Lys Leu Phe Gln Ser Asp Val Met Pro Phe Leu Lys
            340                 345                 350
Glu Lys Gln Arg Ser Leu Leu Tyr
        355                 360

SEQ ID NO 5
LENGTH: 324
TYPE: PRT
ORGANISM: Xenorhabdus luminescens

SEQUENCE: 5

Met Lys Phe Gly Leu Phe Phe Leu Asn Phe Ile Asn Ser Thr Thr Ile
1               5                   10                  15

Gln Glu Gln Ser Ile Ala Arg Met Gln Glu Ile Thr Glu Tyr Val Asp
            20                  25                  30

Lys Leu Asn Phe Glu Gln Ile Leu Val Cys Glu Asn His Phe Ser Asp
        35                  40                  45

Asn Gly Val Val Gly Ala Pro Leu Thr Val Ser Gly Phe Leu Leu Gly
    50                  55                  60

Leu Thr Glu Lys Ile Lys Ile Gly Ser Leu Asn His Val Ile Thr Thr
65                  70                  75                  80

His His Pro Val Arg Ile Ala Glu Glu Ala Cys Leu Leu Asp Gln Leu

-continued

```
                    85                  90                  95
Ser Glu Gly Arg Phe Ile Leu Gly Phe Ser Asp Cys Glu Arg Lys Asp
                100                 105                 110

Glu Met His Phe Asn Arg Pro Glu Gln Tyr Gln Gln Gln Leu Phe
            115                 120                 125

Glu Glu Cys Tyr Asp Ile Ile Asn Asp Ala Leu Thr Thr Gly Tyr Cys
        130                 135                 140

Asn Pro Asn Gly Asp Phe Tyr Asn Phe Pro Lys Ile Ser Val Asn Pro
145                 150                 155                 160

His Ala Tyr Thr Gln Asn Gly Pro Arg Lys Tyr Val Thr Ala Thr Ser
                165                 170                 175

Cys His Val Val Glu Trp Ala Ala Lys Lys Gly Ile Pro Leu Ile Phe
            180                 185                 190

Lys Trp Asp Asp Ser Asn Glu Val Lys His Glu Tyr Ala Lys Arg Tyr
        195                 200                 205

Gln Ala Ile Ala Gly Glu Tyr Gly Val Asp Leu Ala Glu Ile Asp His
    210                 215                 220

Gln Leu Met Ile Leu Val Asn Tyr Ser Glu Asp Ser Glu Lys Ala Lys
225                 230                 235                 240

Glu Glu Thr Arg Ala Phe Ile Ser Asp Tyr Ile Leu Ala Met His Pro
                245                 250                 255

Asn Glu Asn Phe Glu Lys Lys Leu Glu Glu Ile Ile Thr Glu Asn Ser
            260                 265                 270

Val Gly Asp Tyr Met Glu Cys Thr Thr Ala Ala Lys Leu Ala Met Glu
        275                 280                 285

Lys Cys Gly Ala Lys Gly Ile Leu Leu Ser Phe Glu Ser Met Ser Asp
    290                 295                 300

Phe Thr His Gln Ile Asn Ala Ile Asp Ile Val Asn Asp Asn Ile Lys
305                 310                 315                 320

Lys Tyr His Met

<210> SEQ ID NO 6
<211> LENGTH: 370
<212> TYPE: PRT
<213> ORGANISM: Xenorhabdus luminescens

<400> SEQUENCE: 6

Met Thr Ser Tyr Val Asp Lys Gln Glu Ile Thr Ala Ser Ser Glu Ile
  1               5                  10                  15

Asp Asp Leu Ile Phe Ser Ser Asp Pro Leu Val Trp Ser Tyr Asp Glu
             20                  25                  30

Gln Glu Lys Ile Arg Lys Lys Leu Val Leu Asp Ala Phe Arg His His
         35                  40                  45

Tyr Lys His Cys Gln Glu Tyr Arg His Tyr Cys Gln Ala His Lys Val
     50                  55                  60

Asp Asp Asn Ile Thr Glu Ile Asp Ile Pro Val Phe Pro Thr Ser
 65                  70                  75                  80

Val Phe Lys Phe Thr Arg Leu Leu Thr Ser Asn Glu Asn Glu Ile Glu
             85                  90                  95

Ser Trp Phe Thr Ser Ser Gly Thr Asn Gly Leu Lys Ser Gln Val Pro
            100                 105                 110

Arg Asp Arg Leu Ser Ile Glu Arg Leu Leu Gly Ser Val Ser Tyr Gly
        115                 120                 125

Met Lys Tyr Ile Gly Ser Trp Phe Asp His Gln Met Glu Leu Val Asn
```

-continued

```
            130                 135                 140
Leu Gly Pro Asp Arg Phe Asn Ala His Asn Ile Trp Phe Lys Tyr Val
145                 150                 155                 160

Met Ser Leu Val Glu Leu Leu Tyr Pro Thr Ser Phe Thr Val Thr Glu
                165                 170                 175

Glu His Ile Asp Phe Val Gln Thr Leu Asn Ser Leu Glu Arg Ile Lys
                180                 185                 190

His Gln Gly Lys Asp Ile Cys Leu Ile Gly Ser Pro Tyr Phe Ile Tyr
                195                 200                 205

Leu Leu Cys Arg Tyr Met Lys Asp Lys Asn Ile Ser Phe Ser Gly Asp
        210                 215                 220

Lys Ser Leu Tyr Ile Ile Thr Gly Gly Gly Trp Lys Ser Tyr Glu Lys
225                 230                 235                 240

Glu Ser Leu Lys Arg Asn Asp Phe Asn His Leu Leu Phe Asp Thr Phe
                245                 250                 255

Asn Leu Ser Asn Ile Asn Gln Ile Arg Asp Ile Phe Asn Gln Val Glu
                260                 265                 270

Leu Asn Thr Cys Phe Phe Glu Asp Glu Met Gln Arg Lys His Val Pro
        275                 280                 285

Pro Trp Val Tyr Ala Arg Ala Leu Asp Pro Glu Thr Leu Lys Pro Val
        290                 295                 300

Pro Asp Gly Met Pro Gly Leu Met Ser Tyr Met Asp Ala Ser Ser Thr
305                 310                 315                 320

Ser Tyr Pro Ala Phe Ile Val Thr Asp Asp Ile Gly Ile Ile Ser Arg
                325                 330                 335

Glu Tyr Gly Gln Tyr Pro Gly Val Leu Val Glu Ile Leu Arg Arg Val
                340                 345                 350

Asn Thr Arg Lys Gln Lys Gly Cys Ala Leu Ser Leu Thr Glu Ala Phe
        355                 360                 365

Gly Ser
    370

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:  SYNTHETIC
      OLIGONUCLEOTIDE

<400> SEQUENCE: 7
tacctaggga gaaagagaat g                                                     21
```

IN VIVO BIOSENSOR APPARATUS AND METHOD OF USE

CROSS-REFERENCE TO RELATED APPLICATION

This is a Continuation-In-Part of application Ser. No. 08/978,439 entitled Bioluminescent bioreporter integrated circuit filed Nov. 25, 1997, now U.S. Pat. No. 6,117,643 issued on Sep. 12, 2000.

The United States government has certain rights in the present invention pursuant to grant number R21RR14169-01 from the National Institutes of Health.

1.0 BACKGROUND OF THE INVENTION

1.1 Field of the Invention

The invention generally relates to the field of implantable diagnostic devices (i.e. devices deployed within the body of an animal) for monitoring one or more target substances, analytes, or metabolites in the animal. More particularly, the invention provides implantable biosensor devices for monitoring and regulating the level of analytes in the tissues and circulatory system of a human. In illustrative embodiments, the apparatus comprises a biosensor that is utilized to monitor the level of blood glucose in a diabetic or hypoglycemic patient. The disclosed sensors may also be used to control or regulate the delivery of a drug or other pharmaceutical agent from an external or an implantable drug delivery system. For example, the device may form part of an artificial pancreas to regulate insulin dosage in response to the level of glucose detected in situ.

1.2 Description of Related Art
1.2.1 Biosensors

Biosensors are hybrid devices combining a biological component with an analytical measuring element. The biological component reacts and/or interacts with the analyte(s) of interest to produce a response measurable by an electronic, optical, or mechanical transducer. The most common configurations presently available utilize immobilized macromolecules such as enzymes or antibodies to form the biological component. Examples of analytes and immobilized macromolecules include: glucose and immobilized glucose oxidase (e.g., Wilkins et al., 1995); nitrate and immobilized nitrate reductase (Wu et al., 1997); hydrogen peroxide and 2,3-dichlorophenoxyacetic acid and immobilized horseradish peroxidase (Rubtsova et al., 1998); and aspartate and immobilized L-aspartase (Campanella et al., 1995).

1.2.2 Whole-cell Biosensors

A further refinement for biosensors has been developed in recent years that utilizes intact living cells, such as a microorganism, or an eukaryotic cell or cell culture as an alternative to immobilized enzymes. Microbial cells are especially well suited for biosensor technologies; they are physically robust, capable of existing under extremely harsh and widely fluctuating environmental conditions, they possess an extensive repertoire of responses to their environment, and they can be genetically engineered to generate reporter systems that are highly sensitive to these environmental responses. Polynucleotide sequences that comprise specific promoter sequences are operably linked to a gene or a plurality of genes that encode the desired reporter enzyme(s) and then introduced into and maintained within the living cell. When the target analyte is present, the reporter genes are expressed, generating the enzyme(s) responsible for the production of the measured signal. Commonly used reporter systems have utilized either the β-galactosidase (lacZ) or catechol-2,3-dioxygenase (xylE) enzymes (Kricka, 1993).

Unfortunately, a limitation of these systems has been that following exposure to the target substance(s), the cells must be destructively lysed and the enzyme(s) isolated. This lysis is then followed by the addition of one or more secondary metabolites to yield a colorimetric signal that is proportional to the concentration of enzyme(s) in solution, providing a means to quantify the concentration of the original target substance.

A more recent improvement in such sensors utilizes green fluorescent protein as a reporter system, with the significant advantage that cells do not require destructive assay techniques to produce colorimetric signals. Because a substrate must be added to the green fluorescent protein constructs to first initiate the light response, however, these systems are quite complicated and offer little advantage for detection of analytes in situ (Prasher, 1995).

1.23 In Vivo Sensors

The development of an integrated in vivo implantable glucose monitor was first reported by Wilkins and Atanasov (1995). This system utilizes glucose oxidase immobilized within a micro-bioreactor. This enzyme catalyzes the oxidation of β-D-glucose by molecular oxygen to yield gluconolactone and hydrogen peroxide, with the concentration of glucose being proportional to the consumption of $O_2$ or the production of $H_2O_{hd\ 2}$. Unfortunately, the presence of a glucose oxidase inhibitor molecule in the human bloodstream tended to offset proportionality constants, and made the device unsatisfactorily inaccurate for precise glucose monitoring and control (Gough et al., 1997). Also limiting was the device's relatively large size ($\approx 5 \times 7$ cm), which negated its usefulness as an implantable device.

Although several smaller needle-type and microdialysis glucose sensors have since been developed to circumvent size limitations (Gough et al., 1997, Selam, 1997), their reliance on a glucose oxidase enzyme-based system limits their overall effectiveness and reliability.

Several nonspecific electrochemical sensors have also been investigated as potential in vivo glucose sensors (e.g., Yao et al., 1994; Larger et al., 1994), but problems including limited sensitivity, instability, and limited long-term reliability have prevented their wide-spread utilization (Patzer et al., 1995). According to Atanasov et al. (1997), continuously functioning implantable glucose biosensors with long-term stability have yet to be achieved.

1.3 Deficiencies in the Prior Art

Despite a significant miniaturization of biosensors during the past decade, they are still relatively large and obtrusive to serve as ideal implantable devices. Current methodologies using mammalian bioluminescent reporter cells require cell lysis and addition of an exogenous substrate to generate a measurable response. Consequently, these cells cannot serve as continuous on-line monitoring devices.

Therefore, there remains a need for the development of a small implantable monolithic (i.e. containing both biological and electrical components constructed on a single substrate layer) bioelectronic monitor that is durable, inexpensive, wireless, and that can communicate remotely to a drug delivery system to provide the controlled delivery of a therapeutic agent such as insulin.

2.0 SUMMARY OF THE INVENTION

The present invention overcomes these and other inherent limitations in the prior art by providing implantable apparatus and methods for detecting and quantitating particular analytes in the body of an animal. In particular, the invention provides devices for the in vivo detection and quantitation of metabolites, drugs, hormones, toxins, or microorganisms such as viruses in a human or animal. In illustrative embodiments, the invention provides a BBIC device useful for the detection of glucose in a human. Such devices provide for the first time an accurate on-line detector for glucose monitoring, and offer the ability to control the administration of pharmaceutical agents via an external or implantable drug delivery system. Also disclosed are BBIC devices for detecting the concentration of signature molecules (i.e. proteins released from cancer cells, etc.), clotting factors, enzymes and the like, and other analytes present in the bloodstream or interstitial fluid. In the area of oncology, the biosensor devices find utility in both initial and remission monitoring, on-line measurement of the effectiveness of chemotherapy, and stimulation/activity of the immune system. Likewise, the biosensor devices are useful in other areas of medicine, including on-line monitoring for enzymes associated with the occurrence of blood clots (strokes, heart attacks, etc.), detection and quantitation of clotting factors (maintain level), hormone replacement, continuous drug monitoring (testing for controlled substances in prisoners, military personnel, etc.), monitoring of soldiers exposure to sub-lethal exposure to nerve agents and other debilitating agents, monitor levels of compounds affecting mental illness, and the like.

In one embodiment there is provided an implantable monolithic bioelectronic device for detecting an analyte within the body of an animal. In a general sense this device comprises a bioreporter that is operably positioned above a substrate that is on an integrated circuit. The bioreporter is capable of metabolizing the target analyte and emits light consequent to this metabolism when in contact with the analyte. The device further comprises a sensor closely positioned to the integrated circuit that detects the emitted light and generates an electrical signal in proportion to the amount of light generated by the bioreporter. Preferably the entire implantable device is contained within a biocompatible container that is implanted within the body of the animal in which the analyte detection is desired.

The biocompatible container may be comprised of silicon nitride, silicon oxide, or a suitable polymeric matrix, with exemplary matrices such as polyvinyl alcohol, poly-L-lysine, and alginate being particularly preferred. The polymeric matrix may also further comprise a microporous, mesh-reinforced or a filter-supported hydrogel.

In certain embodiments, it may also be desirable to provide a transparent, biocompatible, bioresistant separator that is operably positioned between the phototransducer and the bioreporter.

The bioreporter preferably comprises a plurality of eukaryotic or prokaryotic cells that produce a bioluminescent reporter polypeptide in response to the presence of the target analyte. Prokaryotic cells such as one or more strains of bacteria, and eukaryotic cells such as mammalian cells are particularly preferred. Exemplary mammalian cells are human cells such as islet β-cells, immortal stem cells, or hepatic cells, with immortal stem cells being particularly preferred.

These cells preferably comprise one or more nucleic acid segments that encode a luciferase polypeptide or a green fluorescent protein that is produced by the cells in response to the presence of the analyte. Preferably the nucleic acid segment encodes an *Aqueorea Victoria*, *Renilla reniformis*, or a humanized green fluorescent protein, or more preferably, a bacterial Lux polypeptide, such as the LuxA, LuxB, LuxC, LuxD, or LuxE polypeptide, or the LuxAB or LuxCDE fused polypeptides described herein.

Exemplary bacterial lux gene sequences that may be employed to prepare the genetic constructs include the Vibrio fischerii or more preferably, the *Xenorhabdus luminescens* luxA, luxB, luxC, luxD, luxE, luxAB, or luxCDE genes.

Exemplary lux gene sequences that may be employed for preparation of the genetic constructs as described herein include the gene sequences disclosed in SEQ ID NO:1. Exemplary Lux polypeptide sequences are disclosed in SEQ ID NO:2, SEQ ID NO:3, SEQ ID NO:4, SEQ ID NO:5 and SEQ ID NO:6.

The Lux polypeptides preferably comprise at least a 10 contiguous amino acid sequence from one or more of the polypeptide sequences disclosed in SEQ ID NO:2 through SEQ ID NO:6. More preferably the Lux polypeptides comprise at least a 15 contiguous amino acid sequence from one or more of the polypeptide sequences disclosed in SEQ ID NO:2 through SEQ ID NO:6, and more preferably still, comprise at least a 20 contiguous amino acid sequence from one or more of the polypeptide sequences disclosed in SEQ ID NO:2 through SEQ ID NO:6.

Such polypeptides are preferably encoded by a nucleic acid sequence that comprises at least 20, at least 25, at least 30, at least 35, at least 40, or at least 45 or more contiguous nucleotides from SEQ ID NO:1.

The expression of the Lux-encoding nucleic acid segments is preferably regulated by a nucleic acid regulatory sequence operably linked to the Lux-encoding segment. Preferably this regulatory sequence comprises a cis-acting element that is responsive to the presence of the target analyte. Exemplary cis-acting response elements are selected from the group consisting of an S14 gene sequence, a hepatic L-pyruvate kinase gene sequence, a hepatic 6-phosphofructo-2-kinase gene sequence, a β-islets insulin gene sequence, a mesangial transforming growth factor-β gene sequence, and an acetyl-coenzyme-A carboxylase gene sequence.

In an illustrative embodiment, the cis-acting response element comprises a contiguous nucleotide sequence from a β-islets insulin gene sequence or a hepatic L-pyruvate kinase gene sequence. Expression of the nucleic acid sequence is preferably regulated by a promoter sequence such as the one derived from an L-pyruvate kinase-encoding gene described herein.

The device may further comprise a wireless transmitter, an antenna, and a source of nutrients capable of sustaining the bioreporter cells. Likewise the biocompatible container enclosing the bioreporter may further comprise a membrane that is permeable to the analyte but not to the bioreporter cells themselves. Such a semi-permeable membrane permits analytes to flow freely from the bodily fluid into the detector device, but restricts the migration of bioreporter cells from the device into the surrounding tissues or circulatory system of the body in which the device is implanted.

In one embodiment, the integrated circuit is a complementary metal oxide semiconductor (CMOS) integrated circuit. The integrated circuit may comprise one or more phototransducer, that themselves may be comprised of one or more photodiodes. Likewise, the integrated circuit may also further comprise a photodiode, a current-to-frequency converter, a digital counter, and/or a transmitter that is capable of transmitting either digital or analog data.

The invention also provides an implantable controlled drug delivery system that comprises both the bioluminescent bioreporter integrated circuit (BBIC) device and an implantable drug delivery pump that is capable of being operably controlled by the BBIC and that is capable of delivering the drug to the body of the animal in response to controls by the device. The invention also concerns a method of providing a controlled supply of a drug to a patient in need thereof. The method generally involves implanting within the body of the patient the controlled drug delivery system.

The invention also provides a method of determining the amount of a drug required by a patient in need thereof, such as in the case of giving a diabetic patient an appropriate amount of insulin. The method generally involves implanting within the body of the diabetic patient one or more BBIC devices that are responsive to either glucose, glucagons, insulin, or another glucose metabolite, and determining the amount of insulin required by the patient based upon the levels of the analyte detected in the body fluids by. the device. When the device indicates that higher levels of insulin are required, the appropriate control signal can be sent to the drug delivery system and more insulin is injected into the body. When the device indicates that lower levels of insulin are required, then the appropriate control signal can be sent to the drug delivery system and less insulin can be administered. Such "real-time" monitoring of glucose in the body of the animal permits for controlled release of insulin throughout the day, and obviates the need for daily or more frequent injections of insulin that may either be too much or too little for the particular time of administration. This affords a more cost-effective administration of the drug, and also provides a more stable dosing of the insulin to the patient on an "as needed" basis.

The invention also provides a kit for the detection of an analyte, and such kits generally will include one or more of the disclosed BBIC devices in combination with appropriate instructions for using the detection device. Such kits may also routinely contain one or more standardized reference solutions for calibrating the device, and may also include suitable storage or nutrient medium for sustaining the bioreporter cells either during storage or during use once implanted within the body of the animal. In the case of therapeutic kits, such kits will also generally include one or more controlled delivery systems for administration of the drug to the body of the animal.

The invention also provides a method of regulating the blood glucose level of an animal in need thereof. This method generally comprises monitoring the level of glucose in the bloodstream or interstitial fluid of the patient using the BBIC device, and administering to the patient an effective amount of an insulin composition sufficient to regulate the blood glucose level.

This new type of bioluminescence-based bioreporter is capable of monitoring target substances without the disadvantageous requirement that cells be destroyed to produce the measurable signal. This allows for monitoring to occur continuously, on-line and in real-time (Simpson et al., 1998a, 1998b). These cells rely on luciferase genes (designated lux in prokaryotes and luc in eukaryotes) for the reporter enzyme system. U.S. patent application Ser. No. 08/978,439 and Intl. Pat. Appl. Ser. No. PCT/US98/25295 (each of which is specifically incorporated herein by reference in its entirety) disclose a self-contained miniature bioluminescence bioreporter integrated circuit ("BBIC") that was designed to detect specific molecular targets ex situ or ex vivo.

The present invention concerns an implantable, or an in situ or an in vivo BBIC device that is capable of being implanted within the body of an animal, and that is capable of detecting the concentration of one or more analytes present within the animal. The implantable monolithic bioelectronic device of the present invention generally comprises a substrate, a bioreporter capable of responding to a particular substance by the emission of light, a container affixed to the substrate capable of holding the bioreporter, an integrated circuit on the substrate including a phototransducer operative to generate an electrical signal in response to the light wherein the signal indicates the concentration of the substance; and a biocompatible housing that is capable of being implanted within the body of an animal, with that portion of the housing covering the bioreporter container comprising a semi-permeable membrane that permits passage of the analyte from the body of the animal to contact the biosensor, but restricts the bioreporter molecules from diffusing into the body of the animal that contains the implanted device. The bioreporter may be in solution, that is a cell suspension, and entrapped in the container by the semi-permeable membrane, or alternatively the bioreporter may be encapsulated in a selectively permeable polymer matrix that is capable of allowing the selected substance in solution reach the bioreporter. Preferably, the matrix is optically clear.

The apparatus may further comprise a layer of bioresistant/biocompatible material between the substrate and the container, such a layer of silicon nitride. The integrated Circuit is preferably a CMOS integrated circuit, and the phototransducer is preferably a photodiode.

The integrated circuit may also include a current to frequency converter and/or a digital counter. Additionally, the integrated circuit may also include one or more transmitters. Such transmitters may be wireless, or conventionally wired. In preferred embodiment, the apparatus also includes a drug delivery device capable of receiving transmissions from the transmitter.

A further embodiment of the invention is an implantable apparatus for detecting a selected substance in solution, which comprises an integrated circuit including a phototransducer adapted to input an electrical signal into the circuit in response to light, a bioreporter capable of responding to selected substance in solution by emitting light, the reporter adapted to contact the substance; and a transparent, biocompatible, and bioresistant separator positioned between the phototransducer and the bioreporter to enable light emitted from the bioreporter to strike the phototransducer. In a preferred embodiment of the present invention, the selected substance is glucose. The bioreporter may be a mammalian cell that contains a nucleotide sequence that encodes one or more luminescent reporter molecules. Such a nucleotide sequence may comprise one or more lux genes. In a preferred embodiment the lux genes comprise both luxCDE genes and fused luxAB genes. In one embodiment, these lux genes are derived from *Xenorhabdus luminescens*. The lux genes may be regulated by a nucleic acid sequence comprising one or more cis-acting glucose response elements. In an illustrative embodiment, the glucose response element may be derived from the β-islets or hepatic L-pyruvate kinase gene. In a highly preferred embodiment the p.LPK.Luc$_{FF}$ plasmid is used to provide one or more glucose response elements and the L-pyruvate kinase promoter to drive the expression of one or more lux genes. The cells constituting the bioreporter may be in suspension, entrapped in place on the IC by a semi-permeable membrane. Alternatively the cells constituting the bioreporter may be encapsulated in a polymer matrix affixed to IC. Such a matrix may be permeable to the selected substance in solution.

A further embodiment of the invention concerns an implantable monolithic bioelectronic device for detecting a selected substance in body fluid. This device generally comprises a biocompatible housing; a bioreporter capable of responding to a selected substance by emitting; and, a sensor capable of generating an electrical signal in response to the reception of the emitted light. Such a device may also include a transparent, bioresistant and biocompatible separator positioned between the bioreporter and the sensor and a semi-permeable membrane positioned in the biocompatible housing so that the selected substance can access the bioreporter.

A standard integrated circuit (IC) is coated with a layer of insulating material such as silicon dioxide or silicon nitride. This process is called passivation and serves to protect the surface of the chip from moisture, contamination, and mechanical damage. BBICs require a second coating that must be biocompatible and bioresistant, must protect the OASIC from chemical stresses, must be optically tuned to efficiently transmit the light from the material under test, must adhere to an oxide coating, must be pin-hole free, and must be able to be patterned in order to form openings over the bonding pads and whatever structures that might be needed to maintain the bioreporter or collect a sample.

The present invention contemplates that the components of the biosensor may be packaged in kit form. Kits may comprise, in suitable container means, one or more bioreporters and an integrated circuit including a phototransducer. Kits may further comprise a drug delivery device.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. Illustrative embodiments of the present invention are depicted in the drawings, with like numerals being used to refer to like and corresponding parts of the various drawings.

FIG. 10A shows a schematic representation of an implantable biosensor containing two separate photodetectors with the bioreporters responding to either an increase or decrease in glucose concentrations.

4.0 DESCRIPTION OF ILLUSTRATIVE EMBODIMENTS

Figure 1:
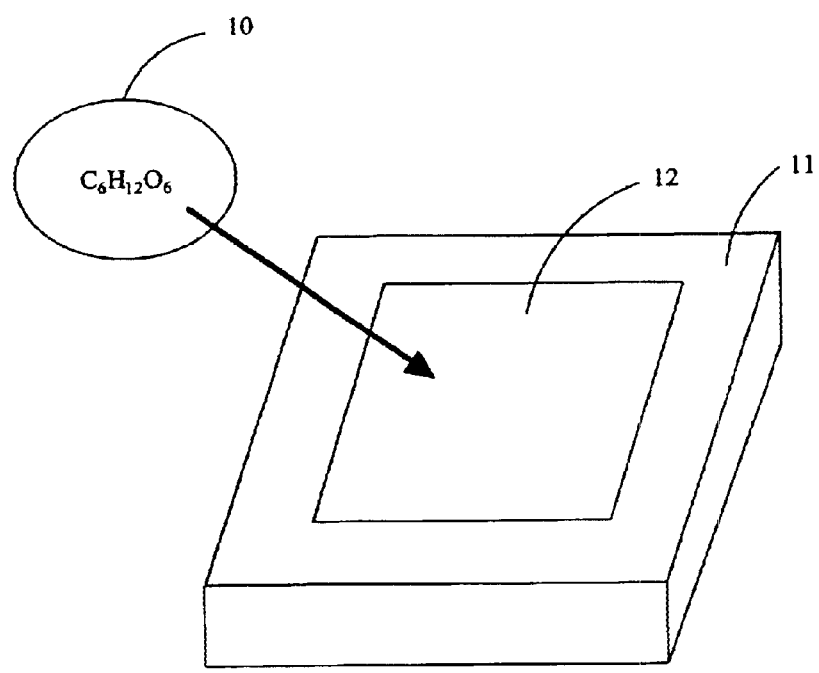
FIG. 1 shows a perspective view of one illustrative embodiment of the invention.

The luciferase system has been adapted for use in biosensors in vivo. In prokaryotes, the lux system consists of a luciferase composed of two subunits coded for by the genes luxA and luxB that oxidize a long chain fatty aldehyde to the corresponding fatty acid resulting in a blue-green light emission at an approximate wavelength of 490 nm (Tu and Mager, 1995). The system also contains a multienzyme fatty acid reductase consisting of three proteins, a reductase encoded by luxC, a transferase encoded by luxD, and a synthetase encoded by luxE that convert and recycle the fatty acid to the aldehyde substrate. The genes are contained on a single operon, allowing for the cloning of the complete lux gene cassette downstream from user-specific promoters for the utilization of bioluminescence to monitor gene expression. The majority of bioluminescent bioreporters consist of Gram-negative organisms engineered to detect and monitor critically important chemical and environmental stressors (Ramanathan et al., 1997, Steinberg et al., 1995). Luciferase fusions in Gram-positive bacteria, as well as in yeast cell lines, are also being successfully performed (Andrew and Roberts, 1993, Srikantha et al., 1996).

Eukaryotic luciferase genes cloned into bacterial reporters include the firefly luciferase (luc) producing light near 560 nm and the click beetle luciferase (lucOR) emitting light near 595 nm (Cebolla et al., 1995, Hastings, 1996). Eukaryotic bioreporters have been designed to monitor glucose concentrations in rat islet β-cells (Kennedy et al., 1997), steroid activity in HeLa cells (Gagne et al., 1994), ultraviolet light effects in mouse fibroblast cells (Filatov et al, 1996), toxicity effects in human liver cancer cells (Anderson et al., 1995), estrogenic and antiestrogenic compounds in breast cancer cell lines (Demirpence et al., 1995), and erythropoiten gene induction in human hepatoma cell lines (Gupta and Goldwasser, 1996). To date, most eukaryotic bioluminescent reporters require cell destruction and the addition of an exogenous substrate, usually luciferin, to generate a measurable luminescent response.

Green fluorescent protein ("GFP") is also routinely used as a reporter system, with the significant advantage that cells do not require destructive assay techniques to produce colorimetric signals (Hanakam et al., 1996; Grygorczyk et al., 1996; Siegel and Isacoff, 1997; Biondi et al., 1998). However, a substrate must be added to the GFP constructs to first initiate the light response (Prasher, 1995). Humanized GFP cDNA has been developed which is specifically adapted for high-level expression in mammalian cells, especially those of human origin (Zolotukhin 1996). Humanized GFP can be efficiently inserted into mammalian cells using viral vectors (Levy et al., 1996; Gram et al., 1998).

Detection of the bioluminescent signal from the reporter organisms is achieved through the use of optical transducers, including photomultiplier tubes, photodiodes, microchannel plates, photographic films, and charge-coupled devices. Light is collected and transferred to the transducer through lenses, fiber optic cables, or liquid light guides. However, applications requiring small volumes, remote detection, or multiple parallel sensing necessitate a new type of instrumentation that is small and portable, yet maintains a high degree of sensitivity.

4.1 Overview of the System

The present invention describes an implantable BBIC that detects selected substances. The bioreporter is a genetically engineered cell line in which the nucleic acid sequence contains a cis-activating response element that is responsive to the selected substance. In preferred embodiments, the selected substance is glucose. Exposure of the bioreporter to the selected substances causes the response element to up-regulate a nucleic acid sequence that encodes one or more polypeptides that generate a luminescent response. In a preferred embodiment, the luminescent response is generated by a prokaryotic lux system.

The function of the IC portion of the BBIC is to detect, filter, amplify, digitize, and report the bioluminescent signal. In effect, the IC serves as a complete laboratory instrument-on-a-chip: a microluminometer.

Silicon-based ICs can detect optical signals in the near ultraviolet, visible, and near infrared regions using the PN junctions normally used to form transistors (Simpson et al., 1999a). Using an n-well/p-substrate photodiode in a 0.5-$\mu$m bulk CMOS IC process, an ~66% quantum efficiency has been measured at the 490-nm bioluminescent wavelength (Simpson et al., 1999b). A variety of signal-processing schemes can be employed. However, counting the pulses from a current-to-frequency converter circuit forms a long time-constant integrator and is the causal portion of the matched filter for a low-level bioluminescent signal in white noise. Using the photodiode mentioned above with this signal-processing scheme, an rms noise level of 175 electrons/second was measured for a 13-minute integration time, corresponding to a detection limit of ~500 photons/second (Simpson et al., 1999b).

Figure 6:
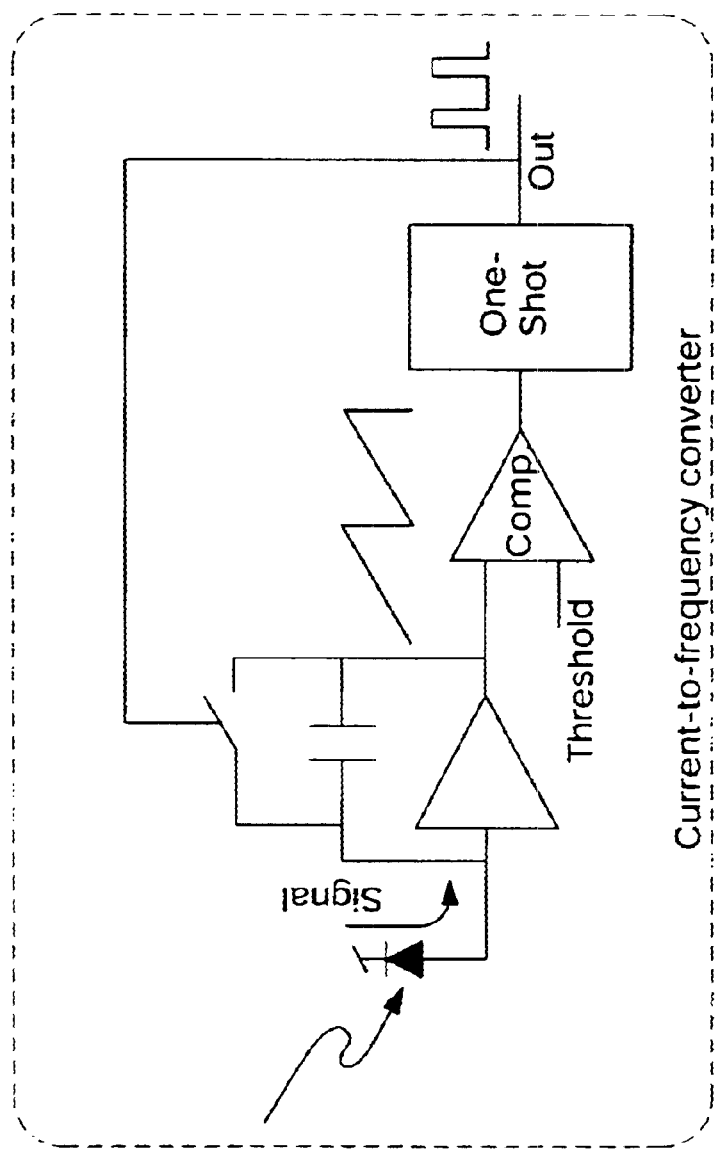
FIG. 6 shows the current-to-frequency converter architecture of the apparatus.
Figure 7:
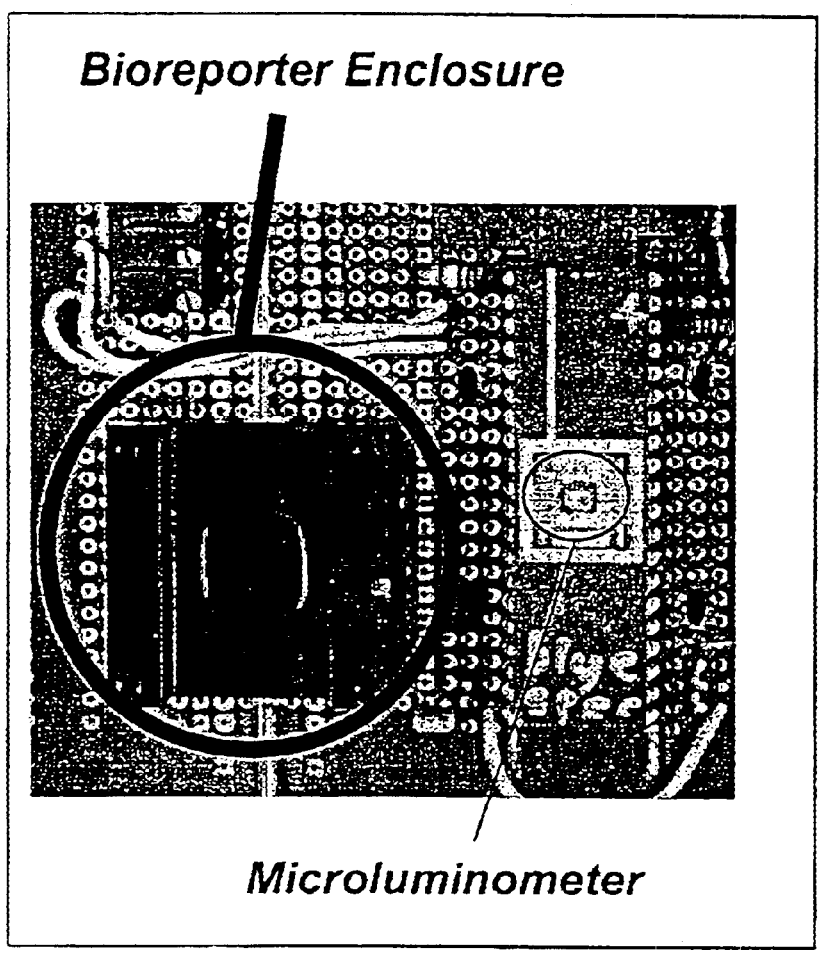
FIG. 7 shows a prototype BBIC biosensor.

A prototype BBIC was constructed by placing the toluene sensitive bioreporter, P. putida TVA8, above a custom integrated microluminometer. FIG. 6 shows the prototype BBIC (including the bioreporter enclosure) as used in the characterization studies (Simpson et al., 1998b: Simpson et al., 1998c; Simpson et al., 1998d).

With no luminescent signal coming from the cells, multiple measurements were taken with the integration time set to 1-minute. Leakage currents produced a signal of ~6 counts/minute with a standard deviation ($\sigma$) of 0.22 counts/minute. As expected, the $\sigma$ decreased with the square root of the integration time. Longer integration times were produced off-line by summing 1-minute measurements.

Figure 8:
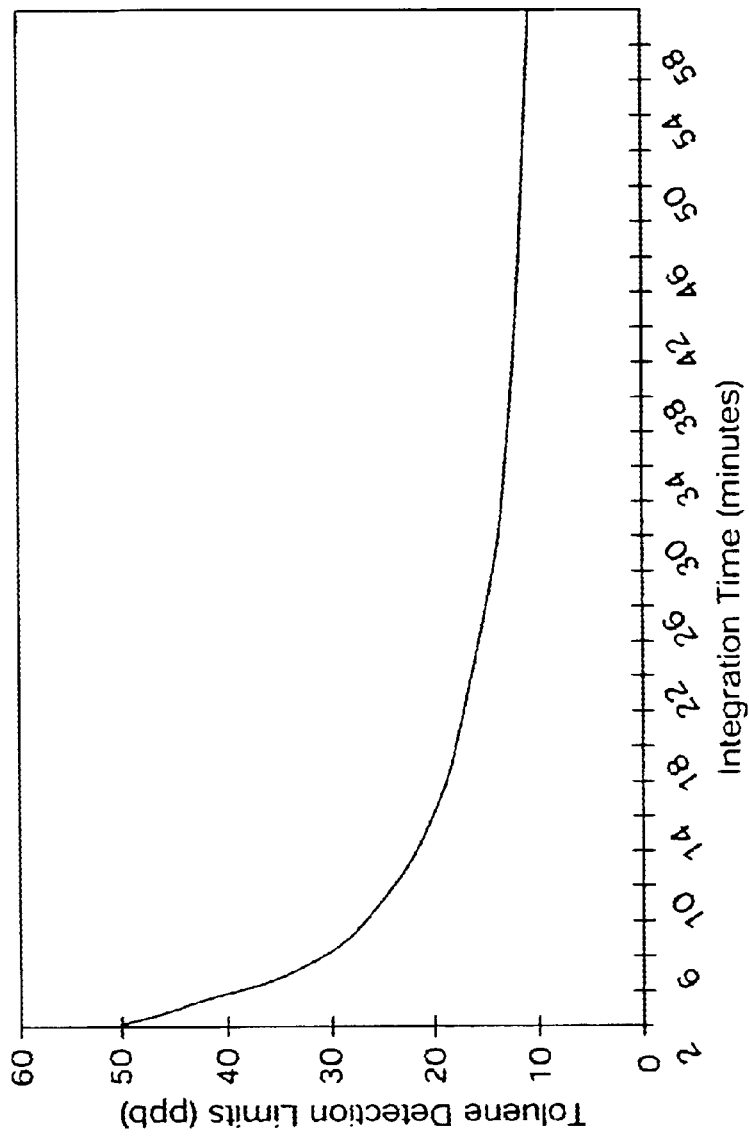
FIG. 8 shows a minimum detectable concentration of toluene as a function of integration time for the prototype BBIC employing the bioreporter Pseudomonas putida TVA8.

Bioluminescence was induced in the BBIC cells and a control sample of cells by exposure to toluene vapor. From the control sample measurements, we estimate that the toluene concentration was no more than 1 ppm. A signal of 12 counts/minute (6 counts/minute above background) was measured. From previous measurements, P. putida TVA8 is known to have a linear response to toluene concentration until saturating when the concentration reaches a level of approximately 10 ppm. The minimum detectable toluene concentration for this BBIC as a function of integration time is shown in FIG. 8. In general, the minimum detectable concentration is also a function of the number of bioreporter cells and the area of the photodiode.

A naphthalene-sensitive BBIC was produced using the microluminometer described above and the bioreporter P. fluorescens 5RL. Using the same experimental procedure described above, this BBIC was exposed to naphthalene vapor with a concentration of approximately 10 ppm. A signal of 240 counts/minute was recorded.

To eliminate the need for the addition of exogenous substrate, cells must themselves supply the appropriate substrate for the luciferase. In the bacterial system the substrate is generated by a fatty acid reductase complex coded for by the luxCDE genes. This enzyme complex reduces short chain fatty acids to the corresponding aldehyde. The luciferase then oxidizes the aldehyde to the corresponding fatty acid. The preferred fatty acid for this reaction is myristic acid, which is present in eukaryotic organisms (Rudnick et al., 1993). Myristic acid is usually involved in the myristoylation of the amino terminus that is associated with membrane attachment (Borgese et al., 1996, Brand et al., 1996).

In a preferred embodiment, the bioreporter for glucose monitoring will be a mammalian bioluminescent reporter cell line that has been genetically engineered to express luminescence in response to glucose concentrations on a continuous basis, without the need for cell destruction and exogenous substrate addition. Current methodologies using mammalian bioluminescent reporter cells require cell lysis and addition of an exogenous substrate to generate a measurable response. Consequently, these cells cannot serve as continuous on-line monitoring devices. In a preferred embodiment, this new cell line is constructed with a bioluminescent reporter utilizing the luxAB and luxCDE genes from X. luminescens incorporated into a plasmid-based system designated p.LPK.Luc$_{FF}$ which contains a eukaryotic luc gene able to respond to glucose concentrations. Replacement of the luc gene with the luxAB gene will allow for bioluminescence measurements to occur in real-time with glucose concentrations, negating the requirement for cell destruction and substrate addition.

To form an implantable, glucose-monitoring BBIC, the bioreporters may be entrapped in a container behind a semi-permeable membrane that keeps them in place over the IC photodetector. Alternatively the bioreporter may be encased in a polymer matrix. The BBIC is enclosed in a biocompatible housing with a semi-permeable membrane covering the bioreporter region. This membrane allows glucose to pass to the bioreporters, yet stops the passage of larger molecules that could interfere with the glucose measurement. When the glucose reaches the bioreporter, it is metabolized and the cells emit visible light. The IC detects this light, amplifies and filters this signal, and then reports this measurement. This measurement could be reported to the patient (e.g., to a wristwatch receiver) or could be reported to an insulin pump in a closed-loop system that functions much like the pancreas.

FIG. 1 shows a perspective view of the present invention. Glucose 10 that is being detected enters the BBIC 11 through the semi-permeable membrane 12 that covers the bioreporter.

Figure 2:
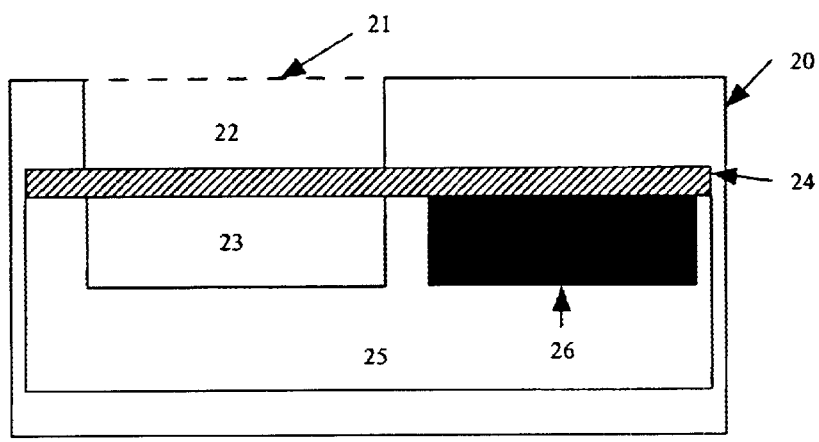
FIG. 2 shows a side view of an illustrative embodiment of the present invention.

FIG. 2 shows a side view of the present invention. The BBIC is enclosed in a biocompatible housing 20 with a semi-permeable membrane 21 covering the bioreporter held in a container 22. The cells constituting the bioreporter may be in suspension or encapsulated in a polymer matrix. The bioreporter is separated from a photodetector 23 by a protective coating 24. A single substance 25 contains the photodetector as well as additional circuits 26 that process and transmits the signal.

Figure 3:
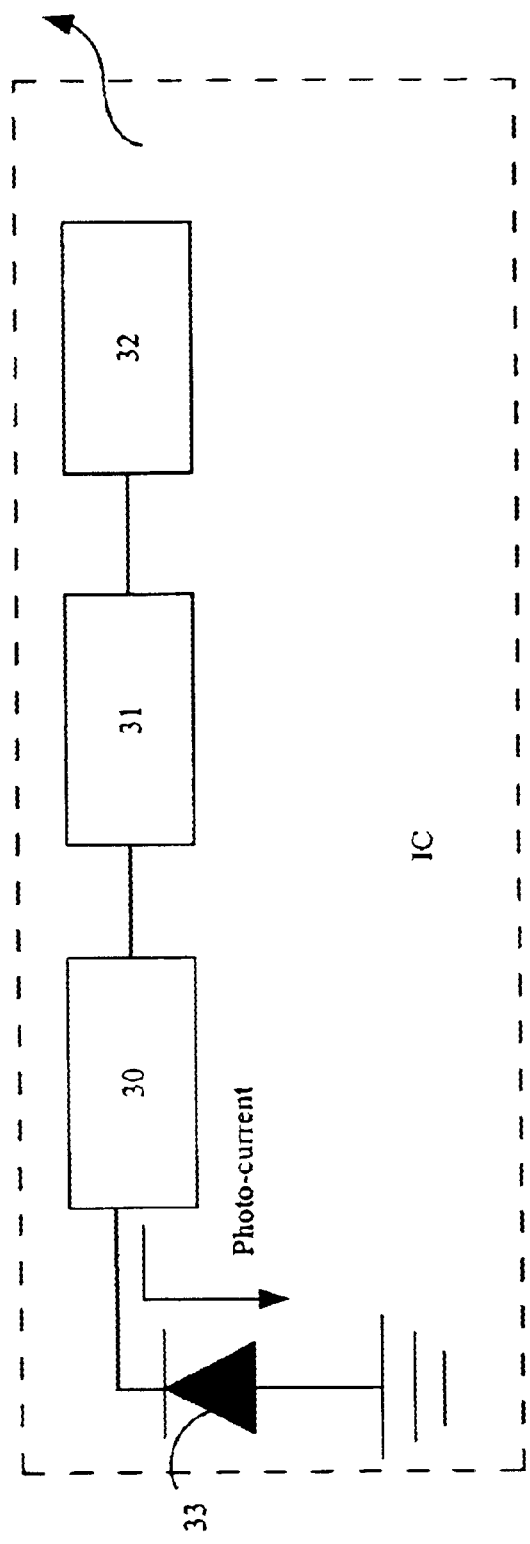
FIG. 3 shows a block diagram of an illustrative embodiment of the integrated circuit.

FIG. 3 shows a block diagram of one embodiment of the integrated circuit ("IC"). The photodetector is a photodiode 33 connected to a current to frequency converter 30. The photodiode responds to light by sinking a current. The current is converted to a series of pulses that are accumulated in a digital counter 31. The number of counts in the counter in a fixed amount of time is directly proportional to the amount of light collected by the photodiode, which is directly proportional to the concentration of glucose. Digital processing circuitry in the digital counter would determine the appropriate next step for an insulin pump based on the measured glucose levels. The measured concentration or next instruction for the insulin pump could be reported via the wireless transmitter 32. All these circuits (photodiode, signal processing, and wireless transmission) can be fabricated on one IC.

Figure 4:
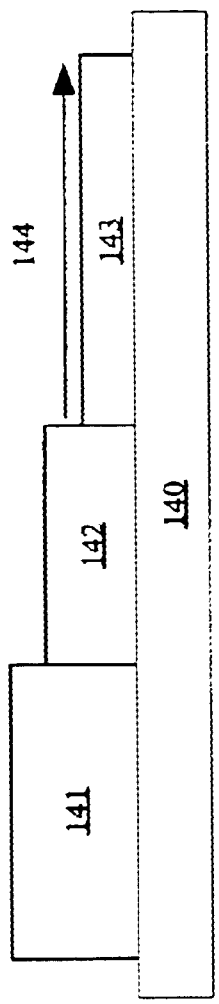
FIG. 4A shows a high-quality photodetector that can be made using a standard N-well CMOS process.
FIG. 4B shows two photodetector structures fabricated in a silicon-on-insulator CMOS process: on the left, a lateral PIN detector; on the right, a device similar to left except that the junction is formed with a Schottky junction.

FIG. 4 shows the bioreporter being supplied with water and nutrients. A fluid and nutrient reservoir 141 is connected to a microfluidic pump 142 so that nutrient and fluid 144 may flow through the polymer matrix 143 enclosing the bioreporter. Each of these components can be constructed on a single substrate 140.

Figure 4A:
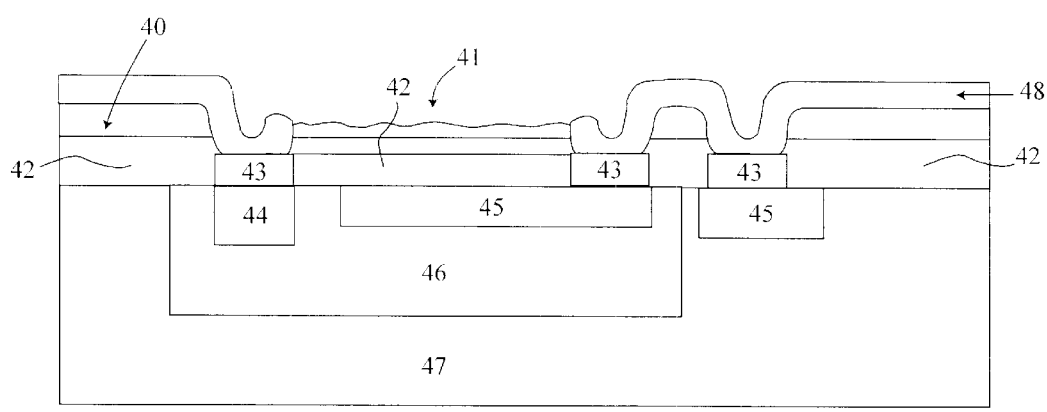

FIG. 4A shows a high-quality photodetector made using a standard N-well CMOS process. The photodetector consists of two reverse biased diodes in parallel. The top diode is formed between the P+ active layer 45 and the N-well 46, and the bottom diode is formed between the N-well 46 and the P-substrate 47. The top diode has good short wavelength light sensitivity (400–550 nm), while the bottom diode provides good long wavelength sensitivity (500–1100 nm). Thus, the complete diode is sensitive over the range from 400 to 1100 nm. The luminescent compound under test 41 is separated from the photodetector by a layer 40 of $Si_3N_4$ and a layer 42 of $SiO_2$.

Figure 10B:
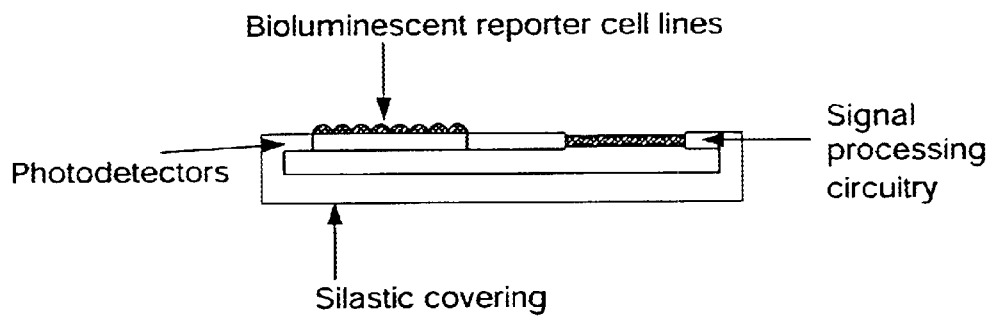
FIG. 10B shows a side view of biosensor showing silastic covering.
Figure 10C:
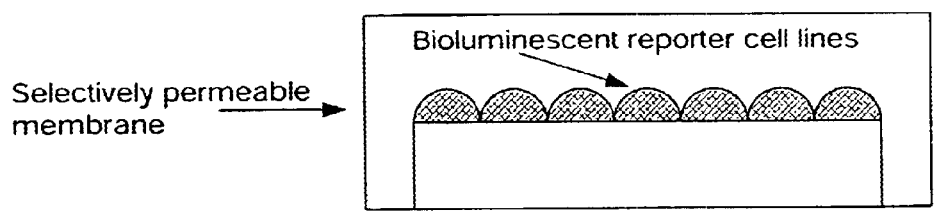
FIG. 10C shows a schematic representaion of the utilization of a selectably permeable membrane to protect bioreporters from the immune response.

FIG. 10A, FIG. 10B, and FIG. 10C show schematic representations of an implantable biosensor containing two separate photodetectors with the bioreporters responding to either an increase or decrease in glucose concentrations.

FIG. 10B shows a side view of biosensor showing silastic covering.

FIG. 10C shows a schematic representaion of the utilization of a selectably permeable membrane to protect bioreporters from the immune response.

4.2 Photodetector

The first element in the micro-luminometer signal processing chain is the photodetector. The key requirements of the photodetector are:
- Sensitivity to wavelength of light emitted by the bioluminescent or chemiluminescent compound under test;
- Low background signal (i.e. leakage current) due to parasitic reverse biased diodes;
- Appropriate coating to prevent the materials in the semiconductor devices from interfering with the bioluminescent or chemiluminescent process under study and to prevent the process under study from degrading the performance of the micro-luminometer; and,
- Compatibility with the fabrication process used to create the micro-luminometer circuitry.

Two photodetector configurations that satisfy these requirements are described below. It should be understood, however, that alternative methods of constructing such a photodetector can be used by one skilled in the art without departing from the spirit and scope of the invention as defined in the claims.

In the first embodiment, the photodetector is fabricated in a standard N-well CMOS process. Shown in FIG. 5A, this detector is formed by connecting the PN junction between the PMOS active region and the N-well in parallel with the PN junction between the N-well and the P-type substrate. The resulting detector is sensitive to light between approximately 400 nm and approximately 1100 nm, a range that encompasses the 450 to 600 nm emission range of most commonly used bioluminescent and chemiluminescent compounds or organisms. In order to meet the requirement that the device have a low background signal, the device is operated with a zero bias, setting the operating voltage of the diode equal to the substrate voltage. The photodiode coating may be formed with a deposited silicon nitride layer or other material compatible with semiconductor processing techniques.

In the second photodetector embodiment, the detector is fabricated in a silicon-on-insulator (SOI) CMOS process. The internal leakage current in an SOI process is two to three orders of magnitude lower than in standard CMOS due to the presence of a buried oxide insulating layer between the active layer and the substrate. Two photodetector structures are envisioned in the SOI process. The first structure, shown on the left of FIG. 5B, consists of a lateral PIN detector where the P-layer is formed by the P+ contact layer, the I (intrinsic) region is formed by the lightly doped active layer, and the N region is formed by the N+ contact layer of the SOI CMOS process. The spectral sensitivity of this lateral detector is set by the thickness of the active layer, which may be tuned for specific bioluminescent and chemiluminescent compounds.

Figure 4B:
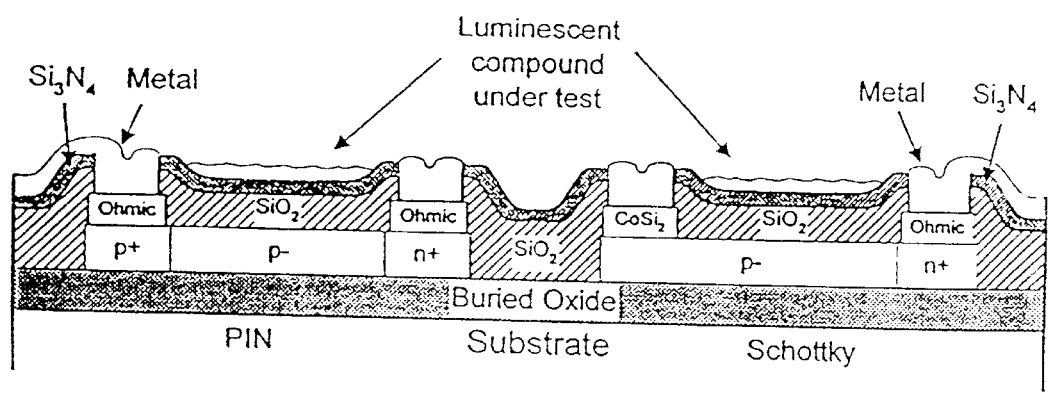

The second structure, shown on the right side of FIG. 4B, is similar to the first except that the junction is formed with a Schottky junction between a deposited cobalt silicide ($CoSi_2$) or other appropriate material layer and the lightly doped active layer.

The inventors contemplate that other photodetector configurations may be envisioned in silicon or other semicoductor processes meeting the criteria set forth above.

4.3 Low Noise Electronics

The low noise electronics are the second element in the micro-luminometer signal processing chain. The requirements for the low noise electronics are:
- Sensitivity to very low signal levels provided by the photodetector;
- Immunity to or compensation for electronic noise in the signal processing chain;
- Minimum sensitivity to variations in temperature;
- Minimum sensitivity to changes in power supply voltages (for battery powered applications);
- For some applications the electronics must have sufficient linearity and dynamic range to accurately record the detected signal level; and,
- In other applications the electronics must simply detect the presence of a signal even in the presence of electronic and environmental noise.

Three embodiments that satisfy these requirements are described below. It should be understood, however, that alternative methods of detecting small signals while satisfying these requirements may be used without departing from the spirit and scope of the invention as defined in the claims.

Figure 5A:
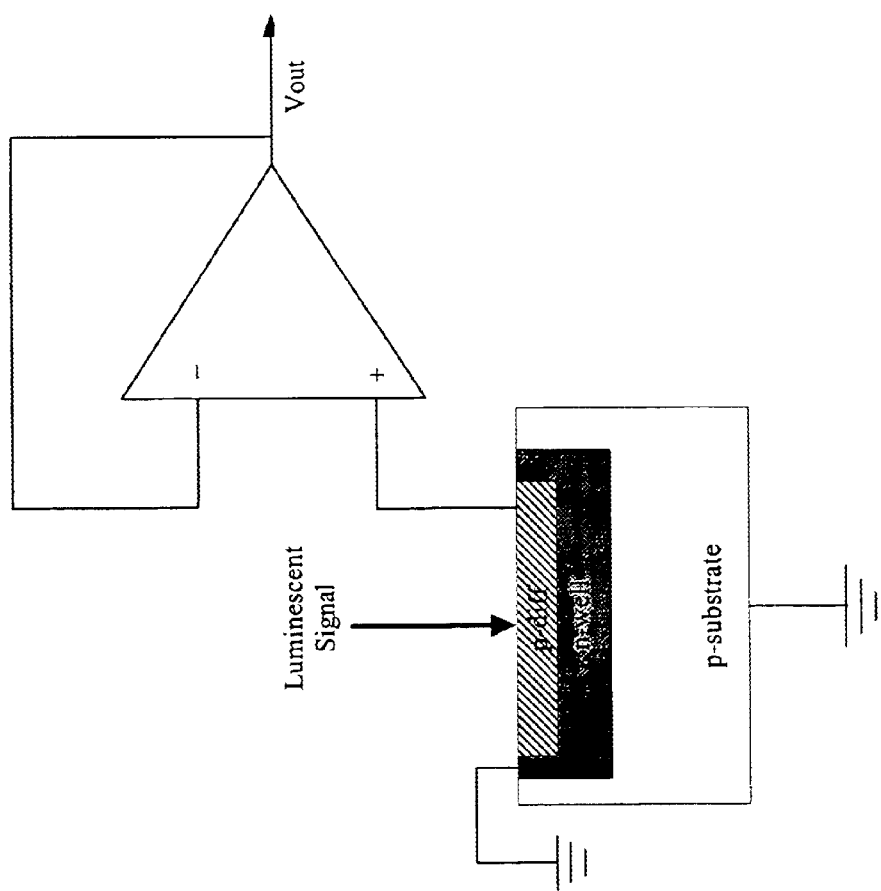
FIG. 5A shows a simple photodiode consisting of a P-diffusion layer, an N-well, and a P-substrate.

FIG. 5A schematically shows the first approach to the detection of very small signals. This device uses a P-diffusion/N-well photodiode, a structure compatible with standard CMOS IC processes, in the open circuit mode with a read-out amplifier (fabricated on the same IC with the photodiode). The luminescent signal generates electron-hole pairs in the P-diffusion and the N-well. The photo-generated electrons in the P-diffusion are injected into the N-well, while the photo-generated holes in the N-well are injected into the P-diffusion. The N-well is tied to ground potential so that no charge builds up in this region. However, since the P-diffusion is only attached to the input impedance of a CMOS amplifier (which approaches infinity at low frequencies), a positive charge collects in this region. Thus, the voltage on the P-diffusion node begins to rise.

As the P-diffusion voltage begins to rise, the P-diffusion/N-well photodiode becomes forward biased, thereby producing a current in a direction opposite to the photo-generated current. The system reaches steady state when the voltage on the P-diffusion node creates a forward bias current exactly equal in magnitude (but opposite in polarity) to the photocurrent. If this PN junction has no deviations from the ideal diode equation, then the output voltage is given by the following equation:

$$V_{out}=V_t \ln(I_p/(AI_s)+1), \qquad \text{(Eq. 1)}$$

where $V_t$ is the thermal voltage (approximately 26 mV at room temperature), $I_p$ is the photo-current, A is the cross-sectional area of this PN junction, and $I_s$ is the reverse saturation current for a PN junction with unit cross-sectional area. The value of $I_s$ depends greatly on the IC process and material parameters.

Two major error currents are present in PN junctions operating at low current density: recombination current and generation current. Except at very low temperatures, free carriers are randomly created in the PN junction space charge region. Since this region has a high field, these thermally excited carriers are immediately swept across the junction and form a current component (generation current) in the same direction as the photocurrent. Carriers crossing the space-charge region also have a finite chance of recombining. This creates another current component (recombination current) in the opposite direction of the photocurrent. Therefore, taking into account these error currents, Eq. 1 becomes:

$$V_{out}=V_t \ln((I_p+I_g-I_r)/(AI_s)+1). \qquad \text{(Eq.2)}$$

This output voltage is a function of parameters that are generally beyond the inventors' control. However, the inventors do have control over the junction area, A. Unfortunately, to make the inventors' output signal larger, the inventors want a small A, while the inventors want a large A for a high quantum efficiency (QE).

Figure 5B:
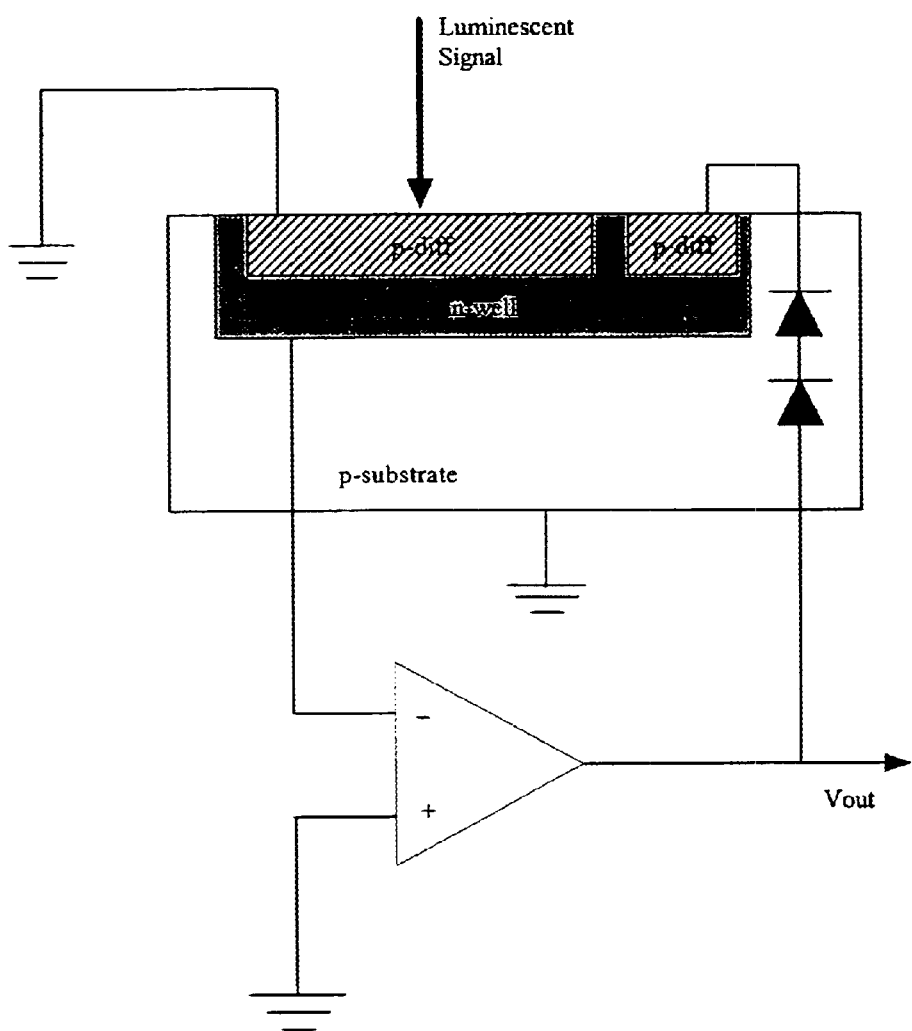
FIG. 5B shows a circuit using a large area photodiode for efficient light collection, and a small-area diode in a feedback loop to supply the forward bias current that cancels out the photocurrent.

FIG. 5B shows a second microluminometer embodiment that satisfies both of these needs. This circuit uses a large area photodiode for efficient light collection, but uses a small-area diode in a feedback loop to supply the forward bias current that cancels out the photocurrent. Once again, the amplifier and feedback diodes are fabricated on the same IC as the photodiode. For this circuit:

$$V_{out}=3V_t\ln((I_p+I_g-I_r)/(A_{fb}I_s)+1), \qquad \text{(Eq. 3)}$$

where $A_{fb}$ is the small cross-sectional area of the feedback diode. More than one diode is used in the feedback path to make the output signal large compared to the DC offset of any subsequent amplifier stages. This technique allows efficient collection of the light with a large-area photodiode, yet produces a large output voltage because of the small-area diodes in the feedback path.

The feedback circuit of FIG. 5B maintains the photodiode at zero bias. With no applied potential, the recombination and generation currents should cancel. Eq. 3 becomes:

$$V_{out}=3V_t\ln((I_p/(A_{fb}I_s))+1) \qquad \text{(Eq. 4)}$$

if the smaller recombination and generation currents in the smaller feedback diodes are neglected.

The principal advantages of the second microluminometer embodiment shown in FIG. 5B include:

- The SNR is totally determined by the photodiode; noise from the small diode and amplifier are negligible;
- Diodes can be added in the feedback path until the signal level at the output of the amplifier is significant compared to offset voltages (and offset voltage drift) of subsequent stages;
- This method is completely compatible with standard CMOS processes with no additional masks, materials, or fabrication steps;
- This detection scheme can be fabricated on the same IC with analog and digital signal processing circuits and RF communication circuits; and,
- Measurement can be made without power applied to the circuit. Power must be applied before the measurement can be read, but the measurement can be obtained with no power.

Figure 5C:
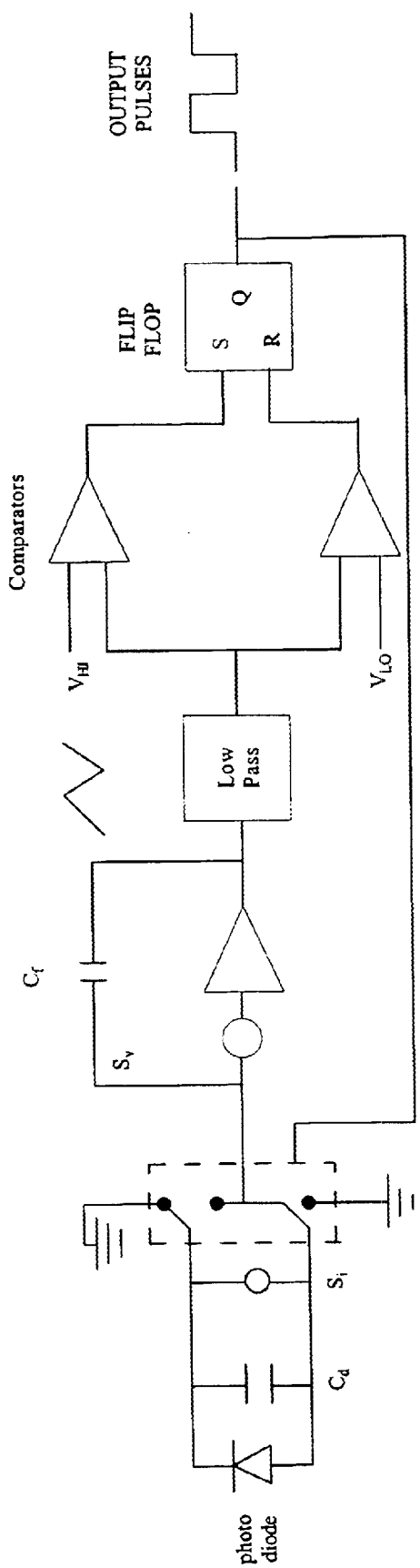
FIG. 5C shows a circuit using correlated double sampling (CDS) to minimize the effects of low frequency (flicker) amplifier noise as well as time or temperature dependent variations in the amplifier offset voltage.

A third microluminometer implementation shown in FIG. 5C uses correlated double sampling (CDS) to minimize the effects of low frequency (flicker) amplifier noise as well as time or temperature dependent variations in the amplifier offset voltage. As shown in FIG. 5C, a photodiode with capacitance $C_d$ and noise power spectral density $S_i$ is connected to an integrating preamplifier with feedback capacitance $C_f$ and input noise power spectral density $S_v$ through a set of switches that are controlled by the logical level of a flip-flop output. When the flip-flop output is low, the switches are positioned so that the photocurrent flows out of the preamplifier, causing the output voltage of the integrator to increase. When the low-pass filtered integrator output voltage exceeds a threshold, $V_{HI}$, the upper comparator "fires" setting the flip-flop and causing its output to go high. The detector switches change positions, causing current to flow into the integrating amplifier, which in turn causes the amplifier output voltage to decrease. When the integrator output goes below a second threshold, $V_{LO}$, the lower comparator "fires" resetting the flip-flop and causing the output to go low again. The process repeats itself as long as a photocurrent is present.

The average period of the output pulse, $\Delta t$, is given by the following equation:

$$\Delta t = \frac{2C_f(V_{HI}-V_{LO})}{I_P}, \qquad \text{(Eq. 5)}$$

where $V_{HI}$ and $V_{LO}$ are the threshold voltages of the comparators and $I_p$ is the diode photocurrent. Two noise sources contribute to error in the measured value of $\Delta t$. $S_i$ is the input noise current power spectral density associated primarily with the photodiode, and $S_v$ is the input noise voltage power spectral density associated primarily with the preamplifier. The diode noise is given by the equation:

$$S_i = 2q(2I_s + I_p)\left(\frac{A^2}{\text{Hz}}\right),\quad \text{(Eq. 6)}$$

where $I_s$ is the photodiode reverse saturation current and $I_p$ is the photocurrent. As the photocurrent approaches zero, the noise power spectral density approaches a finite value of $4qI_s A^2/\text{Hz}$. The noise voltage $S_v$ of the preamplifier is determined by its design and has units of $V^2/\text{Hz}$.

The transfer function from the point where the diode noise is introduced to the output of the integrator is given approximately by the equation:

$$H_i(\omega) \approx \left(\frac{1}{sCf}\right)\left(\frac{\omega_1}{s+\omega_1}\right),\quad \text{(Eq. 7)}$$

where $\omega_1$ is the corner frequency of the integrating amplifier and $s=j\omega$. Ignoring for the moment the effect of the switches, the transfer function from the point where the amplifier noise is introduced to the output of the integrator is given approximately by the equation:

$$H_v(\omega) \approx \left(\frac{C_f + C_d}{C_f}\right)\left(\frac{\omega_1}{s+\omega_1}\right).\quad \text{(Eq. 8)}$$

The switches perform a correlated double sampling function that attenuates the noise that appears below the switching frequency of the output pulse string. The transfer function of a correlated double sampling circuit is approximated to first order by the equation:

$$H(\omega) \approx \left(\frac{s}{s+2/\Delta t}\right),\quad \text{(Eq. 9)}$$

where $\Delta t$ is the average period of the output pulse string. Thus, taking into account the switches, the transfer function from the point where the amplifier noise is introduced to the output of the integrator is approximately given by the equation:

$$H_v(\omega) \approx \left(\frac{C_f + C_d}{C_f}\right)\left(\frac{\omega_1}{s+\omega_1}\right)\left(\frac{s}{s+2/\Delta t}\right).\quad \text{(Eq. 10)}$$

This is an important result because the effective zero introduced in the noise voltage transfer function reduces the effect of the flicker noise of the amplifier. This is particularly useful in CMOS implementations of the micro-luminometer where flicker noise can have a dominant effect.

The mean squared output noise at the output of the integrator is given by the equation:

$$v_n^2 = \int_{-\infty}^{\infty} S_v(H_v * H_v) + S_i(H_i * H_i)\, d\omega,\quad \text{(Eq. 11)}$$

and the RMS noise voltage is then given by the equation:

$$\sigma_v = \sqrt{v_n^2}.\quad \text{(Eq. 12)}$$

The RMS error in the measured period is determined by the slope of the integrated signal and the noise at the output of the integrator following the relationship:

$$\sigma_t = \frac{\sigma_v}{\frac{dv}{dt}}\quad \text{(Eq. 13)}$$

or, approximately, by the equation:

$$\sigma_t \approx \frac{\sigma_v}{\frac{(V_{HI} - V_{LO})}{\Delta t}}.\quad \text{(Eq. 14)}$$

The error in measuring $\Delta t$ may be reduced by collecting many output pulses and obtaining an average period. The error in the measured average pulse period improves proportionately to the square root of the number of pulses collected, such that $$\overline{\sigma}_t \approx \frac{\sigma_v}{\frac{(V_{HI} - V_{LO})}{\Delta t}} \frac{1}{\sqrt{N}}\quad \text{or}\quad \text{(Eq. 15)}$$

$$\overline{\sigma}_t \approx \frac{\sigma_v}{\frac{(V_{HI} - V_{LO})}{\Delta t}} \sqrt{\frac{t_{meas}}{\Delta t}}\quad \text{(Eq. 16)}$$

where $t_{meas}$ is the total measurement time.

Thus, implementation of the micro-luminometer has the following advantages:

The low frequency "flicker" noise of the amplifier is reduced by a correlated double sampling process; and, Ideally, the accuracy of the measured photocurrent may be improved without limit by acquiring data for increasing periods of time.

Of course, practical limitations imposed by the lifetime and stability of the signals produced by the luminescent compound under test will ultimately determine the resolution of this implementation.

4.4 Read-out Electronics

Several methods of communicating data from the BBIC to external receivers or in vivo drug delivery systems are envisaged. In a preferred embodiment the communication method is an on-chip wireless communication system that reports the level of the photocurrent to computing circuitry contained within in vivo drug delivery system or an external receiver. In a closed-loop system, this computing circuitry would determine the amount of drug to be delivered by the in vivo drug delivery system. If an external receiver were used, the data from the BBIC along with the user inputs would be used to determine the amount of drug to be administered. The external receiver may include wireless transmission circuitry for communication with the in vivo drug delivery system or the drugs may be administered manually. Other methods of communicating BBIC data include;

Generation of a DC voltage level proportional to the photocurrent with a hardwire connection to an in vivo drug delivery system;

Generation of a DC current level proportional to the photocurrent with a hardwire connection to an in vivo drug delivery system;

Generation of a logical pulse string whose rate is proportional to the photocurrent with a hardwire connection to an in vivo drug delivery system;

On-chip implementation of an analog to digital converter that reports a numerical value proportional to the photocurrent with a hardwire connection to an in vivo drug delivery system;

On-chip implementation of a serial or parallel communications port that reports a number proportional to the photocurrent with a hardwire connection to an in vivo drug delivery system;

Generation of a logical flag when the photocurrent exceeds a predefined level with a hardwire connection to an in vivo drug delivery system; and, Generation of a radio-frequency signal or beacon when the photocurrent exceeds a predefined level.

Wireless communication in vivo may be limited by signal attenuation by body fluids, tissues, and health-related limits on RF signal levels. This may require the BBIC and in vivo drug delivery system to be closely spaced, which may not be the optimum configuration for all cases. In such cases, the BBIC could communicate to an external receiver located ex vivo but closer to the BBIC. This receiver could be connected (hardwired or wirelessly) to a transmitter located ex vivo but closer to the in vivo drug delivery system.

Numerous algorithms are envisioned for controlling an in vivo drug delivery system with a BBIC. These include, but are not limited to a simple look-up table that administers a prescribed drug level that is determined only by a single BBIC data point;

a simple look-up table that administers a prescribed drug level when a predetermined number of data points exceed a preset threshold;

an algorithm that determines drug dosage by rate of increase or decrease of BBIC signal an algorithm that determines drug dosage by matching BBIC data points to data point patterns stored in memory learning algorithms that use BBIC data point history and user inputs to predict correct drug dosage to achieve desired results Some of these algorithms may require two-way communication between the BBIC and in vivo drug delivery system. In this case, a receiver would be included on the BBIC.

4.5 Biocompatlble Housing and Semi-permeable Membrane

The BBIC is enclosed in a biocompatible housing with a semi-permeable membrane covering the bioreporter region. The preparation of biocompatible coverings for implants and prosthetic devices so as to minimize capsule formation and physiological rejection has been an area of extensive investigation. For example, U.S. Pat. No. 5,370,684 and U.S. Pat. No. 5,387,247 (each specifically incorporated herein by reference in its entirety), describe the application of a thin biocompatible carbon film to prosthetic devices. A biocompatible implant material comprising a three-dimensionally woven or knitted fabric of organic fibers is disclosed in U.S. Pat. No. 5,711,960, specifically inlcuded nerein in its entirety. Other coverings for implants constructed to present a biocompatible surface to the body are described in U.S. Pat. No. 5,653,755, U.S. Pat. No. 5,779,734, and U.S. Patent 5,814,091 (each specifically incorporated herein by reference in its entirety). In addition, collagen coating and albumin coating have been shown to improve the biocomapatibilty of implants and prosthetic devices (Marios et al., 1996; Ksander, 1988). The present invention contemplates the use of any suitable biocompatible material to either coat or form the housing.

A semi-permeable membrane comprises that part of the BBIC housing that covers the bioreporter and entraps them on the integrated circuit. This membrane allows the selected substance, such as glucose, to pass to the bioreporter, yet prevents the passage of larger molecules. Membranes designed for use with glucose-oxidase based biosensors may also used in the preferred embodiments of the present invention. Membranes investigated and designed for use with glucose-oxidase based biosensors include, but are not limited to: polytetrafluoroethylene membranes (Vaidaya and Wilkins, 1993); perfluorinated ionomer membranes (Moussy et al., 1994); charged and uncharged polycarbonate membranes (Vadiya and Wilkins 1994); and cellulose acetate membranes (Wang and Yuan, 1995; Sternberg et al., 1988). In addition, other membranes have been developed for the use transplantation of islets or other cells bioengineered to produce insulin. The membranes must be permeable to glucose and other metabolites while exclude elements of the host immune system. Such membranes may be adapted for use with the present invention and include, but are not limited to: asymmetric poly(vinyl alcohol) membranes (Young et al., 1996); poly(L-lysine) membranes (Tziampazis and Sambanis, 1995); ployurethane (Zondervan et al., 1992); nucleopore membranes (Ohgawara et al., 1998); and agarose gel (Taniguchi et al., 1997). Biocompatible semi-permeable membranes for encapsulation of cells to form an artificial organ are described in U.S. Pat. No. 5,795,790 and U.S. Pat. No. 5,620,883 (each specifically incorporated herein by reference in its entirety). A biocompatible semi-permeable segmented block polyurethane copolymer membrane and its use for permeating molecules of predetermined molecular weight range are disclosed in U.S. Pat. No. 5,428,123, (specifcally incorporated herein by reference in its entirety). The present invention contemplates the use of any suitable semi-permeable membrane that allows the selected substance access to the bioreporter yet prevents the passage of larger molecules.

4.6 Drug Delivery Devices

Numerous drug delivery devices, implantable and external, have been previously described which can be controlled by radio telemetry. For example, U.S. Pat. No. 4,944,659 (specifically incorporated herein by reference in its entirety), describes an implantable piezoelectric pump for drug delivery in ambulatory patients. U.S. Pat. No. 5,474,552, specifically included herein in its entirety, describes an implantable pump for use in conjunction with a glucose sensor that can deliver multiple active agents, such as glucose, glucagon, or insulin as required. Separate pumps may be used for delivering each of the agents or a single pump that is switchable between them may be used. U.S. Pat. No. 5,569,186, specifcally included herein in its entirety, describes a closed loop infusion pump system controlled by a glucose sensor. U.S. Pat. No. 4,637,391, specifically included herein in its entirety, describes a remote controlled implantable micropump for delivery of pharmaceutical agents. The use of external drug delivery systems is contemplated in other embodiments of the present invention. For example, U.S. Pat. No. 5,800,420, specifically inlcuded herein in its entierty, discloses a pump position topically against the skin surface that delivers a liquid drug, such as insulin, via a hollow delivery needle extending into the dermis. In other embodiments of the present invention, the drug delivery system may be interfaced with the biosensor device and controlled directly, as opposed to remote telemetry control, from the BBIC.

The pump delivery systems described above are examples to facilitate the use of the present invention. Drug delivery devices other than pump systems are also contemplated by the present invention. For example, U.S. Pat. No. 5,421,816, specifically included herein in its entirety, describes an ultrasonic transdermal drug delivery system. Ultrasonic energy is used to release a stored drug and forcibly move the drug through the skin of an organism into the blood stream. Thus the invention contemplates the use of any suitable drug delivery system that can be controlled by the BBIC glucose monitor. The factors dictating the choice of such a drug delivery system and its use with the BBIC glucose monitor use will be known to those of skill in the art in light of the present disclosure.

4.7 Bioluminescent Bioreporters

In a preferred embodiment of the invention, the bioreporter for glucose monitoring will be a mammalian bioluminescent reporter cell line that has been genetically engineered to express luminescence in response to glucose concentrations on a continues basis. An implantable bioluminescent sensor requires a bioluminescent reporter that can function without the exogenous addition of substrate for the luciferase reaction. Current eukaryotic luciferase systems used in molecular biology require the addition of exogenous substrate because of the complex nature for the production of eukaryotic luciferins. Cells must be either permeabilized or lysed and then treated with an assay solution containing luciferin. Thus current eukaryotic luciferases systems are not preferred candidates for on-line monitoring.

The requirement for the addition of exogenous substrate can be obviated by the use of bacterial lux genes. In a preferred embodiment of the present invention the lux genes of *X. luminescens*, luxAB and luxCDE, are used as the bioluminescent reporter system. The *X. luminescens* luxAB gene encodes the α- and β-subunits of a luciferase enzyme that exhibits greatest thermostability at 37° C., while other bacterial luciferases lose significant activity above 30° C. The luxCDE genes are required to eliminate the need for the addition of exogenous substrate. The aldehyde substrate of the luciferase encoded by the luxAB genes is generated by a fatty acid reductase complex coded for by the luxCDE genes. The preferred fatty acid for this reaction is myristic acid, which is present in eukaryotic organisms (Rudnick et al., 1993), and thus eukaryotic cells are suitable host cells for this reporter. The enzyme complex reduces the fatty acid to the corresponding aldehyde. The luciferase then oxidizes the aldehyde to back to the fatty acid.

Other bioluminescence nucleic-acid segments may include the lux genes of *Vibrio fischerii*, luxCDABE, or luciferases from other organisms capable of bioluminescence that can be adapted so not as to require the addition of exogenous substrate. In other embodiments of the invention, nucleic acid segment encodes green fluorescent protein of *Aqueorea Victoria* or *Renilla reniformis*.

4.8 Recombinant Vectors Expressing Bioluminescence Genes

One important embodiment of the invention is a recombinant vector that comprises one or more nucleic-acid segments encoding one or more bioluminescence polypeptides. Such a vector may be transferred to and replicated in a eukaryotic or prokaryotic host.

It is contemplated that the coding DNA segment will be under the control of a recombinant, or heterologous promoter. As used herein, a recombinant or heterologous promoter is intended to refer to a promoter that is not normally associated with a DNA segment encoding a crystal protein or peptide in its natural environment. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology (see e.g., Sambrook et al., 1989). In a preferred embodiments of this, such promoters are directed by cis-acting glucose response elements. In one preferred embodiment, the glucose response element is the L4 box which directs the L-pyruvate kinase ("L-PK") promoter in liver and islet β-cells. The L4 box consists of a tandem repeat of non-canonical E-boxes (Kennedy et al., 1997). Glucose enhances the hepatic and pancreatic β-cell by modifying the transactivating capacity of upstream stimulatory factors ("USF") bound to the L4 box (Kennedy et al., 1997; Doiron et al., 1996).

The exact mechanism by which glucose controls the transactivational capacity of USF proteins is unclear. One possibility is the reversible phosphorylation of USF proteins. Glucose may alter the phosphorylation status through the pentose phosphate shunt via xyulose 5-phosphate (Dorion et al., 1996). An alternative mechanism is via the intracellular concentration of glucose 6-phosphate (Foufelle et al., 1992). Other glucose metabolites may also be implicated. Phosphorylated glucose metabolites include, but are not limited to, fructose 6-phosphate, 6-phosphogluconic acid, 6-phosphoglucono-δ-lactone, ribulose 5-phosphate, ribose 5-phosphate, erythrose 4-phosphate, sedoheptulose 7-phosphate, glyceraldehyde 3-phosphate and dihdyroxyacetone phosphate. Non-phosphorylated glucose metabolites include, but are not limited to, citric acid, cis-aconitic acid, threo-isocitric acid, succinic acid, fumaric acid, malic acid, oxaloacetic acid, pyruvic acid and lactic acid.

Another glucose response element, similar in arrangement to the L-PK gene L4 box, is the regulatory sequence involved in the transcriptional induction of the rat S14 gene (Shih et al., 1995). Other glucose response elements that have been described include, but are not limited to, the hepatic 6-phosphofructo-2-kinase gene (Dupriez and Rousseau, 1997), the β-islets insulin gene (German and Wang, 1994), the mesangial transforming growth factor-beta gene (Hoffman et al., 1998), and the gene for acetyl-coenzyme-A carboxylase (Girard et al., 1997). The present invention contemplates the use any glucose response element that can effectively direct a promoter or otherwise control the expression of the reporter protein in response to glucose.

In a preferred embodiment, the recombinant vector comprises a nucleic-acid segment encoding one or more bioluminescence polypeptides. Highly preferred nucleic-acid segments are the lux genes of *X. luminescens* luxAB and luxCDE. Bacterial luciferases may have to be modified to optimize expression in eukaryotic cells. Almashanu et al. (1990) fused the luxAB genes from *V. harveyi* by removal of the TAA stop codon from luxA, the intervening region between the two genes, and the initial methionine from luxB without disrupting the reading frame. The fusion was successfully expressed in *Saccharomyces cerevisiae* and *Drosophila melanogaster*. The same strategy was used with luxAB from *X. luminescens*. The resultant construct has been sequenced to verify the genetic changes to generate the fusion and they were confirmed. The sequence of the fusion region is as follows:

```
        5'-taccctagggagaaagagaatg-3' (SEQ ID NO:7)
(end of luxA underlined)        (start of luxB underlined)
```

The fusion successfully expresses fused protein in *E.coli* and has been successfully cloned into the mammalian vector as described in Section 5.1.2.

In a further embodiment, the inventors contemplate a recombinant vector comprising a nucleic-acid segment encoding one or more enzymes that are capable of producing a reaction that yields a luminescent product or a product that can be directly converted to a luminescent signal. For example, substrates of the commonly used β-galactosidase and alkaline phosphates enzymes are commercially available that are luminescent (chemiluminescence) when converted by the respective enzyme.

In another important embodiment, the biosensor comprises at least a forst transformed host cell that expresses one or more of recombinant expression vectors. The host cell may be either prokaryotic or eukaryotic. In a preferred embodiment, the host cell is a mammalian cell. Host cells may include stem cells, β-islets cells or hepatocyte cells. In a preferred embodiment the host cells are homologous cells, i.e. cells taken from the patient that are cultured, genetically engineered and then incorporated in the BBIC. Particularly preferred host cells are those which express the nucleic-acid segment or segments comprising the recombinant vector which encode the lux genes of *X. luminescens*, luxAB and luxCDE. These sequences are particularly preferred because the transcribed proteins of the *X. luminescens* lux system have the ability to function at 37° C. (ambient human body temperature).

A wide variety of ways are available for introducing a nucleic-acid segment expressing a polypeptide able to provide bioluminescence or chemiluminescence into the microorganism host under conditions that allow for stable maintenance and expression of the gene. One can provide for DNA constructs which include the transcriptional and translational regulatory signals for expression of the nucleic-acid segment, the nucleic-acid segment under their regulatory control and a DNA sequence homologous with a sequence in the host organism, whereby integration will occur or a replication system which is functional in the host, whereby integration or stable maintenance will occur or both.

The transcriptional initiation signals will include a promoter and a transcriptional initiation start site. In preferred instances, it may be desirable to provide for regulative expression of the nucleic-acid segment able to provide bioluminescence or chemiluminescence, where expression of the nucleic-acid segment will only occur after release into the proper environment. This can be achieved with operators or a region binding to an activator or enhancers, which are capable of induction upon a change in the physical or chemical environment of the microorganisms. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon or codons, a terminator region, and optionally, a polyadenylation signal (when used in an Eukaryotic system).

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon or codons, the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

By "marker" the inventors refer to a structural gene that provides for selection of those hosts that have been modified or transformed. The marker will normally provide for selective advantage, for example, providing for biocide resistance (e.g., resistance to antibiotics or heavy metals); complementation, so as to provide prototrophy to an auxotrophic host and the like. One or more markers may be employed in the development of the constructs, as well as for modifying the host.

Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host. Desirably, the nucleic-acid segment able to provide bioluminescence or chemiluminescence will be in close proximity to the gene providing for complementation as well as the gene providing for the competitive advantage. Therefore, in the event that the nucleic-acid segment able to provide bioluminescence or chemiluminescence is lost, the resulting organism will be likely to also have lost the complementing gene, and the gene providing for the competitive advantage, or both.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the $\lambda_L$ and $\lambda_R$ promoters, the tac promoter. See for example, U.S. Pat. No. 4,332,898; U.S. Pat. No. 4,342,832; and U.S. Pat. No. 4,356,270 (each specifically incorporated herein by reference in its entirety). The termination region may be the termination region normally associated with the transcriptional initiation region or a different transcriptional initiation region, so long as the two regions are compatible and functional in the host. In a preferred embodiment of the present invention, a fragment of the L-pyruvate kinase gene is used that contains the L-PK promoter and the L4 box glucose responsive elements as described by Kennedy et al. (1997). In a highly preferred embodiment, the p.LPK.Luc$_{FF}$ plasmid is used (Kennedy et al., 1997), with the exception that the luc gene coding for the firefly luciferase is removed and replaced with the fused *X. luminescens* luxAB genes.

Where stable episomal maintenance or integration is desired, a plasmid will be employed which has a replication system that is functional in the host. The replication system may be derived from the chromosome, an episomal element normally present in the host or a different host, or a replication system from a virus that is stable in the host. A large number of plasmids are available, such as pBR322, pACYC184, RSF1010, pR01614, and the like. See for example, Olsen et al., 1982; Bagdasarian et al., 1981, and U.S. Pat. No. 4,356,270, U.S. Pat. No. 4,362,817, U.S. Pat. No. 4,371,625, and U.S. Pat. No. 5,441,884, each of which is incorporated specifically herein by reference.

The desired gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for bioluminescence or chemiluminescence activity. If desired, unwanted or ancillary DNA sequences may be selectively removed from the recombinant bacterium by employing site-specific recombination systems, such as those described in U.S. Pat. No. 5,441,884, specifically incorporated herein by reference in its entirety.

4.9 Assembly and Storage of the in Vivo Biosensor

When the biosensor consists of bioengineered cells entrapped in suspension behind a semi-permeable membrane, as opposed to encapsulated in a matrix, the cells may be added to the BBIC any time from immediately to several h before implantation of the biosensor. The biosensor may alternatively consist of cells encapsulated in a polymeric matrix. Matrices will include materials previously shown to be successful in the encapsulation of living cells, including polyvinyl alcohol, sol-gel, and alginate (Cassidy et al., 1996). Prior to encapsulation, prokaryotic cell lines may be lyophilized in a freeze dry system (e.g., Savant) following the manufacturer's protocol. Lyophilization allows cells to undergo periods of long-term storage (several years) with a simple rehydration protocol being required for cell resuscitation prior to BBIC use (Malik et al., 1993). *S. cerevisiae* eukaryotic cells may be similarly lyophilized. Eukaryotic cell lines, preferably consisting of islet β-cells, stem cells, or hepatic cells, may be encapsulated on the IC within polyvinyl alcohol mesh-reinforced or microporous filter supported hydrogels, which have previously been successfully implemented in these types of cell encapsulations (Baker et al., 1997; Burczak et al., 1996; Gu et al., 1994; Inoue et al., 1991).

In the case of the mammalian cell lines, lyophilization, however, is not an alternative. In such cases, mammalian cells may be encapsulated in a sol gel or another immobilization matrix as previously described and attached to the BBIC. The completed BBIC in its enclosure would then be stored in serum or another appropriate maintenance medium and maintained until use. The advantage of using an immortal stem cell line is apparent for both long-term use and storage. Implantation may be performed according to the specific application. In the case of glucose detection, an area where interstitial fluid is accessible would be most appropriate. However an implantable device with the specific application of detecting hormones or other blood borne molecules would have to be accessible to the bloodstream. A synthetic vein or catheter system may need to be employed to allow continuous monitoring of the blood levels of the target molecule. A specific example other than glucose would be the use of the in vivo biosensor device to detect molecules associated with colon cancer. In this case the biosensor would be implanted in the colon.

Integrated circuits may be individually packaged in sterile, static-proof bags. Prokaryotic-based and yeast eukaryotic biosensors consisting of lyophilized cells may be individually stored in sterile, static-proof, vacuum sealed bags for time periods approaching several years. Cells typically undergo rehydration in a minimal nutrient medium prior to use. Mammalian cell systems will remain frozen for long-term storage (up to 7 years at −150° C.) or refrigerated for short-term storage (several days), either separately or, if entrapped, frozen or refrigerated in situ on the BBIC. In all cases, cell viability may be checked be exposing the BBIC to a known concentration of the analyte of interest, thus producing a quantitative bioluminescent signal of known magnitude. One or more control vials of analyte(s) or reference "standards" may be included as part of a diagnostic kit, or may be supplied for proper calibration of the implantable device.

4.10 Implantation and use of the Biosensor Devices

In a preferred embodiment of the present invention, the BBIC analyte biosensor is implanted such that it is contact with the interstitial fluid of the animal. For example, in the case of glucose biosensors, it has been shown that glucose kinetics in interstitial fluid can be predicted by compartmental modeling (Gastaldelli et al., 1997). In particular the subcutaneous placement of glucose sensors has been demonstrated (Schmidt et al., 1993; Poitout et al., 1993; Ward et al., 1994; Stenberg et al., 1995; Bantle and Thomas, 1997). Other potential analyte biosensor tissue implant sites include the peritoneum, pleura and pericardium (Wolfson et al., 1982). In fact, the inventors contemplate that depending upon the particular analyte or metabolite that is being detected, the implantable biosensor may be placed in any convenient location throughout the body using conventional surgical and implant methodologies. For example, the device may be implanted in such as way as to be in contact with interstitial fluid, lymph fluid, blood, serum, synovial or cerebrospinal fluid depending upon the particular analyte to be detected.

In certain embodiments the implantable device msy be placed in contact with particular tissues, organs, or particular organ systems. Likewise, it may be desirable to implant the biosensor such that it contacts particular intracellular fluids, intercellular fluids, or any other body fluid in which the target substance can be monitored.

The present invention also contemplates the use of multiple biosensors for the detection of a plurality of different analytes. For example, in the case of glucose monitoring, one or more devices may be used to monitor various glucose or glucose metabolites, glucagons, insulin, and the like. Likewise, one or more biosensor devices may be employed in controlled drug delivery systems. As such, the device may be operably connected to a drug delivery pump or device that is capable of being controlled by the biosensor and that is able to introduce into the body of the animal an amount of a particular drug, hormone, protein, peptide, or other pharmaceutical composition determined by the concentration of one or more analytes detected by the BBIC device. Thus, controlled drug delivery systems are contemplated by the inventors to be particularly desirable in providing long-term administration of drugs to an animal such as in the case of chronic or life-long medical conditions or where symptoms persist for a long period of time. The long term controlled delivery of drugs such as pain medications, heart or other cardiac regulators, diuretics, or homones or peptides such as insulin, or metabolites such as glucagon or glucose can be facilitated by such biosensor/pump systems. In cases where it is necessary to deliver more than one drug or metabolite to the animal, multiple drug delivery systems or a single switchable drug delivery system is contemplated to be particularly useful.

Host-rejection effects can be minimized through immunoisolation techniques. Previous studies have shown that living non-host cells enclosed in hydrogel membranes are protected from immune rejection after transplantation (Baker et al., 1997; Burczak et al., 1996; Inoue et al., 1991). The hydrogels block access by the humoral and cellular components of the host's immune system but will remain permeable to the target substance glucose. A mesh-reinforced polyvinyl alcohol hydrogel bag developed by Gu et al. (1994) may be used to fully encapsulate the BBIC, allowing for transplantation void of immunosuppressive responses.

Host rejection of the implanted biosensor is not an issue if cells from the host are used for the biosensor construction. However if other cell lines are used it may be necessary to provide a barrier between the cells and the appropriate body fluid that permits passage of the signature molecules or analytes but not bioreporter cells or body cells (white blood cells, etc.). Immunosuppressed patients are not affected, as the implant does not contain any kind of pathogenic agent that would affect the patient. In all cases, the surgical methods involved in implantation of the disclosed BBIC devices are well known to one of skill in the surgical arts.

In an illustrative embodiment, the BBIC glucose sensor may be used for monitoring glucose in diabetic patients. However, such a sensor can also be used in other conditions where glucose concentrations are of concern, such as in endurance athletes or other condition involving either hypo- or hyperglycemia. Such measurements may be the end point for investigative or diagnostic purposes or the sensors may be linked via telemetry or directly to a drug delivery system.

The use of implantable BBICs for substances other than glucose can be used in a range of therapeutic situations. With the incorporation of an appropriate cis-activating response element, BBICs could monitor a number of substances and could find use in chronic pain treatment, cancer therapy, chronic immunosuppression, hormonal therapy, cholesterol management, and lactate thresholds in heart attack patients. For example, Section 5.7 describes the use of the BBICs in the detection and diagnosis of cancer.

Individual biosensors can be calibrated to check for viability of the cells as well as performance. The calibration is performed by exposing the sensor to solutions containing varying concentrations of the analyte(s) of interest. The bioreporter may be calibrated by a series of standard analyte concentrations for the specific application after its initial construction. The overall on-line performance can be monitored using microfluidics with a reservoir of the analyte, which would systematically provide a known concentration to the cells this would allow both calibration and test for viability.

The luminescence response is then correlated to concentration and the parameters set. Viability can also be continuously monitored by bioengineered cells in which the reporter exhibits continuous luminescence. Loss of viability results in decreased luminescence. This technique has been used to detect the viability of prokaryotic cells. Thus the BBIC would contain two bioreporters, the bioreporter detecting the selected substance and the second bioreporter exhibiting a luminescence proportional to cell viability. Measurement of the ratio of the signals from the two bioreporters would give a detection method that would automatically correct for any loss in viability.

Once prepared the bioreporters can be stored in the appropriate maintenance medium (e.g., standard tissue culture media, sera, or other suitable growth or nutrient formulations), and then calibrated prior to implantation. The viability of the devices may be checked by bioluminescence using microfluidics, or by the quantiation of known standards or other reference solutions to ensure viability and integrity of the system prior to, or after implantation.

In certain embodiments of the invention, the monolithic biosensor devices may be used external to the body of the monitored individual. In some clinical settings the monitor may be used to monitor glucose in body fluids in an extracorporeal fashion. The device may even be used in the pathological or forensic arts to detect the quantity of particular analytes in body tissues or fluids and the like. Likewise, the present invention also contemplates use of the biosensor devices in the veterinary arts. Implantation of such devices in animals for the monitoring of hormone levels in the blood (i.e. for optimizing milk production), monitoring the onset of estrous (heat) in numerous animals to maximize artificial insemination efficiency, and monitoring hormone levels in the milk produced on-line (in the udder) etc. is contemplated to provide particular benefits to commercial farming operations, livestock industries and for use by artisans skilled in veterinary medicine.

4.11 Diagnostics Kits Comprising In Vivo Biosensors

While the individual components of the invention described herein may be obtained and assembled individually, the inventors contemplate that, for convenience, the components of the biosensor may be packaged in kit form. Kits may comprise, in suitable container means, one or more bioreporters and an integrated circuit including a phototransducer. The kit will also preferably contain instructions for the use of the biosensor apparatus, and may further, optionally comprise a drug delivery device or a second biosensor apparatus. The kit may comprise a single container means that contains one or more bioreporters and the integrated circuit including a phototransducer and drug delivery device. Alternatively, the kits of the invention may comprise distinct container means for each component. In such cases, one container would contain one or more bioreporters, either in an appropriate medium or pre-encapsulated in a polymer matrix, another container would include the integrated circuit, and another conatiner would include the drug delivery device. When the bioreporter is pre-encapsulated, the kit may contain one or more encapsulation media. The use of distinct container means for each component would allow for the modulation of various components of the kits. For example, several bioreporters may be available to choose from, depending on the substance one wishes to detect. By replacing the bioreporter, one may be able to utilize the remaining components of the kit for an entirely different purpose, thus allowing reuse of components.

The container means may be a container such as a vial, test tube, packet, sleeve, shrink-wrap, or other container means, into which the components of the kit may be placed. The bioreporter or any reagents may also be partitioned into smaller containers or delivery vehicles, should this be desired.

The kits of the present invention also may include a means for containing the individual containers in close confinement for commercial sale, such as, e.g., injection or blow-molded plastic containers into which the desired components of the kit are retained.

Irrespective of the number of containers, the kits of the invention also may comprise, or be packaged with, an instrument for assisting with the placement of the bioreporter upon the integrated circuit. Such an instrument may be a syringe, pipette, forceps, or any other similar surgical or implantation device. The kit may also comprise one or more stents, catheters, or other surgical instrument to facilitate implantation within the body of the target animal. Such kits may also comprise devices for remote telemetry or devices for data storage or long term recordation of the data obtained from the monitoring device. Likewise, in the case of controlled drug delivery systems, the kits may comprise one or more drug delivery pumps as described above, and may also comprise one or more pharmaceutical agents themselves for administration. As an example, in the case of a glucose monitoring system, the system would typically comprise a glucose-sensitive BBIC device, a drug delivery pump, instructions for the implantation and/or use of the system, and optionally, reference standards or pharmaceutical formulations of insulin, glucagon or other pharmaceutical composition. The system may also optionally comprise growth and/or storage medium to support the nutritive needs of the bioreporter cells comprised within the BBIC device.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Construction of a Bioluminescence Reporter for Mammalian Cell Lines

To facilitate the construction of an implantable bioluminescent glucose sensor it will be necessary to create a bioluminescent reporter system that can function without the exogenous addition of substrate for the luciferase reaction. This exogenous addition is due to the complex nature of the production of luciferins for the various eukaryotic luciferases. Cells must be either permeablized or lysed and then treated with an assay solution containing luciferin. Therefore, the present state of bioluminescence reporters used in eukaryotic molecular biology makes them unsuitable for "on-line" monitoring. The firefly luciferase has been used in examining the regulation of L-pyruvate kinase promoter activity in single living rat islet β-cells (Kennedy et al., 1997). However, these cells had to be perfused with Beetle luciferin in order to generate a luminescence response.

To alleviate this limitation, a preferred bioluminescent reporter system for the present invention is one that does not require the addition of exogenous substrate. In the case of bacterial luciferase-based detection systems, this may be accomplished using the bioluminescent genes from $X.$ $luminescens$. In this organism, luxA and luxB genes (or a single fused luxAluxB gene encode the α- and β-subunits, respectively, of the luciferase enzyme (Meighen et al., 1991). This luciferase exhibits greatest thermostability at 37° C. while other bacterial luciferases lose significant activity above 30° C. Therefore, these bacterial luciferases can be expressed in eukaryotic cells with slight modification. Almashanu et al. (1990) fused the luxAB genes from $V.$ $harveyi$ by removal of the TAA stop codon from luxA, the intervening region between the two genes, and the initial methionine from luxB without disrupting the reading frame. The fusion was successfully expressed in $S.$ $cerevisiae$ and $D.$ $melanogaster$. Using the same strategy a fused luxAB gene sequence was developed using the genes from $X.$ $luminescens$.

To eliminate the need for the addition of exogenous substrate, cells must themselves supply the appropriate substrate for the luciferase. In the bacterial system the substrate is generated by a fatty acid reductase complex encoded by the luxCDE genes. This enzyme complex reduces short chain fatty acids to the corresponding aldehyde. The luciferase then oxidizes the aldehyde to the corresponding fatty acid. The preferred fatty acid for this reaction is myristic acid, which is present in eukaryotic organisms (Rudnick et al., 1993). Myristic acid is usually involved in the myristoylation of the amino terminus that is associated with membrane attachment (Borgese et al., 1996, Brand et al., 1996). Thus, to obviate the need for an exogenous supply of the luciferase substrate, the biosensor also preferably comprises a nucleic acid sequence that encodes the three luxC, luxD, and luxE-encoded subunits. As in the case of the luxAluxB gene fusion, the luxC, luxD, and luxE genes have been fused to produce a single luxCDE gene fusion that encodes the three subunits of the enzyme complex. The methods of preparing such gene fusions are described below:

5.1.1 Fusion of the LuxAB and LuxCDE Genes

The luxAB genes may be fused using conventional molecular biology techniques. For example, the polymerase chain reaction may be routinely employed for this purpose. By synthesizing a 5'-primer whose sequence begins with ATG for the start codon for the luxA gene juxtaposed by a 3'-primer ending with the codon immediately preceding the ATT stop codon. These primers may then be used in amplification reactions and the product gel purified. The luxB gene may also be amplified as above using primers that eliminate the ATG initial methionine codon but preserve the reading frame. The PCR™ reactions employ a thermostable polymerase such as the Pfu™ polymerase of Stratagene (La Jolla, Calif.), which does not have terminal deoxytransferase activity and therefore generates a blunt end. The resultant PCR™ products are blunt-end ligated, and the ligation is then subjected to PCR™ using the 5'-primer from luxA and the 3'-primer from luxB using Taq polymerase to facilitate TA cloning (Invitrogen, San Diego, Calif.). Only ligations with the correct orientation of fragments are amplified. The luxAB amplicon is then gel purified and TA cloned into a suitable vector (such as the PCRII™ vector) and transformed into $E.$ $coli$ using standard manufacturer's protocols.

Transformants are screened for light production by the addition of n-decanal which, when oxidized by the luciferase, generates bioluminescence. Only colonies emitting light are selected since they are in the proper orientation for further genetic manipulation. The luxCDE fusion is generated using the same strategy as above except transformants are screened by minipreps followed by restriction digestion analysis to determine orientation. Plasmids are amplified in E. Coli, recovered and purified twice on CsCl gradients.

5.1.2 Expression of LuxAB and LuxCDE in HeLa Cells

To determine the relative activity of the fused bacterial luciferase components, cloned fragments containing luxAB are cloned into a suitable mammalian expression vector (such as pcDNA 3.1 and luxCDE-containing fragments are cloned into a suitable mammalian expression vector (such as pcDNA/Zeo 3.1) (Invitrogen, Faraday, Calif.). Both vectors constitutively express inserted genes. HeLa cells are then transfected with luxAB or both luxAB and luxCDE and selected using appropriate antibiotics following the manufacturer's protocol (Promega, Madison, Wis.). Cells receiving the luxAB fusion are exposed to n-decanal and checked for bioluminescence. These cells cotransfected with luxCDE are then examined for bioluminescence to ascertain the relative expression of the luxCDE fusion. This permits the comparison of bioluminescence via the addition of exogenous aldehyde versus aldehyde that is produced endogenously.

An alternate strategy to enhance bioluminescent expression involves engineering a vector that would contain three copies of the eukaryotic expression machinery contained in pcDNA3.1 (Stratagene, La Jolla, Calif.). This allows for the expression of the individual components of luxCDE since it has already been shown that the fused luciferase is expressed in eukaryotic cell lines (Almashanu et al., 1990).

5.2 Example 2

Construction of a Glucose Bioluminescent Biosensor

The firefly luciferase has been used in examining the regulation of L-pyruvate kinase promoter activity in single living islet β-cells (Kennedy et al., 1997). A glucose response element designated the L4 box has been determined to be in the proximal promoter. A 200-bp fragment containing this region was cloned in front of the firefly luciferase (luc) in plasmid pGL3Basic resulting in a glucose reporter plasmid designated p.LPK.Luc$_{FF}$. Results resulted in the detection of single cells that were exposed to 16 mM glucose but not 3 mM glucose. However, these cells had to be perfused with Beetle luciferin making it unacceptable for an on-line biosensor. Therefore, a bioluminescent sensor for glucose was constructed by replacing the firefly luciferase in p.LPK.Luc$_{FF}$ with the fused luxAB gene as described below.

5.3 EXAMPLE 3

Bioluminescent Reporter Construction and Transfection of Rat Islet β-Cells

The bioluminescent reporter plasmid was constructed by removing the luc gene coding for the firefly luciferase from p.LPK.Luc$_{FF}$ and replacing it with the fused luxAB gene. This was accomplished by cleaving the luc gene from p.LPK.Luc$_{FF}$ and cloning in the luxAB gene. The resultant plasmid was amplified in E. coli and the plasmid DNA extracted and double purified on CsCl gradients.

Islet cells were prepared as previously described (German et al., 1990) and transfected by electroporation with the bioluminescent reporter construct and the plasmid containing the constitutively expressed luxCDE construct. This configuration causes the cells to maintain a pool of the aldehyde substrate that is available to the reporter genes (luxAB). Cells were screened for light production in a range of glucose concentrations from 3 mM to 30 mM. Transfected cells were washed, concentrated, and placed in a microwell in a light-tight cell that is then affixed to the integrated circuit. Different concentrations of glucose and assay media (Kennedy et al., 1997) were added to the cells to examine sensitivity and response time of the glucose BBIC.

5.4 Example 4

Preparation of Bioluminescent Reporter Constructs

The use of reporter gene technology is widespread in studying gene regulation in both eukaryotic and prokaryotic systems. Various genes are used depending on the cell lines being investigated. However with the BBIC technology the use of reporter genes that result in the emission of light is required. Therefore, reporter genes coding for bioluminescence are utilized. All previously developed reporters utilizing other reporter genes for example the gene coding for β-galactosidase (lacZ) may be converted to the bioluminescent version using standard molecular techniques and the reporter genes utilized in this specific application (modified lux system). Therefore, any currently existing reporter cell line for testing gene expression in mammalian cell lines may be adapted for use as a bioreporter when converted to the lux reporter. The implantable system simply contains the appropriate reporter cell line. Table 1 shows a list of examples of eukaryotic reporter cell lines that may be exploited in an implantable biosensor.

TABLE 1

| Reporter Gene Fusion | Application | Reference |
|---|---|---|
| ADH4-LUC | Monitors expression of alcohol dehydrogenase to increasing concentrations of alcohol | Edenberg et al., 1999 |
| TH-lacZ | Shows increased gene expression in mice subjected to chronic cocaine or morphine exposure | Boundy et al., 1998 |
| Estrogen regulated-LUC | Detects estrogens and xenoestrogens by there effect on the estrogen response element | Balaguer et al., 1999 |
| IGFBP-5-LUC | Detects the presence of progesterone by the upregulation of the reporter construct | Boonyaratanakornkit et al., 1999 |
| CYP1A-lacZ | Detects compounds that cause an upregulation of cytochrome P450 (potential carcinogens) | Campbell et al., 1996 |

5.5 Example 5

Construction and Implantation of a Glucose Biosensor and Insulin Delivery Pump

In one embodiment, a pair of bioluminescent reporters may be utilized that are in tandem and that specifically respond to deviations in glucose concentrations. One bioreporter utilizes the luxAB and luxCDE genes from *X. Luminescens* incorporated into a plasmid-based system designated p.LPK.Luc$_{FF}$, which contains a eukaryotic luc gene able to respond to glucose concentrations (increasing bioluminescence corresponds to increasing glucose concentrations). The second bioreporter utilizes a plasmid construct containing the promoter for the phosphoenolpyruvate carboxylase gene (PEPCK) that also responds to glucose concentrations, except increased bioluminescence corresponds to decreased levels of glucose. The incorporation of the luxAB and luxCDE genes into each construct allow for bioluminescence measurements to occur in real-time with deviations in glucose concentrations, negating the requirement for cell destruction and substrate addition.

Figure 9:
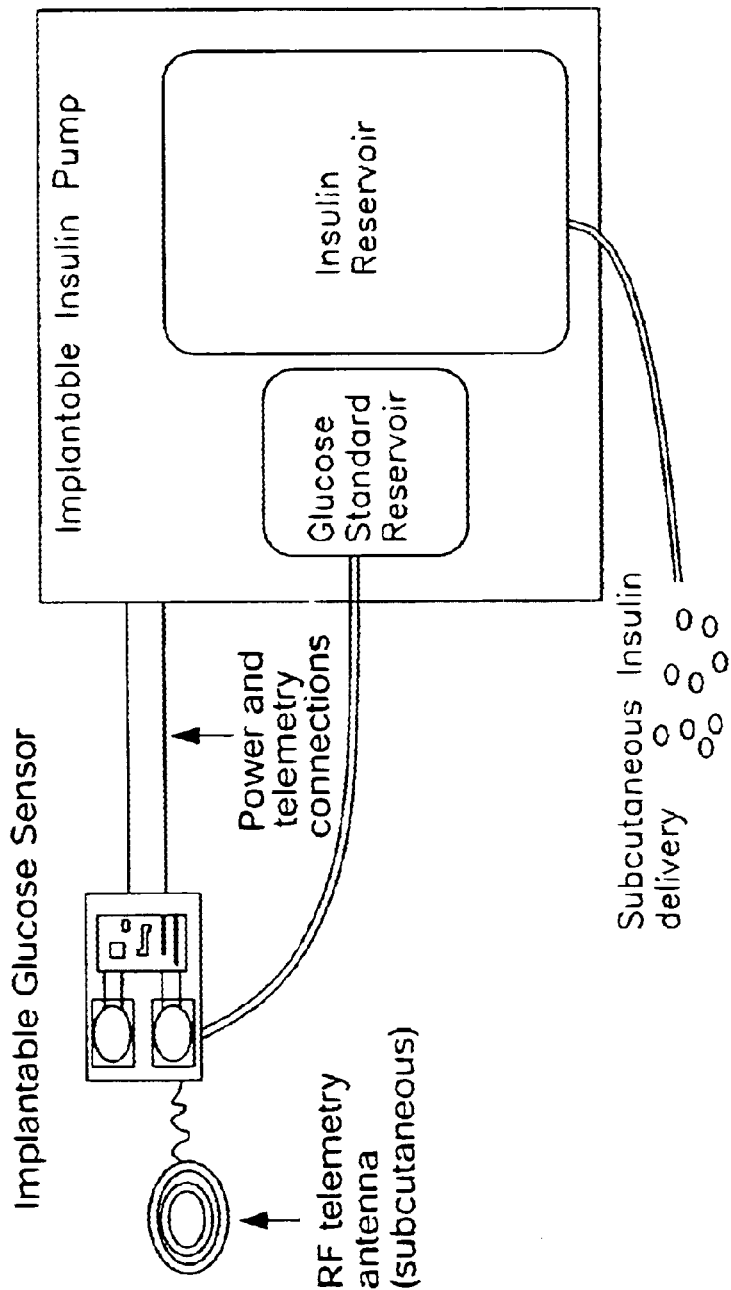
FIG. 9 shows the schematic representation of a peritoneal glucose biosensor and insulin pump.

In this embodiment, the integrated circuit comprises separate photodetector units for each bioreporter (FIG. 9A, FIG. 9B, and FIG. 9C). Bioluminescent responses from each construct can be independently monitored, allowing for the signal processing circuitry to differentiate between one bioreporter's response to increased glucose concentrations and the second bioreporter's response to decreased glucose concentrations. The signal processing circuitry processes the signals from the photodetectors, converts it to a digital format and relays the information to the implanted insulin pump (FIG. 10). The tandem set of bioreporters allows a more accurate signal as well as redundancy in the detector. Due to the often-fatal outcome of hypoglycemia, this tandem system also allows for more careful monitoring and warning of the onset of hypoglycemia.

The cells used in the tandem bioreporter system may be affixed to each of the photodetectors either directly by attachment or encapsulated in hydrogel (Prevost et al., 1997). It may be necessary to isolate the bioreporters using a semi-permeable membrane to allow the transport of small molecules such as glucose and insulin across the membrane and prohibit the influx of immune effector cells and antibodies (Monaco et al., 1993, Suzuki et al., 1998). However small molecules such as cytokines can still enter the selective membranes and interfere with the bioluminescent reporter cell lines. This approach has been used extensively by those of skill in the art.

When applicable, bioluminescent reporter cell lines may be constructed from cells taken directly from the patient to receive the implant. This approach is particularly desirable in cases of long-term implants such as implantable insulin delivery. Cells may be obtained from the patient, genetically engineered for the appropriate monitoring function, grown in cell culture, evaluated and then preserved for long-term storage. The use of cell lines developed from the patient's own cells, is particularly desirable as it reduces the chance of host rejection and creation of an immune response to the implanted device. Preferably, stem cells (immortal stem cells, if attainable) are used when appropriate, and may be maintained and nourished in suitable culture medium. Such pluripotent, totipotent, or otherwise immortal cell lines provide particular advantage in the creation of suitable long-term implantable devices.

Before implantation the biosensor may be calibrated injecting the chamber containing the cells with various concentrations of glucose delivered from an auxiliary pump and reservoir on the insulin delivery pump (FIG. 10). This permits determination of the appropriate parameters to allow the proper dosage of insulin to be delivered. Once the parameters are set, the pump may be evaluated for insulin delivery. Systematically the glucose biosensor is recalibrated in the patient utilizing the glucose standard contained in the delivery pump.

In the case of drug delivery systems, the glucose biosensor may be operably connected to the delivery pump via a hardwire or wireless connection. The biochip provides digital data that may be input directly to the signal processing circuitry of the pump to proportionally dispense the insulin. Alternatively, the digital data may be converted into analog data and used to control the pump. When a wireless capability is added to the bioreporter device, remote monitoring of the sensor is possible. For example, in this configuration, the patient may place a radio transmitter/receiver outside the body near the implanted device to communicate the data from the implanted device to a remote station. In some applications, the radio transmitter/receiver maybe linked to a computer programmed to forward the data to a remote station over a network such as a local area network, a wide area network, or even the Internet. Such wireless applications allow remote monitoring and maintenance of the patients. There are several pumps currently on the market, which are candidates for interfacing with the biosensor. In one embodiment, the Medtronic Synchronized infusion system may be used as it has extensively used in drug delivery and utilizes a portable computer to allow programming of the pump from outside the body (Medtronic, Inc., Minneapolis, Minn.). The pump can also be refilled through the skin via a self-sealing septum. The pump is one inch thick and three inches in diameter and weighs approximately six ounces. The biosensor can be integrated into the preexisting electronic circuitry to take advantage of the out-of-body programming by a portable computer. The chip can be powered utilizing the battery that powers the delivery pump.

The biosensor/insulin pump apparatus may be surgically implanted using local anesthesia in the abdominal cavity. Both the sensor and the pump may be implanted in the peritoneal space of the abdomen both for simplicity and to avoid the complications of direct catheter placement in the blood stream. Glucose concentrations are monitored and the insulin delivered peritoneally as required by the patient (FIG. 10).

5.6 Example 6

Bioluminescent Reporter Construction and Transfection of Rat Islet β-Cells and H4IIE Hepatoma Cells The regulation of the PEPCK gene will be exploited in the construction of the bioluminescent reporter for detecting decreased glucose concentrations. This system is highly regulated as the phosphoenolpyruvate carboxylase is the rate-limiting enzyme in gluconeogenesis. PEPCK gene expression is increased in the presence of glucocorticoids and cAMP and decreased in the presence of insulin (Sasaki et al., 1984; Short et al., 1986). In both rat liver and H4IIE hepatoma cells the insulin effect is dominant and the glucocorticoids and cAMP is additive. The promoter region of the PEPCK will be cloned in front of the fused luxAB. The resultant construct will then produce increased bioluminescence in the presence of low glucose concentrations.

The bioluminescent reporter plasmid for detecting increased glucose concentration may be constructed by removing the luc gene coding for the firefly luciferase from p.LPK.Luc$_{FF}$ and replacing it with the fused luxAB. This is accomplished by cleaving the luc gene from p.LPK.Luc$_{FF}$ and cloning in the luxAB gene. The bioluminescent reporter plasmid for the detection of low glucose concentrations is constructed by replacing the chloramphenicol transferase (CAT) gene in the previously constructed PEPCK promoter CAT fusion (Petersen et al., 1988; Quinn et al., 1988) with the luxAB gene. The resultant plasmid is amplified in *E. coli* and the plasmid DNA extracted and double purified on CsCl gradients.

Islet and hepatoma cells may be prepared as previously described (German et al., 1990; Petersen et al., 1988) and co-transfected with the bioluminescent reporter construct and the plasmid containing the constitutively expressed luxCDE gene constructed in objective one. This configuration causes the cells to maintain a pool of aldehyde substrate that will be available to the reporter genes (1luxAB). Cells are screened for light production in a range of glucose concentrations from 3 mM to 30 mM. Transfected cells are washed, concentrated, and placed in a microwell in a light-tight chamber that is then affixed to the integrated circuit. Different concentrations of glucose and assay media (Kennedy et al., 1997) are added to the cells to examine sensitivity and response time of the glucose BBIC. After initial characterization, the bioluminescent glucose reporters may also be tested in a flow cell. Cells are placed in an encapsulation medium on the integrated circuit and media containing different concentrations of glucose (3-to-30 mM) is then perfused across the cells to examine dynamic responses.

5.7 Example 7

BBICs in the Diagnosis and Detection of Cancer

Colon cancer is the second leading cause of cancer death after lung cancer in the United States, and the incidence increases with age in that 97% of colon cancer occurs in persons greater than 40 (Coppola and Karl, 1998). Although most cases of colon cancer are sporadic, in 15% of the patients there is a strong familial history of similar tumors in first-degree relative relatives (Coppola and Karl, 1998). These familial cancers such as hereditary nonpolyposis colon cancer (HNPCC) and familial adenomatous polyposis (FAP) result from autosomal dominant inheritable genetic mutations in putative tumor suppressor genes, and a spectrum of lesions occurs from hyperplasia-dysplasia-adenoma-carcinoma (Coppola and Karl, 1998). Because much of the early molecular lesions are known about inherited colonic cancer, they represent a useful model for development of a novel biosensor strategy for early clinical detection. Biosensors are hybrid devices combining a biological component with a computerized measuring transducer.

This example describes the adaptation of the implantable biosensor device to permit early detection of cancers, and to permit means for monitoring remission and recurrence of cancer. Because the miniaturized biosensors of the present invention are small enough to be implantable, and can be combined with a reporter system engineered to produce light without the need for cellular lysis or additional substrate, a powerful tool for early diagnosis of colon cancer in the form of an implantable device is now possible for the first time.

As described above for glucose and other metabolite biosensors, the inducible reporter system utilized is based on the luxAB and luxCDE genes from *X. luminescens* placed in a eukaryotic reporter cell so that expression of certain genes or their products can be detected by expression of biolumi-nescence by the BBICdevice. The eukaryotic reporter cell is treated with mitomycin C so it is unable to divide, but is still able to respond metabolically and produce a quantitative bioluminescent signal.

Colon cancer is the second leading cause of cancer death in the United Sates, with at least 50% of the population developing a colorectal tumor by the age of 70 (Kinzler and Vogelstein, 1996). Although most cases of colorectal cancer are sporadic, 15% are the result of heritable cancer syndromes, familial adenomatous polyposis (FAP) and hereditary nonpolyposis colorectal cancer (HNPCC) (Kinzler and Vogelstein, 1996). Familial adenomatous polyposis is a syndrome characterized by the development of hundreds to thousands of adenomas or polyps in the colon and rectum, only a small number of which develop into invasive cancer (Kinzler and Vogelstein, 1996). Loss of function of both alleles of the adenomatous polyposis coli (APC) tumor suppressor gene predisposes persons to develop malignant cancer (Coppola and Marks, 1998). In addition, most sporadic colon cancers are also found to contain mutations in the APC gene (Kinzler and Vogelstein, 1996). In hereditary nonpolyposis colorectal cancer, there is marked microsatellite instability secondary to mutations in DNA mismatch repair genes such as hMSH2 and hMSH1; single, high grade tumors develop at a young age and are usually confined to the right colon (Coppola and Karl, 1996; Smyrk, 1994). Whereas cells with mutations in APC are generally aneuploid from loss of whole sections of chromosomes, cells with mutations in hMSH2 or hMSH1 are euploid (Lengauer et al., 1998).

The molecular events leading to the development of colonic neoplasia are fairly well understood (Kinzler and Vogelstein, 1996). Persons with complete loss of APC develop lesions in the colon called dysplastic aberrant crypt foci that progress to early adenomas (Kinzler and Vogelstein, 1996). Other mutations begin to accumulate, such as those in K-Ras or p53, and the tumors progress to late adenomas, carcinomas, and metastatic carcinomas (Kinzler and Vogelstein, 1996). A similar progression is seen in HNPCC as well. Because the sequence of genetic events is fairly well understood for both these types of cancer, they represent excellent models for development of sensitive and specific diagnostic tests that can be used to detect one or more altered cells in vitro.

The APC gene encodes a cytoplasmic protein that localizes to the ends of microtubules at focal adhesion complexes (Kinzler and Vogelstein, 1996). As cells migrate up through the crypts, expression of APC increases until the terminally differentiated and located colonic epithelial cells undergo apoptosis (Kinzler and Vogelstein, 1996). Cadherins are transmembrane proteins that are localized to focal adhesion plaques in most epithelial cells (Aplin et al., 1998). The carboxy terminus of each cadherin interacts with cytoplasmic structural proteins known as catenins (Aplin et al., 1998). There are three types of catenins: β-catenin binds to the cytoplasmic domain of cadherin; -catenin binds to β-catenin and the actin cytoskeleton via -actinin; -catenin functions in place of β-catenin in some cell types (Aplin et al., 1998). β-Catenin also is part of a signal transduction pathway involving the secreted glycoprotein Wnt and glycogen synthase kinase 3 (GSK3) (Aplin et al., 1998). APC interacts with several components of the Wnt-β-catenin-GSK3 pathway, including β- and γ-catenins, GSK3, and tubulin (Aplin et al., 1998). Most of the mutations in colorectal cancer are in the carboxy terminal region of APC so that it can no longer bind β-catenin (Aplin et al., 1998). In fact, -catenin lies downstream of APC and is critical for its function as a tumor suppressor gene (Aplin et al., 1998). When the Wnt pathway is inactivated, GSK3 phosphorylates the N-terminus of β-catenin, targeting it for degradation by the ubiquitin pathway (Munemitsu et al., 1996). When β-catenin accumulates, it activates gene transcription via the transcription factor Lef-1/TCF (Morin et al., 1997). APC works in concert with GSK3 to inhibit -catenin-mediated transcriptional activity (Kinzler and Vogelstein, 1996).

In hereditary nonpolyposis colon cancer, microsatellite instability is the result of mutations in one or more DNA-mismatch repair genes (Jiricny 1998; Nicholaides et al., 1994). At least 90% of HNPCC tumors have microsatellite instability (Karran 1996; Smyrk 1994). One potential marker for microsatellite instability in colorectal tumors is inactivation of the type II receptor for TGF-β (Markowitz et al., 1995). Loss of function of βRII is associated with loss of growth regulation and tumor progression in colorectal adenomas in HNPCC (Wang et al., 1995). Other signaling components of the TGF-β pathway that are involved in colorectal tumorigenesis include mutations in Smad 3 and Smad 4, both of which result in the development of colorectal adenocarcinomas in mice (Zhu et al., 1998; Takaku et al, 1998). Loss of function of βRII is a useful marker for early lesions in HNPCC (Markowitz et al., 1995).

Because mutations in APC are the most common mutations in colorectal cancer, a reporter construct for T cell transcription factor (Tcf) was devised to screen multiple colon cancer cell lines for activation of transcriptional activity. Mutations in either APC or β-catenin result in activation of Tcf-responsive transcription through the accumulation of unphosphorylated cytoplasmic β-catenin (Morin et al., 1997) and detecting activation of a reporter construct is useful as a marker for mutations in either of these genes. The vector pDISPLAY (Invitrogen) permits expression of the promoter for Tcf on the surface of the bioreporter cell; this construct consists of a tandem set of Tcf promoters: one upstream of the genes for luxAB, the other upstream of the luxCDE. In the presence of excess β-catenin the promoter constructs will stimulate activity of the reporter and bioluminescence will result.

Once the HepG2 and HeLa cells have been transfected with pcDNA3 encoding the luxAB genes, the cells are attached to the biosensor chip. It is necessary to insure that these cells are incapable of dividing, so after transfection and selection, the cells are irradiated with 6,000 rads γ-radiation from a $^6$Co source (UT College of Veterinary Medicine). In some embodiment it may be necessary to attach the cells to the biochip prior to irradiation so that efficient attachment can occur. An alternative is to treat the cells with mitomycin C to prevent further mitosis. Biochips may be coated with Matrigel, a basement membrane material that promotes attachment of epithelial cells. An alternative approach suspends the cells in Matrigel and allows it to form a gel on the surface of the biochip. The cells are then immobilized in the basement membrane material and are not subject to dislodgement by friction. Optionally, the surface of the chip may be altered by adding a net charge (e.g., poly-L-lysine), coating the surface with surgical tissue glue, or by adding some other surface modification that allows the biopolymers to adhere tightly to the surface. Because mutations in APC are the most common mutations in colorectal cancer, a reporter construct for T cell transcription factor (Tcf) may be devised to screen multiple colon cancer cell lines for activation of transcriptional activity.

The present invention also provides a biosensor that may be used for endoscopic screening of the colonic mucosa to detect the presence of mutated cells prior to the onset of gross morphological alterations. It may be necessary to attempt detection of more than one abnormality at a time for the degree of sensitivity needed to detect small foci of malignant transformation. For example, many colonic tumors, especially those with mutations in APC, overexpress cyclooxygenase-2 (COX-2) and secrete large amounts of prostaglandins (Kutchera et al., 1996; Sheng et al., 1997; Coffey et al., 1997; Kinzler and Vogelstein, 1996).

Cyclooxygenase-2 is an early response gene that not constitutively expressed, but is turned on in colonic epithelial cells by growth factors and tumor promoters (Kutchera et al., 1996; Sheng et al., 1997; Coffey et al., 1997). It may be possible to bioengineer reporter cells to bioluminesce in the presence of increased levels of prostaglandins in the intestinal lumen. Prostaglandins freely pass the cell membrane and would be able to enter the cytoplasm of the reporter cell to activate a reporter construct. Engineering a reporter cell to detect increased levels of prostaglandins through the use of the cyclooxygenase-2 promoter fused to the luxAB genes could also be of benefit in early detection of colon cancer. Because the levels of prostaglandins may be elevated in inflammation as well as neoplasia, this approach lacks appropriate specificity for diagnosing cancer. It would, however, be useful in determining which patients would benefit from treatment with specific cyclooxygenase inhibitors.

6.0 REFERENCES

The following references, to the extent that they provide exemplary procedural or other details supplementary to those set forth herein, are specifically incorporated herein, by reference.

U.S. Pat. No. 4,332,898, issued Jun. 1, 1982.
U.S. Pat. No. 4,342,832, issued Aug. 3, 1982.
U.S. Pat. No. 4,356,270, issued Oct. 26, 1982.
U.S. Pat. No. 4,362,817, issued Dec. 7, 1982.
U.S. Pat. No. 4,371,625, issued Feb. 1, 1983.
U.S. Pat. No. 5,441,884, issued Aug. 15, 1995.
U.S. Pat. No. 4,637,391, issued Jun. 16, 1987.
U.S. Pat. No. 4,944,659, issued Jul. 31, 1990.
U.S. Pat. No. 5,370,684, issued Dec. 6, 1994.
U.S. Pat. No. 5,387,247, issued Feb. 7, 1995.
U.S. Pat. No. 5,421,816, issued Jul. 6, 1995.
U.S. Pat. No. 5,428,123, issued Jun. 27, 195.
U.S. Pat. No. 5,474,552, issued Dec. 12, 1995.
U.S. Pat. No. 5,569,186, issued Oct. 29, 1996.
U.S. Pat. No. 5,620,883, issued Apr. 15, 1997.
U.S. Pat. No. 5,653,755, issued Aug. 5, 1997.
U.S. Pat. No. 5,711,960, issued Jun. 27, 1998.
U.S. Pat. No. 5,779,734, issued Jul. 14, 1998.
U.S. Pat. No. 5,195,790, issued Aug. 18, 1998.
U.S. Pat. No. 5,800,420, issued Sep. 1, 1998.
U.S. Pat. No. 5,814,091, issued Sep. 29, 1998.

Almashanu, Musafia, Hader, Suissa, Kuhn, "Fusion of luxA and luxB and its expression in *Escherichia coli, Sacchromyces cerevisiae* and *Drosophila melanogaster,*" *J. Biolum. Chemilum.*, 5(2):89–98, 1990.

Anderson, Rossi, Tukey, Vu, Quattrochi, "A biomarker, P450 RGS, for assessing the induction potential of environmental samples," *Environ. Toxicol. Chem.*, 14:1159–1169, 1995.

Andrew and Roberts, "Construction of a bioluminescent Mycobacterium and its use for assay of antimycobacterial agents," *J. Clin. Microbiol.*, 31:2251–2254, 1993.

Aplin, Howe, Alahari and Juliano, "Signal transduction and signal modulation by cell adhesion receptors: the role of integrins, cadherins, immunoglobulin-cell adhesion molecules, and selectins," *Pharmacol. Rev.*, 50:197–263, 1998.

Applegate, Kehrmeyer and Sayler, "A modified mini-Tn5 system for chromosomally-introduced lux reprters for chemical sensing," *Appl. Environ. Microbiol.*, 64(7): 2730–2735, 1998.

Atanasov, Yang, Salehi, Ghindilis, Wilkins, Schade, "Implantation of a refillable glucose monitoring-telemetry device," *Biosensors and Bioelectron.*, 12:669–80, 1997.

Bagdasarian, Lurz, Ruckert, Franklin, Bagdasarian, Frey, Timmis, "Specific-purpose plasmid cloning vectors. II. Broad host range, high copy number, RSF1010-derived vectors, and a host-vector system for gene cloning in *Pseudomonas*," *Gene*, 16(1–3):237–247, 1981.

Baker et al., "Evaluation of an immunoisolation membrane formed by incorporating a polyvinyl alcohol hydrogel within a microporous support," *Cell Transplantation*, 6(6):585–595, 1997.

Balaguer et al., "Reporter cell lines to study the estrogenic effects of xenoestrogens," *Sci. Total. Environ.*, 233 (1–3):47–56, 1999.

Bantle and Thomas, "Glucose measurement in patients with diabetes mellitus with dermal interstitial fluid," *J. Lab. Clin. Med.*, 130(4):436–441, 1997.

Biondi, Baehler, Reymond, Veron, "Random insertion of GFP into the CAMP-dependent protein kinase regulatory subunit from *Dictyostelium discoideum*," *Nucelic Acids Res.*, 26:4946–52, 1998.

Boonyaratanakornkit et al., "Progesterone stimulation of human insulin-like growth factor-binding protein-5 gene transcription in human osteoblasts is mediated by a CACCC sequence in the proximal promoter," *J. Biol. Chem.*, 274(37):26431–8, 1999.

Borgese, Aggujaro, Carrera, Pietrini, Bassetti, "A role for N-myristoylation in protein targeting: NADH-cytochrome b5 reductase requires myristic acid for association with outer mitochondrial but not ER membranes," *J. Cell Biol.*, 135:1501–1513, 1996.

Boundy et al., "Regulation of tyrosine hydroxylase promoter activity by chronic morphine in TH9.0-LacZ transgenic mice," *J. Neurosci.*, 18(23):9989–95, 1998.

Brand, Holtzman, Scher, Ausiello, Stow, "Role of myristoylation in membrane attachment and function of $G\alpha_{i-3}$ on golgi membranes," *Am. J. Physiol.*, 96:C1362–C1369, 1996.

Burczak, Gamian, Kochman, "Long-term in vivo performance and biocompatibility of poly(vinyl alcohol) hydrogel macrocapsules for hybrid-type artificial pancreas," *Biomaterials*, 17(24):2351–2356, 1996.

Campanella, Aturki, Sammartino, Tomassetti, "Aspartate analysis in formulations using a new enzyme sensor, *J. Pharm. Biomed Anal.*, 13:439–47, 1995.

Campbell et al., "Regulation of the CYP1A1 promoter in transgenic mice: an exquisitely sensitive on-off system for cell specific gene regulation," *J. Cell Sci.*, 109(Pt 11):2619–25, 1996.

Cassidy, Lee, Trevors, "Environmental applications of immobilized cells: a review," *J. Ind. Microbiol*, 16:79–101, 1996.

Cebolla, Vazquez and Palomares, "Expression vectors for the use of eukaryotic luciferases as bacterial markers with different colors of luminescence," *Apple Environ. Microbiol.*, 61:660–668, 1995.

Coffey, Hawkey, Damstrup, Graves-Deal, Daniel, Dempsey, Chinery, Kirkland, DuBois, Jetton and Morrow, "Epidermal growth factor receptor activation induces nuclear targeting of cyclooxygenase-2, basolateral release of prostaglandins, and mitogenesis in polarizing colon cancer cells," *Proc. Natl. Acad. Sci. USA*, 94:657–562, 1997.

Coppola and Karl, "Pathology of early colonic neoplasia: clinical and pathologic features of precursor lesions and minimal carcinomas," *JMCC*, 4:160–166, 1998.

Demirpence, Duchesne, Badia, Gagne, Pons, "MVLN cells: a bioluminescent MCF-7-derived cell line to study the modulation of estrogenic activity," *J. Steroid Biochem. Molec. Biol.*, 46:355–364, 1995.

Doiron, Cuif, Chen, Kahn, "Transcriptional glucose signaling through the glucose response element is mediated by the pentose phosphate pathway," *J. Biol. Chem.*, 271(10):5321–5324, 1996.

Dupriez and Rousseau, "Glucose response elements in a gene that codes for 6-phosphofructo-2-kinase/fructose-2,6-bisphosphatase," *DNA Cell Biol.*, 16(9): 1075–1085, 1997.

Edenberg et al., "Polymorphism of the human alcohol dehydrogenase 4 (ADH4) promoter affects gene expression," *Pharmacogenetics*, 9(1):25–30, 1999.

Feng, Filvaroff and Derynck, "Transforming growth factor- (TGF- )-induced down-regulation of cyclin A expression requires a functional TGF- receptor complex. Characterization of chimeric and truncated type I and type II receptors," *J. Biol. Chem.*, 270:24237–24245, 1995.

Filatov, Bjorklund, Johansson, Thelander, "Induction of the mouse ribonucleotide reductase R1 and R2 genes in response to DNA damage to UV light," *J. Biol Chem.*, 271:23698–23704, 1996.

Foufelle, Gouhot, Pegorier, Perdereau, Girard, Ferre, "Glucose stimulation of lipogenic enzyme gene expression in cultured white adipose tissue. A role for glucose 6-phosphate," *J. Biol. Chem.*, 267(29):20543–20546, 1992.

Gagne, Balaguer, Demirpence, Chabret, Trousse, Nicolas, Pons, "Stable luciferase transfected cells for studying steroid receptor biological activity," *J. Biolum. Chemilum.*, 9:201–209, 1994.

Gastaldelli, Schwarz, Caveggion, Traber, Traber, Rosenblatt, Toffolo, Cobelli, Wolfe, "Glucose kinetics in interstitial fluid can be predicted by compartmental modeling," *Am. J. Physiol.*, 272(3-1):E494–505, 1997.

German and Wang, "The insulin gene contains multiple transcriptional elements that respond to glucose," *Mol. Cell. Biol.*, 14(6):4067–4075, 1994.

German, Moss, Rutter, "Regulation of insulin gene expression by glucose and calcium in transfected primary islet cultures," *J. Biol. Chem.*, 265:22063–22066, 1990.

Girard, Ferre, Foufelle, "Mechanisms by which carbohydrates regulate expression of genes for glycolytic and lipogenic enzymes," *Annu. Rev. Nutr.*, 17:325–352, 1997.

Gough, Armour, Baker, "Advances and prospects in glucose assay technology," *Diabetologia*, 40:S102–S107, 1997.

Gram, Nielson, Hansen, "Spontaneously silencing of humanized green fluorescent portien (hGFP) gene expression from a retroviral vector by DNA methylation," *J. Hematother*, 7:333–41, 1998.

Grygorczyk, Feighner, Adam, Liu, LeCouter, Dashkevicz, Hreniuk, Rydberg, Arena, "Detection of intracellular calcium elevations in *Xenopus lavis* oocytes: aequorin luminescence verus electrophysiology," *J. Neurosci. Methods*, 67:19–25, 1996.

Gu, Inoue, Shinohara, Doi, Kogire, Aung, Sumi, Imamura, Fujisato, Maetani, "Xenotransplantation of bioartificial pancreas using a mesh-reinforced polyvinyl alcohol bag," *Cell Transplant.*, 3(1):S19–S21, 1994.

Gupta and Goldwasser, "The role of the near upstream sequence in hypoxia-induced expression of the erythropoietin gene," *Nucleic Acids Res.*, 24:4768–4774, 1996.

Hanakam, Albrecht, Eckerskom, Matzner, Gerisch, "Myristoylated and non-myristoylated forms of the pH sensor protein hisactophilin II: intracellular shuttling to plasma membrane and nucleus monitored in real time by a fusion with green fluorescent protein, *EMBO J.*, 15:2935–43, 1996.

Hastings, "Chemistries and colors of bioluminescent reactions: a review," *Gene*, 173:5–11, 1996.

Hay, Applegate, Bright and Sayler, "A bioluminescent whole-cell reporter for the detection of 2,4-dichlorophenoxyacetic acid," *Appl. and Env. Microbiol.*, XX:XXX-XXX, 2000.

Hoffman, Sharma, Zhu, Ziyadeh, "Transcriptional activation of transforming growth factor-beta 1 in mesangial cell culture by high glucose concentration," *Kidney Int.*, 54(4):1107–1116, 1998.

Ilyas, Tomlinson, Rowan, Pignatelli and Bodmer, "β-Catenin mutations in cell lines established from human colorectal cancers," *Proc. Natl. Acad. Sci. USA*, 94:10330–10334, 1997.

Inoue et al., "Experimental hybrid islet transplantation: application of polyvinyl alcohol membranes for entrapment of islets," *Pancreas*, 7(5):562–568, 1992.

Jiricny, J, "Replication errors: challenging the genome," *EMBO J.*, 17:6427–6436, 1998.

Karran, "Microsatellite instability and DNA mismatch repair in human cancer," *Sem. Cancer Biol.*, 7:15–24, 1996.

Kennedy, Viollet, Rafiq, Kahn, Rutter, "Upstream stimulatory factor-2 (USF2) activity is required for glucose stimulation of L-pyruvate kinase promoter activity in single living islet β-cells," *J. Biol. Chem.*, 272:20636–20640, 1997.

King, DiGrazia, Applegate, Burlage, Sanseverino, Dunbar, Larimer and Sayler, "Rapid, sensitive bioluminescent reporter technology for naphthalene exposure and biodegradation," *Science*, 249:778–781, 1990.

Kinzler and Vogelstein, "Lessons from hereditary colorectal cancer," *Cell*, 87:159–170, 1996.

Kricka, "Chemiluminescence and bioluminescence," *Anal. Chem.*, 65:460R–462R, 1993.

Ksander, "Collagen coatings reduce the incidence of capsule contracture around soft silicone rubber implants in animals," *Ann. Plast. Surg.*, 20(3):215–224, 1988.

Kutchera, Jones, Matsunami, Groden, McIntyre, Zimmerman, White and Prescott, "Prostaglandin H synthase 2 is expressed abnormally in human colon cancer: evidence for a transcriptional effect," *Proc. Nat'l Acad. Sci. USA*, 93:4816–4820, 1996.

Laiho, Saksela and Keski-Oja, "Transforming growth factor- induction of type-1 plasminogen activator inhibitor," *J. Biol. Chem.*, 262:17467–17474, 1987.

Larger, Von Lucadou, Preidel, Ruprecht, Saeger, "Electrocatalytic glucose sensor," *Med. Biol. Eng. Comput.* 32:247–52, 1994.

Layton, Muccini, Ghosh, Sayler, "Construction of a bioluminescent reporter strain to detect polychlorinated biphenyls," *App. Environ. Microbiol.*, 64(12): 5023–5026, 1998.

Lengauer, Kinzler and Vogelstein, "Genetic instabilities in human cancers," *Nature*, 396:643–649, 1998.

Levy, Muldoon, Zolotukin, Link, "Retroviral transfer and expression of a humanized, red-shifted green fluorescent protein gene into human tumor cells," *Nat. Biotechnol*, 14:6104, 1996.

Malik, Beyersdorf-Radeck, Schmid, "Preservation of immobilized bacterial cell-matrix by drying for direct use in microbial sensors," *World J. Microbiol. Biotechnol.*, 9:243–247, 1993.

Markowitz, Wang, Myeroff, Parsons, Sun, Lutterbaugh, Fan, Zborowska, Kinzier, Vogelstein, Brattain and Willson, "Inactivation of the type II TGF-β receptor in colon cancer cells with microsatellite instability," *Science*, 268:1336–1338, 1995.

Marois, Chakfe, Guidoin, Duhamel, Roy, Marois, King, Douville, "An albumin-coated polyester arterial graft: in vivo assessment of biocompatibility and healing characteristics," *Biomaterials*, 17(1):3–14, 1996.

Meighen, "Molecular biology of bacterial biolurninescence," *Microbiol. Rev.*, 55:123–142, 1991.

Monaco, "Transplantation of pancreatic islets with immunoexclusion membranes," *Transplant Proc.*, 25(3): 2234–2236, 1993.

Morin, Sparks, Korinek, Barker, Clevers, Vogelstein and Kinzler, "Activation of β-catenin-Tcf signaling in colon cancer by mutations in β-catenin or APC," *Science*, 275:1787–1790, 1997.

Morin, Vogelstein and Kinzler, "Apoptosis and APC in colorectal tumorigenesis," *Proc. Natl. Acad. Sci. USA*, 93:7950–7954, 1996.

Moussy, Jakeway, Harrison, Rajotte, "In vitro and in vivo performance and lifetime of perfluorinated ionomer-coated glucose sensors after high-temperature curing," *Anal. Chem.*, 66(22):3882–3888, 1994.

Müller, Choidas, Reichmann and Ullrich, "Phosphorylation and free pool of β-catenin are regulated by tyrosine kinases and tyrosine phosphatases during epithelial cell migration," *J. Biol. Chem.*, 274:10173–10173, 1999.

Munemitsu, Albert, Rubenfield and Polakis, "Deletion of an amino-terminal sequence stabilizes -catenin in vivo and promotes hyperphosphorylation of the adenomatous polyposis coli tumor suppressor protein," *Mol. Cell Biol.*, 16:4088–4094, 1996.

Neufeld and White, "Nuclear and cytoplasmic localizations of the adenomatous polyposis coli protein," *Proc. Natl. Acad. Sci. USA*, 94:3034–3039, 1997.

Nicolaides, Papadopoulos, Liu, Wei, Carter, Ruben, Rosen, Haseltine, Fleischmann, Fraser, Adams, Venter, Dunlop, Hamilton, Peterson, de la Chapelle, Vogelstein and Kinzler, "Mutations in two PMS homologues in hereditary nonpolyposis colon cancer," *Nature*, 371:75–80, 1994.

Ohara, Dorit, Gilbert, "One-sided polymerse chain reaction: the amplification of cDNA," *Proc. Natl. Acad Sci. USA*, 86(15):5673–5677, 1989.

Ohgawara, Hirotani, Miyazaki, Teraoka, "Membrane immunoisolation of a diffusion chamber for bioartificial pancreas," *Artif Organs*, 22(9):788–794, 1998.

Olsen, DeBusscher, McCombie, "Development of broad-host-range vectors and gene banks: self-cloning of the *Pseudomonas aeruginosa* PAO chromosome," *J. Bacteriol.*, 150(1):60–69, 1982.

Patzer, Yao, Xu, Day, Wolfson, Liu, "A microchip glucose sensor," *Am. Soc. Artif. Intern. Organs.*, 41:M409–M413, 1995.

Peterson, Magnuson, and Andy Granner, "Location and characterization of two widely separated glucocorticoid response elements in the phosphoenolpyruvate carboxykinase gene," *Cell. Biol.*, 8:96–104, 1988.

Poitout, Moatti-Sirat, Reach, Zhang, Wilson, Lemonnier, Klein, "A glucose monitoring system for on line estimation in man of blood glucose concentration using a minaturized glucose sensor implanted in the subcutaneous tissue and a wearable control unit," *Diabetologia*, 36(7):658–663, 1993.

Prasher, "Using GFP to see the light," *Trends Genet.*, 11:320–329, 1995.

Prevost, Flori, Collier, Muscat and Rolland, "Application of AN69 Hydrogel to islet encapsulation," *Ann. N.Y. Acad. Sci.*, 831:344–349, 1997.

Quin, Wong, Magnuson, Shabb and Granner, "Identification of basal and cyclic AMP regulatory elements in the promoter of the phosphoenolpyruvate carboxykinase gene," *Mol. Cell. Biol.* 8:3467–3475, 1988.

Ramanathan, Ensor, Daunert, "Bacterial biosensors for monitoring toxic metals," *Trends Biotech.* 15:16–22, 1997.

Rubtsova, Kovba, Egorov, "Chemiluminescent biosensors based on porous supports with immobilized peroxidase," *Biosens. Bioelecton.*, 13:75–85, 1998.

Rudnick, Warren, McWherter, Toth, Machelski, Gordon, "Use of photoactivatable peptide substrates of *Saccharomyces cerevisiae* myristol-CoA-protein N-myristoyltransferase (Nmt1p) to characterize a myristol-CoA-Nmt1p-peptide ternary complex and to provide evidence for an ordered reaction mechanism," *Proc. Natl. Acad. Sci USA.*, 90:1087–1091, 1993.

Sambrook, Fritsch, Maniatis, In: *Molecular clonging: a laboratory manual*, 2$^{nd}$ Edition Cold Spring Harbor Laboratory Press, Plainview, N.Y., 1989.

Sasaki, Cripe, Koch, Andreone, Petersen, Beale and Granner, "Multihormonal regulation of phosphoenolpyruvate carboxykinase gene transcription," *J. Biol. Chem.*, 259:15242–15251, 1984.

Schmidt, Sluiter, Schoonen, "Glucose concentration in subcutaneous extracellular space," *Diabetes Care*, 16(5):695–700, 1993.

Selam, "Management of diabetes with glucose sensors and implantable insulin pumps," *ASAIO J.*, 137–142, 1997.

Sheng, Shao, Kirkland, Isakson, Coffey, Morrow, Beauchamp and DuBois, "Inhibition of human colon cancer cell growth by selective inhibition of cyclooxygenase-2," *J. Clin. Invest.*, 99:2254–2259, 1997.

Shibata, Toyama, Shioya, Ito, Hirota, Hasegawa, Matsumoto, Takano, Akiyama, Toyoshima, Kanamaru, Kanegae, Saito, Nakamura, Shiba and Noda, "Rapid colorectal adenoma formnation initiated by conditional targeting of the Apc gene," *Science*, 278:120–123, 1997.

Shih, Liu, Towle, "Two CACGTG motifs with proper spacing dictate the carbohydrate regulation of hepatic gene transcription," *J. Biol. Chem.*, 270(37): 21991–21997, 1995.

Short, J. M., A. Wynshaw-Boris, H. P. Short, Wynshaw-Boris, Short and Hanson," characterization of the phosphoenolpyruvate carboxykinase (GTP) promoter-regulatory region," *J. Biol. Chem.* 261:9721–9726, 1986.

Siegal and Isacoff, "A genetically encoded optical probe of membrane voltage," *Neuron*, 19:735–41, 1997.

Simpson, Dress, Ericson, Tellison, Sitter and Wintenberg, "A photospectrometer realized in standard intergrated circuit process," *Rev. of Sci. Instr.*, 69(2):377–383, February 1998.

Simpson, Ericson, Jellsion, Jr., Dress, Wintenberg and Bobrek, "Application specific spectral response with CMOS compatible photodiodes," *IEEF Transactions on Electron Devices*, 46(5):905–913, 1999.

Simpson, Paulus, Jellison, Sayler, Applegate, Ripp, Nivens, "Bioluminescent bioreporter integrated circuits (BBICs): whole-cell chemical biosensors," *Technical Digest of 1998 Solid-State Sensors and Actuators Conference*, Hilton Head Island, S.C., pp 354–357, 1998b.

Simpson, Sayler, Applegate, Ripp, Nivens, Paulus and Jellison, "Bioluminescent Bioreporter Integrated Circuits (BBICs) Bioluminescent Bioreporter Integrated Circuits (BBICs): Whole-Cell Environmental Monitoring Devices," to be presented at the 29th International Conference on Environmental Systems, Jul. 15, 1999.

Simpson, Sayler, Applegate, Ripp, Nivens, Paulus and Jellison, Jr., "Bioluminescent-bioreporter integrated circuits form novel whole-cell biosensors," *Trends in Biotechnology*, 16:332–338, 1998.

Simpson, Sayler, Ripp, Paulus and Jellison, "Bioluminescent bioreporter integrated circuits (BBICs)," *Smart Structures and Materials 1998: Smart Electronics and MEMS*, Varadan, McWhorter, Singer and Vellekoop, Eds., *Proceedings of SPIE*, 3328:202–212, 1998.

Smyrk, "Colon cancer connections. Cancer syndrome meets molecular biology meets histopathology," *Am. J. Pathol.*, 145:1–6, 1994.

Srikantha, Klapach, Lorenz, Tsai, Laughlin, Gorman, Soll, "The sea pansy *Renilla reniformis* luciferase serves as a sensitive bioluminescent reporter for differential gene expression in Candida albicans," *J. Bacteriol.*, 178:121–129, 1996.

Steinberg, Poziomek, Engelman, Rogers, "A review of environmental applications of bioluminescence measurements," *Chemosphere*, 30:2155–2197, 1995.

Sternberg, Bindra, Wilson, Thevenot, "Covalent enzyme coupling on cellulose acetate membranes for glucose sensor development," *Anal. Chem.*, 60(24):2781–2786, 1988.

Sternberg, Meyerhoff, Mennel, Bischof, Pfeiffer, "Subcutaneous glucose concentration in humans. Real estimation and continuous monitoring," *Diabetes Care*, 18(9): 1266–1269, 1995.

Suzuki K., S. Bonner-Weir, J. Hollister-Lock, C. K. Colten, and GS Weir, "Number and volume of islets transplanted in immunobarrier devices," *Cell Transplant.*, 7(1):47–52, 1998.

Takaku, Oshima, Miyoshi, Matsui, Seldin and Taketo, "Intestinal tumorigenesis in compound mutant mice of both Dpc4 (Smad4) and Apc genes," *Cell*, 92:645–656, 1998.

Taniguchi, Fukao, Nakauchi, "Constant delivery of proinsulin by encapsulation of transfected cells," *J. Surg. Res.*, 70(1):41–45, 1997.

Tu and Mager, "Biochemistry of bacterial bioluminescence," *Photochem. Photobiol.*, 62:615–624, 1995.

Tziampazis and Sambanis, "Tissue engineering of a bio-artificial pancrease: modeling the cell environment and device function," *Biotechnol. Prog.*, 11(2):115–126, 1995.

Vaidya and Wilkins, "Application of polytetrafluoroethylene (PTFE) membranes to control interference effects in a glucose biosensor," *Biomed. Instrum. Technol.*, 27(6):486–494, 1993.

Vaidya and Wilkins, "Use of charged membranes to control interference by body chemicals in a glucose biosensor," *Med. Eng. Phys.*, 16(5):416–421, 1994.

Wallace, Fleming, White and Sayler, "An algD-bioluminescent reporter plasmid to monitor alginate expression in biofilms," *Microb. Ecol.*, 27:224–240, 1994.

Wang, Ji, Yuan, "Study of cellulose acetate membrane-based glucose biosensors," *Chin. J. Biotechnol.*, 11(3):199–205, 1995.

Wang, Sun, Myeroff, Wang, Gentry, Yang, Liang, Zborowska, Markowitz, Willson and Brattain, "Demonstration that mutation of the type II transforming growth factor receptor inactivates its tumor suppressor activity in replication error-positive colon carcinoma cells," *J. Biol. Chem.*, 270:22044–22049, 1995.

Ward, Wilgus, Troupe, "Rapid detection of hyperglycaemia by a subcutaneously-implanted glucose sensor in the rat," *Biosens. Bioelectron.*, 9(6):423–428, 1994.

Wilkins, Atanasov, Muggenburg, "Integrated implantable device for long-term glucose monitoring," *Biosens. Bioelectron.*, 10:485–494, 1995.

Wolfson, Tokarsky, Yao, Krupper, "Glucose concentration at possible sensor tissue implant sites," *Diabetes Care*, 5(3):162–165, 1982.

Wu, Storrier, Pariente, Wang, Shapleigh, Abruna, "A nitrate biosensor based on a maltose binding protein nitrite reductase fusion immobilized on an electropolymerized film of a pyrrole-derived bipyridinium," *Anal. Chem.* 69:4856–63, 1997.

Yao, Xu, Day, Patzer, "Interference of amino acids on glucose sensing," *Am. Soc. Artif. Intern. Organs J*, 40:33–40, 1994.

Young, Yao, Chang, Chen, "Evaluation of asymmetric poly(vinyl alcohol) membranes for use in artificial islets," *Biomaterials*, 17(22):2139–2145, 1996.

Zhu, Richardson, Parada and Graff, "Smad3 mutant mice develop metastatic colorectal cancer," *Cell*, 94:703–714, 1998.

Zolotukkhin, Potter, Hauswirth, Guy, Muzyczka, "A 'humanized' green fluorescent protein cDNA adapted for high-level expression in mamalian cells," *J. Virol.* 70:4646–54, 1996.

Zondervan, Hoppen, Pennings, Fritschy, Wolters, van Schilfgaarde, "Design of a polyurethane membrane for the encapsulation of islets of Langerhans," *Biomaterials*, 13(3):136–144, 1992.

All of the compositions, methods, devices, apparatus and systems disclosed and claimed herein can be made and executed without undue experimentation in light of the present disclosure. While the methods, devices, apparatus and systems of this invention have been described in terms of preferred embodiments, it will be apparent to those of skill in the art that variations may be applied to the methods, devices, apparatus and systems and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An implantable monolithic bioelectronic device for detecting at least one analyte within the body of an animal, said device comprising:

an integrated circuit including at least one transducer for generating an electrical signal in response to light incident thereon, a bioreporter, said bioreporter for emitting light when exposed to said analyte, said bioreporter positioned so that at least a portion of said emitted light reaches said transducer, and a biocompatible housing surrounding said integrated circuit and said bioreporter, said biocompatible housing including a semi-permeable membrane region for allowing passage of said analyte to said bioreporter but restricting passage of said bioreporter out from said housing.

2. The implantable monolithic bioelectronic device of claim 1, wherein said bioreporter is disposed in a polymeric matrix, said polymer matrix for keeping said bioreporter in place over said integrated circuit.

3. The implantable monolithic bioelectronic device of claim 2, wherein said polymeric matrix comprises polyvinyl alcohol, poly-L-lysine, or alginate.

4. The implantable monolithic bioelectronic device of claim 2, wherein said polymeric matrix comprises a microporous, mesh-reinforced or filter-supported hydrogel.

5. The implantable monolithic bioelectronic device of claim 1, wherein said integrated circuit comprises a phototransducer.

6. The implantable monolithic bioelectronic device of claim 5, further comprising a transparent, biocompatible, bioresistant separator operably positioned between the phototransducer and the bioreporter.

7. The implantable monolithic bioelectronic device of claim 1, wherein said bioreporter comprises a plurality of genetically engineered eukaryotic or prokaryotic cells, "wherein said genetically engineered cells has Lux gene, such that the Lux gene" permits said cells to produce a bioluminescent reporter polypeptide in response to the presence of said analyte.

8. The implantable monolithic bioelectric device of claim 7, wherein said plurality of eukaryotic cells comprise mammalian cells.

9. The implantable monolithic bioelectronic device of claim 8, wherein said plurality of eukaryotic cells comprise islet β-cells, immortal stem cells, or hepatic cells.

10. The implantable monolithic bioelectronic device of claim 9, wherein said plurality of eukaryotic cells comprise recombinant human immortal stem cells.

11. The implantable monolithic bioelectronic device of claim 7, wherein said plurality of cells comprise a nucleic acid segment that encodes a luciferase polypeptide or a green fluorescent protein that is produced by said cells in response to the presence of said analyte.

12. The implantable monolithic bioelectronic device of claim 1, wherein said analyte is glucose, glucagon or insulin.

13. The implantable monolithic bioelectronic device of claim 1, further comprising a source of nutrients for sustaining cells disposed inside said biocompatible housing.

14. The implantable monolithic bioelectronic device of claim 1, further comprising a wireless transmitter, said wireless transmitter disposed inside said biocompatible housing and communicably connected to said transducer.

15. The implantable monolithic bioelectronic device of claim 1, further comprising an antenna, said antenna disposed inside said biocompatible housing and communicably connected to said transducer.

16. The implantable monolithic bioelectronic device of claim 1, further comprising an implantable drug delivery pump capable of being controlled by said device and a drug reservoir for holding at least one drug, said pump disposed inside said biocompatible housing, said pump for delivering said drug to the body of said animal.

17. The implantable monolithic bioelectronic device of claim 1, wherein said bioreporter expresses said light-emitting polypeptide following the metabolism of said analyte by said bioreporter.

18. The implantable monolithic bioelectronic device of claim 6, wherein said bioresistant separator comprises silicon nitride or silicon dioxide.

19. The implantable monolithic bioelectronic device of claim 1, wherein said integrated circuit is a complementary metal oxide semiconductor (CMOS) integrated circuit.

20. The implantable monolithic bioelectronic device of claim 5, wherein said phototransducer comprises a photodiode.

21. The implantable monolithic bioelectronic device of claim 1, wherein said integrated circuit further comprises a photodiode and a current to frequency converter.

22. The implantable monolithic bioelectronic device of claim 1, wherein said integrated circuit further comprises a current to frequency converter and a digital counter.

23. The implantable monolithic bioelectronic device of claim 1, further comprising a wireless transmitter, said wireless transmitter disposed inside said biocompatible housing and communicably connected to said transducer.

24. The implantable monolithic bioelectronic device of claim 23, wherein said transmitter is for transmitting digital data.

25. An implantable controlled drug delivery system, comprising the device of claim 1, further comprising an implantable drug delivery pump and a drug reservoir disposed inside said biocompatible housing for providing at least one drug to said animal, said bioelectric device controlling a level of said drug provided to said animal based on a measured concentration of said analyte.

26. A kit for the detection of an analyte comprising the device of claim 1 and instructions for using said device.

27. The kit of claim 26, further comprising a standardized reference solution.

* * * * *